US012354008B2

(12) United States Patent
Dutta et al.

(10) Patent No.: US 12,354,008 B2
(45) Date of Patent: Jul. 8, 2025

(54) KNOWLEDGE DISTILLATION AND GRADIENT PRUNING-BASED COMPRESSION OF ARTIFICIAL INTELLIGENCE-BASED BASE CALLER

(71) Applicant: Illumina, Inc., San Diego, CA (US)

(72) Inventors: Anindita Dutta, San Francisco, CA (US); Gery Vessere, Oakland, CA (US); Dorna Kashefhaghighi, Menlo Park, CA (US); Kishore Jaganathan, San Francisco, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 698 days.

(21) Appl. No.: 17/176,151

(22) Filed: Feb. 15, 2021

(65) Prior Publication Data

US 2021/0265018 A1 Aug. 26, 2021

Related U.S. Application Data

(60) Provisional application No. 62/979,385, filed on Feb. 20, 2020.

(51) Int. Cl.
*G06N 3/082* (2023.01)
*G06F 18/214* (2023.01)
(Continued)

(52) U.S. Cl.
CPC ........... *G06N 3/082* (2013.01); *G06F 18/214* (2023.01); *G06N 3/063* (2013.01); *G06N 3/08* (2013.01);
(Continued)

(58) Field of Classification Search
None
See application file for complete search history.

(56) References Cited

U.S. PATENT DOCUMENTS 5,641,658 A 6/1997 Adams et al.
6,090,592 A 7/2000 Adams et al.
(Continued)

FOREIGN PATENT DOCUMENTS

CA 2894317 A1 12/2016
CA 3104851 A1 11/2020
(Continued)

OTHER PUBLICATIONS

Mansar, Y. (Feb. 15, 2020). Build powerful lightweight models using knowledge distillation. Medium. https://towardsdatascience.com/build-powerful-lightweight-models-using-knowledge-distillation-618f69b569d9#:~:text=The%20basic%20idea%20behind%20Knowledge,try%20to%20mimic%20the%20Teacher. (Year: 2020).*
(Continued)

*Primary Examiner* — Karlheinz R. Skowronek
*Assistant Examiner* — Noah A. Auger
(74) *Attorney, Agent, or Firm* — Illumina, Inc.

(57) ABSTRACT

The technology disclosed compresses a larger, teacher base caller into a smaller, student base caller. The student base caller has fewer processing modules and parameters than the teacher base caller. The teacher base caller is trained using hard labels (e.g., one-hot encodings). The trained teacher base caller is used to generate soft labels as output probabilities during the inference phase. The soft labels are used to train the student base caller.

20 Claims, 34 Drawing Sheets

(5 of 34 Drawing Sheet(s) Filed in Color)

(51) Int. Cl.
    *G06N 3/063*     (2023.01)
    *G06N 3/08*     (2023.01)
    *G06N 5/04*     (2023.01)
    *G06V 10/44*     (2022.01)
    *G06V 10/82*     (2022.01)
    *G16B 40/20*     (2019.01)

(52) U.S. Cl.
    CPC .............. *G06N 5/04* (2013.01); *G06V 10/454* (2022.01); *G06V 10/82* (2022.01); *G16B 40/20* (2019.02)

(56) References Cited

U.S. PATENT DOCUMENTS

| | | |
|---|---|---|
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 8,182,993 B2 | 5/2012 | Tomaney et al. |
| 8,241,573 B2 | 8/2012 | Banerjee et al. |
| 8,392,126 B2 | 3/2013 | Mann |
| 8,401,258 B2 | 3/2013 | Hargrove et al. |
| 8,407,012 B2 | 3/2013 | Erlich et al. |
| 8,594,439 B2 | 11/2013 | Staelin et al. |
| 8,725,425 B2 | 5/2014 | Heiner et al. |
| 8,795,971 B2 | 8/2014 | Kersey et al. |
| 8,965,076 B2 | 2/2015 | Garcia et al. |
| 9,279,154 B2 | 3/2016 | Previte et al. |
| 9,453,258 B2 | 9/2016 | Kain et al. |
| 9,708,656 B2 | 7/2017 | Turner et al. |
| 10,023,911 B2 | 7/2018 | Tomaney et al. |
| 10,068,054 B2 | 9/2018 | Van Rooyen et al. |
| 10,152,776 B2 | 12/2018 | Langlois et al. |
| 10,168,438 B2 | 1/2019 | Dennis et al. |
| 10,241,075 B2 | 3/2019 | Davey et al. |
| 10,354,747 B1 | 7/2019 | DePristo et al. |
| 10,423,861 B2 | 9/2019 | Gao et al. |
| 10,491,239 B1 | 11/2019 | Hubara |
| 10,527,549 B2 | 1/2020 | Rebetez et al. |
| 10,540,591 B2 | 1/2020 | Gao et al. |
| 10,619,195 B2 | 4/2020 | Lamb et al. |
| 10,648,027 B2 | 5/2020 | Mannion et al. |
| 10,711,299 B2 | 7/2020 | Rothberg et al. |
| 10,713,794 B1 | 7/2020 | He et al. |
| 10,740,880 B2 | 8/2020 | Paik et al. |
| 10,740,883 B2 | 8/2020 | Zerfass et al. |
| 10,755,810 B2 | 8/2020 | Buckler et al. |
| 10,963,673 B2 | 3/2021 | Schaumberg et al. |
| 11,138,496 B2 | 10/2021 | Seth |
| 2002/0055100 A1 | 5/2002 | Kawashima et al. |
| 2003/0062485 A1 | 4/2003 | Fernandez et al. |
| 2004/0002090 A1 | 1/2004 | Mayer et al. |
| 2004/0096853 A1 | 5/2004 | Mayer |
| 2006/0014151 A1 | 1/2006 | Ogura et al. |
| 2006/0040297 A1 | 2/2006 | Leamon et al. |
| 2006/0064248 A1 | 3/2006 | Saidi et al. |
| 2006/0188901 A1 | 8/2006 | Barnes et al. |
| 2006/0240439 A1 | 10/2006 | Smith et al. |
| 2006/0269130 A1 | 11/2006 | Maroy et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0234136 A1 | 9/2008 | Drmanac et al. |
| 2008/0242560 A1 | 10/2008 | Gunderson et al. |
| 2009/0081775 A1 | 3/2009 | Hodneland et al. |
| 2010/0046830 A1 | 2/2010 | Wang et al. |
| 2010/0111370 A1 | 5/2010 | Black et al. |
| 2010/0157086 A1 | 6/2010 | Segale et al. |
| 2011/0059865 A1 | 3/2011 | Smith et al. |
| 2011/0065607 A1 | 3/2011 | Kersey et al. |
| 2011/0281736 A1 | 11/2011 | Drmanac et al. |
| 2011/0286628 A1 | 11/2011 | Goncalves et al. |
| 2011/0295902 A1 | 12/2011 | Mande et al. |
| 2012/0015825 A1 | 1/2012 | Zhong et al. |
| 2012/0020537 A1 | 1/2012 | Garcia et al. |
| 2013/0059740 A1 | 3/2013 | Drmanac et al. |
| 2013/0079232 A1 | 3/2013 | Kain et al. |
| 2013/0124100 A1 | 5/2013 | Drmanac et al. |
| 2013/0188866 A1 | 7/2013 | Obrador et al. |
| 2013/0250407 A1 | 9/2013 | Schaffer et al. |
| 2014/0051588 A9 | 2/2014 | Drmanac et al. |
| 2014/0152801 A1 | 6/2014 | Fine et al. |
| 2015/0079596 A1 | 3/2015 | Eltoukhy et al. |
| 2015/0117784 A1 | 4/2015 | Lin et al. |
| 2015/0169824 A1 | 6/2015 | Kermani et al. |
| 2016/0042511 A1 | 2/2016 | Chukka et al. |
| 2016/0078272 A1 | 3/2016 | Hammoud |
| 2016/0110498 A1 | 4/2016 | Bruand et al. |
| 2016/0196479 A1 | 7/2016 | Chertok et al. |
| 2016/0350914 A1 | 12/2016 | Champlin et al. |
| 2016/0356715 A1 | 12/2016 | Zhong et al. |
| 2016/0357903 A1 | 12/2016 | Shendure et al. |
| 2016/0371431 A1 | 12/2016 | Haque et al. |
| 2017/0044601 A1 | 2/2017 | Crnogorac et al. |
| 2017/0098032 A1 | 4/2017 | Desai et al. |
| 2017/0116520 A1 | 4/2017 | Min et al. |
| 2017/0161545 A1 | 6/2017 | Champlin et al. |
| 2017/0169313 A1 | 6/2017 | Choi et al. |
| 2017/0249421 A1 | 8/2017 | Eberle et al. |
| 2017/0249744 A1 | 8/2017 | Wang et al. |
| 2017/0362634 A1 | 12/2017 | Ota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 | 6/2019 | Buckler et al. |
| 2019/0213473 A1 | 7/2019 | Dutta et al. |
| 2019/0237160 A1* | 8/2019 | Rothberg ............... G06N 20/00 |
| 2019/0237163 A1 | 8/2019 | Wang et al. |
| 2019/0244348 A1 | 8/2019 | Buckler et al. |
| 2019/0266491 A1 | 8/2019 | Gao et al. |
| 2019/0114511 A1 | 9/2019 | Gao et al. |
| 2019/0272638 A1 | 9/2019 | Mouton et al. |
| 2019/0318806 A1 | 10/2019 | Wise et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0125947 A1 | 4/2020 | Park et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0303039 A1 | 9/2020 | Pratt et al. |
| 2020/0320294 A1 | 10/2020 | Mangal et al. |

(56) References Cited

U.S. PATENT DOCUMENTS

| | | |
|---|---|---|
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0390278 A1 | 12/2021 | Van Leeuwen et al. |

FOREIGN PATENT DOCUMENTS

| | | |
|---|---|---|
| CN | 110245685 A | 9/2019 |
| EP | 3130681 A1 | 2/2017 |
| EP | 3373238 A1 | 9/2018 |
| JP | 2007199397 A | 8/2007 |
| NL | 2023310 B1 | 9/2020 |
| NL | 2023311 B1 | 9/2020 |
| NL | 2023312 B1 | 9/2020 |
| NL | 2023314 B1 | 9/2020 |
| NL | 2023316 B1 | 9/2020 |
| RU | 2706960 C1 | 11/2019 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |
| WO | 2007123744 A2 | 11/2007 |
| WO | 2008154317 A1 | 12/2008 |
| WO | 2012058096 A1 | 5/2012 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079166 A1 | 4/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Turing. (Feb. 11, 2022). Understanding feed forward neural networks in deep learning. Turing Enterprises Inc. https://www.turing.com/kb/mathematical-formulation-of-feed-forward-neural-network#why-are-neural-networks-used? (Year: 2020).*
Gerencer, T. (Oct. 30, 2019). Parallel Computing And Its Modern Uses | HP® Tech Takes. Www.hp.com. https://www.hp.com/us-en/shop/tech-takes/parallel-computing-and-its-modern-uses (Year: 2019).*
Chen, C., Khaleel, S. S., Huang, H., & Wu, C. H. (2014). Software for pre-processing Illumina next-generation sequencing short read sequences. Source code for biology and medicine, 9, 1-11. (Year: 2014).*
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et. al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.

(56) References Cited

OTHER PUBLICATIONS

Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.
PCT/US2020/024092, International Preliminary Report on Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
PCT/US2020/033281, Second Article 34 Amendment Letter in response to Second Written Opinion, dated Jul. 10, 2021, 4 pages.
PCT/US2021/018422 International Search Report and Written Opinion, dated Jun. 10, 2021, 12 pages.
Aggarwal, Neural Networks and Deep Learning: A Textbook, Springer, dated Aug. 26, 2018, 512 pages.
Wang et. al., Deep Neural Network Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.
PCT/US2021/018913 International Search Report and Written Opinion, dated Jun. 10, 2021, 11 pages.
Zeng et. al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et. al., Efficient Processing of Deep Neural Networks: A Tutorial and Survey, Cornell University Library, dated Mar. 27, 2017, 21 pages.
Sundaram, L. et. al., "Predicitng the clinical impact of human mutation with deep neural networks", Nat. Genet. 50, 1161-1170 (2018).
Jaganathan, K. et. al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonic de novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure—pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6, 15 (Springer, Cham, Switzerland; 2016).
Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).

(56) References Cited

OTHER PUBLICATIONS

Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.

Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et. al., "CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation. "International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.

(56) References Cited

OTHER PUBLICATIONS

Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?. " 2016 international conference on digital image computing—techniques and applications (DICTA). IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al, ImageNet Classification with Deep Convolutional Neural Networks, 2012, 9 Pages.
Geeks for Geeks, "Underfitting and Overfilling in Machine Learning", [retrieved on Aug. 26, 2019]. Retrieved from the Internet <www.geeksforgeeks.org/underfitting-and-overfitting-in-machine-learning/>, 2 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
PCT/US2019031621—International Search Report and Written Opinion dated Aug. 7, 2019, 17 pages.
Carter et al., "Cancer-specific high-throughput annotation of somatic mutations—computational prediction of driver missense mutations," Cancer research 69, No. 16 (2009) pp. 6660-6667.
Albrecht et. al., Deep learning for single-molecule science, Nanotechnology (28), dated 2017, 423001, 11 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
PCT/US2020/24088 PCT Direct Letter, filed Mar. 21, 2020, 4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.
PCT/US2020/024088 Partial Search Report and Invitation to Pay Fees, dated Jul. 8, 2020, 22 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et. al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.
PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et. al., Improved base-calling for the Illumina Genome Analyzer using Machine Learning Strategies, Genome Biology, published Aug. 14, 2009, 9 pages.
PCT/US2020/033281 Second Written Opinion, dated May 10, 2021, 8 pages.
Angermueller, Christof, et. al., Deep learning for computational biology, Molecular Systems Biology, dated Jun. 6, 2016, 16 pages.
PCT/US2021/018258 International Search Report and Written Opinion, dated May 26, 2021, 17 pages.
Smith et. al., Barcoding and demultiplexing Oxford nanopore native RNA sequencing reads with deep residual learning, bioRxiv, dated Dec. 5, 2019, 18 pages.

(56) References Cited

OTHER PUBLICATIONS

PCT/US2021/018910 Partial Search Report and Invitation to pay fee, dated May 31, 2021, 14 pages.
PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2021/018917—Second Written Opinion, dated Feb. 4, 2022, 7 pages.
PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silica Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
U.S. Appl. No. 16/825,987, filed Mar. 20, 2020, U.S. Pat. No. 11,347,965, May 31, 2022, Issued.
U.S. Appl. No. 16/825,991, filed Mar. 20, 2020, U.S. Pat. No. 11,210,554, Dec. 28, 2021, Issued.
U.S. Appl. No. 16/826,126, filed Mar. 20, 2020, US-2020-0302297-A1, Sep. 24, 2020 Pending.
U.S. Appl. No. 16/826,134, filed Mar. 20, 2020, US-2020-0327377-A1, Oct. 15, 2020, Pending.
U.S. Appl. No. 16/826,168, filed Mar. 21, 2020, US-2020-0302224-A1, Sep. 24, 2020, Allowed.
U.S. Appl. No. 17/529,222, filed Nov. 17, 2021, US-2022-0147760-A1, May 12, 2022, Pending.
U.S. Appl. No. 17/827,612, filed May 27, 2022, Pending.
U.S. Appl. No. 16/874,633, filed May 14, 2020, US-2020-0364565-A1, Nov. 19, 2020, Allowed.
U.S. Appl. No. 17/703,975, filed Mar. 24, 2022, Pending.
U.S. Appl. No. 17/175,546, filed Feb. 12, 2021, US-2021-0265009-A1, Aug. 26, 2021, Pending.
U.S. Appl. No. 17/180,542, filed Feb. 19, 2021, US-2021-0265017-A1, Aug. 26, 2021, Pending.
U.S. Appl. No. 17/411,980, filed Aug. 25, 2021, US-2022-0067489-A1, Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/176,147, filed Feb. 15, 2021, US-2021-0265015-A1, Aug. 26, 2021, Pending.
U.S. Appl. No. 17/179,395, filed Feb. 18, 2021, US-2021-0265016-A1, Aug. 26, 2021, Pending.
U.S. Appl. No. 17/180,480, filed Feb. 19, 2021, US-2021-0264266-A1, Aug. 26, 2021, Pending.
U.S. Appl. No. 17/180,513, filed Feb. 19, 2021, US-2021-0264267-A1, Aug. 26, 2021, Pending.
U.S. Appl. No. 17/687,586, filed Mar. 4, 2022, Pending.
U.S. Appl. No. 17/232,056, filed Apr. 15, 2021, Pending.
U.S. Appl. No. 17/468,411, filed Sep. 7, 2021, Pending.
U.S. Appl. No. 17/830,287, filed Jun. 1, 2022, Pending.
U.S. Appl. No. 17/830,316, filed Jun. 1, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2021/018422, Feb. 17, 2021, Pending
PCT/US2020/024090, Mar. 21, 2020, WO 2020/191389, Sep. 24, 2020, Nationalized.
PCT/US2020/024087, Mar. 21, 2020, WO 2020/205296, Oct. 8, 2020, Nationalized.
PCT/US2020/024088, Mar. 21, 2020, WO 2020/191387, Sep. 24, 2020, Nationalized.
PCT/US2020/024091, Mar. 21, 2020, WO 2020/191390, Sep. 24, 2020, Nationalized.
PCT/US2020/024092, Mar. 22, 2020, WO 2020/191391, Sep. 24, 2020, Nationalized.
PCT/US2020/033280, May 15, 2020, WO 2020/232409, Nov. 19, 2020, Nationalized.
PCT/US2020/033281, May 15, 2020, WO 2020/232410, Nov. 19, 2020, Nationalized.
PCT/US2021/018258, Feb. 16, 2021, Pending.
PCT/US2021/018910, Feb. 19, 2021, Pending.
PCT/US2021/047763, Aug. 26, 2021, Pending.
PCT/US2022/020460, Mar. 15, 2022, Pending.
PCT/US2022/020462, Mar. 15, 2022, Pending.
PCT/US2021/018427, Feb. 17, 2021, Pending.
PCT/US2021/018913, Feb. 19, 2021, Pending.
PCT/US2021/018915, Feb. 19, 2021, Pending.
PCT/US2021/018917, Feb. 19, 2021, Pending.
PCT/US2022/021814, Mar. 24, 2022, Pending.
PCT/US2022/24911, Apr. 14, 2022, Pending.
PCT/US2022/24913, Apr. 14, 2022, Pending.
PCT/US2022/035564, Jun. 29, 2022, Pending.
PCT/US2022/035567, Jun. 29, 2022, Pending.
PCT/US2022/035847, Jun. 30, 2022, Pending.
PCT/US2022/24916, Apr. 14, 2022, Pending.
PCT/US2022/24918, Apr. 14, 2022, Pending.
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.

(56) References Cited

OTHER PUBLICATIONS

Pei et al., A Topological Measurement for Weighted Protein Interaction Network, IEEE Computational Systems Bioinformatics Conference dated 2005, 11 pages.
Assfalg et. al., "3DString, A Feature String Kernel for 3D Object Classification on Voxelized Data", dated Nov. 6, 2006, 10 pages.
NL 2023311 NL Search Report, dated Mar. 24, 2020, 15 pages.
NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
U.S. Appl. No. 16/825,991—Notice of Allowance dated Aug. 5, 2021, 10 pages.
Krishnakumar et. al., Systematic and stochastic influences on the performance of the MinION nanopore sequencer across a range of nucleotide bias, Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
U.S. Appl. No. 16/826,168—Office Action dated Aug. 31, 2021, 55 pages.
Kircher-etal_Improved-base-calling-for-the-Illumina-Genome-Analyzer-using-machine-learning-strategies_14August2009_10pages.
Albrecht et al., Deep learning for single molecule science, Nanotechnology, dated Sep. 18, 2017, 11 pages.
U.S. Appl. No. 16/825,987—Office Action (Quayle) dated Oct. 19, 2021, 85 pages.
PCT/US2021047763—International Search Report and Written Opinion, dated Dec. 20, 2021, 11 pages.
PCT/US2021/018422 Second Written Opinion, dated Feb. 4, 2022, 8 pages.
Adriana Romero et. al., FitNets: Hints for Thin Deep Nets, published Mar. 27, 2015, 13 pages.
U.S. Appl. No. 16/874,599—Notice of Allowance dated Dec. 3, 2021, 12 pages.
U.S. Appl. No. 16/825,987—Response to Office Action (Quayle) dated Oct. 19, 2021, filed Jan. 13, 2022, 11 pages.
U.S. Appl. No. 16/825,987—Notice of Allowance, dated Jan. 28, 2022, 12 pages.
U.S. Appl. No. 16/825,987—Supplemental Notice of Allowance, dated Feb. 7, 2022, 8 pages.
U.S. Appl. No. 16/826,168—Response to Office Action dated Aug. 31, 2021, filed Jan. 31, 2022, 15 pages.
CN 2020800036223—Voluntary Amendments, filed May 20, 2021, 26 pages.
EP 20719053.9—Rules 161(2) and 162 Communication, dated Oct. 28, 2021, 3 pages.
IL 279522—Response to Notice Before Acceptance dated Aug. 1, 2021, filed Nov. 28, 2021, 3 pages.
KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.
Wang et. al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Report on Patentability, dated Jul. 23, 2021, 11 pages.
Pfeiffer et. al., Systematic evaluation of error rates and causes in short samples in next-generation sequencing, Scientific Reports, published Jul. 19, 2018, 14 pages.
PCT/US2020/033281—International Preliminary Report on Patentability, dated Aug. 31, 2021, 10 pages.
Min, et. al., "Deep Learning in Bioinformatics", Jun. 19, 2016, 46pgs.
Jiminez et. al., DeepSite—protein binding site predictor using 3D CNNs, dated Oct. 1, 2017, 7 pages.
Pu et. al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.

(56) References Cited

OTHER PUBLICATIONS

Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Ilumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Lutteropp, Error-Profile-Aware Correction of Next Generation Sequencing Reads, Karlsruhe Institute of Technology, dated Mar. 31, 2017, 96 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Bentley et. al., Accurate Whole Human Genome Sequencing using Reversible Terminator Chemistry, Nature, Nov. 2008, 21 pages.
Ilumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).

(56) References Cited

OTHER PUBLICATIONS

Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Jeschke, J. G. & Currie, P. D. Animal models of human disease—zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 14 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., Wavenet: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages. [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.

(56) References Cited

OTHER PUBLICATIONS

Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network. International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
PCT/US2020/024090 Article 34 Amendment, dated Dec. 4, 2020, 6 pages.
PCT/US2020/024090 Article 34 Amendment, dated Mar. 18, 2021, 3 pages.
Grange, NGS: the basics, Institut Jacques Monod, dated Jun. 26, 2000, 59 pages.
Illumina CMOS Chip and One-Channel SBS Chemistry, Illumina Inc, 2018, 4 pages.
Illumina, GA Bootcamp, Sequencing Module 3 :Overview, Broad Institute, 73 pages, retrieved on Jul. 22, 2021T, Retrieved from [URL: https://www.google.com/search?q=broad+institute+sequencing+module+3 t-overview&client=firefox-b1e&sxsrf-ALeKk02079LD_qrHqvhfFGRnNCUw8Z6QJA%3A1628296030482&ei=XIMNYYHMPi-gS61onoCQ&q=broad+institute+sequencing+module+3roverview&gs_lcp=Cgdnd3Mtd216EAM6BwgjELADECdKBQg6EgExSgQIQRgBUPn9AVj5_QFg1ZQCaAFwAHgAgAFt.
Massingham et. al., All Your Base: a fast and accurate probabilistic approach to base calling, European Bioinformatics 18 Institute, 22 pages, [retrieved on Jul. 2, 2021], Retrieved from the internet [URL: https://www.ebi.ac.uk/goldman-srv/ AYB/references/ayb.pdf].
NL 2023310 NL Search Report, dated Mar. 5, 2020, 17 pages.
Python Implementation of the color map function for the PASCAL VOC data set. Github, 4 pages. Retrieved on Jul. 23, 2021. Retrieved from [URL: https://gist.github.com/wllf/a45330adebe573ed06d450c8419ae ].
Semantic Segmentation Examples—MATLAB and Simulink, 22 pages, (retrieved on Jul. 21, 2021], Retrieved from the Internet [URL: https://www.mathworks.com/help/vision/ug/semantic-segmentation-examples.html ].
Eraslan, G., Avsec, Ž., Gagneur, J. et al. Deep learning: new computational modelling techniques for genomics. Nature Reviews Genetic 20, 389-403 (2019). https://doi.org/10.1038/s41576-019-0122-6.
Chakradhar, Srimat T. et al. "A Dynamically Configurable Coprocessor for Convolutional Neural Networks". Proceedings of the 37th Annual International Symposium on Computer Architecture (2010): 247-257 (Year: 2010).
Huang, Neng et al. "An Attention-Based Neural Network Basecaller for Oxford Nanopore Sequencing Data". 2019 IEEE International Conference on Bioinformatics and Biomedicine (BIBM) (2019): 390-394. (Year: 2019).
Anonymous: "NovaSeq 6000—Sequencing System Guide", Feb. 1, 2019 (Feb. 1, 2019), XP055656862, Retrieved from the Internet: URL:https://support.illumina.com/content/dam/illumina-support/documents/documentation/system_documentation/novaseq/novaseq-6000-system-guide-1000000019358-11.pdf[retrieved on Jan. 10, 2020].

* cited by examiner

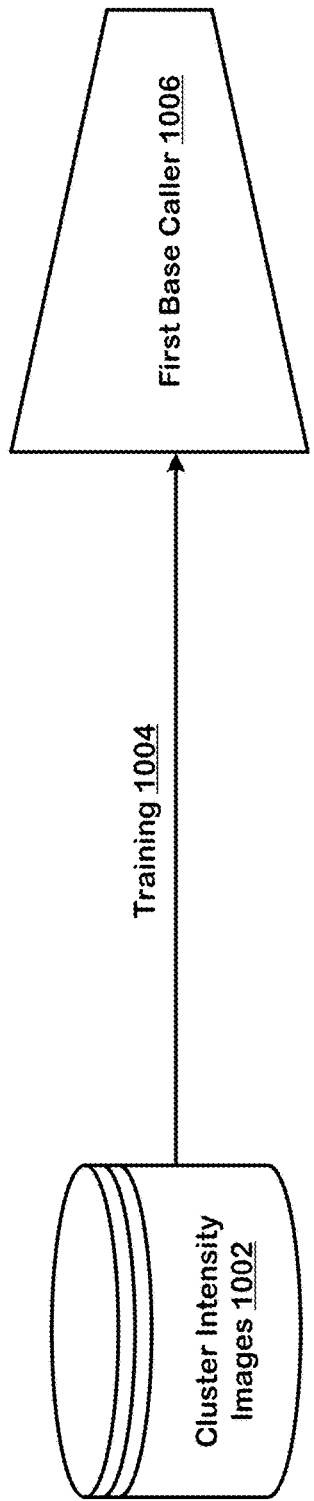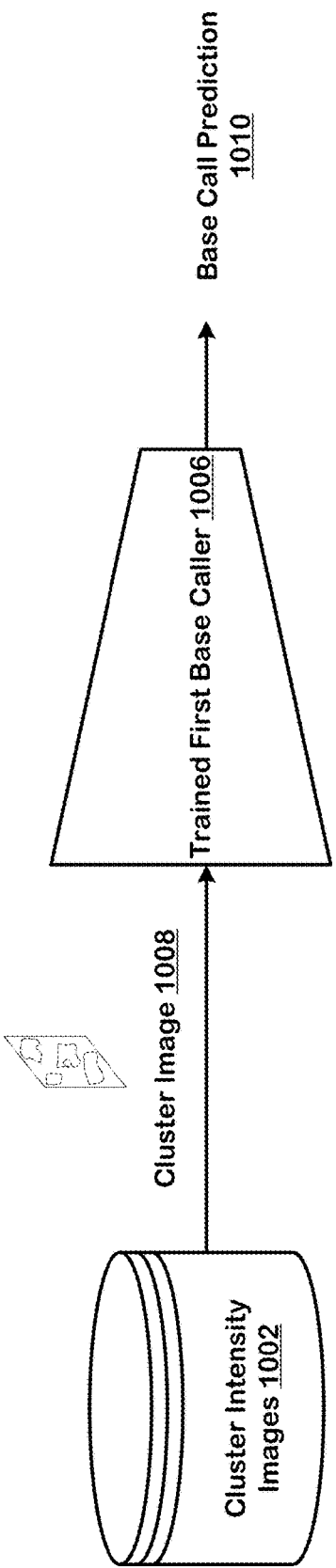

training a first base caller over cluster intensity images and producing a first trained base caller that maps the cluster intensity images to base call predictions 1402 beginning with the first trained base caller, executing a loop in which each iteration uses a starting trained base caller as input and produces a pruned trained base caller as output, wherein the pruned trained base caller has fewer processing elements than the starting trained base caller 1412 the cluster feature maps generation step, during forward propagation, processes a subset of the clusters intensity images through the processing elements of the starting trained base caller, generates one or more cluster feature maps using each processing element, and produces the base call predictions based on the cluster feature maps 1422 the contribution measurement step generates a contribution score for each of the cluster feature maps that identifies how much a cluster feature map contributed to the base call predictions 1432 the pruning step selects a subset of the cluster feature maps based on their contribution scores and produces the pruned trained base caller by removing, from the starting trained base caller, those processing elements that were used to generate the selected subset of the cluster feature maps during the forward propagation 1442 the retraining step further trains the pruned trained base caller over the cluster intensity images and makes the pruned trained base caller available for a successive iteration as the starting trained base caller 1452 terminating the loop after n iterations and using the pruned trained base caller produced by the nth iteration for further base calling 1462

FIG. 14

| Layer (type) | Output Shape | Param # |
|---|---|---|
| input_1 (InputLayer) | (None, 5, 115, 115, 4) | 0 |
| batch_normalization_1 (BatchNormalization) | (None, 5, 115, 115, 4) | 16 |
| conv3d_1 (Conv3D) | (None, 5, 113, 113, 64) | 2368 |
| batch_normalization_2 (BatchNormalization) | (None, 5, 113, 113, 64) | 256 |
| conv3d_2 (Conv3D) | (None, 5, 111, 111, 64) | 36928 |
| batch_normalization_3 (BatchNormalization) | (None, 5, 111, 111, 64) | 256 |
| conv3d_3 (Conv3D) | (None, 5, 109, 109, 64) | 36928 |
| batch_normalization_4 (BatchNormalization) | (None, 5, 109, 109, 64) | 256 |
| conv3d_4 (Conv3D) | (None, 5, 107, 107, 64) | 36928 |
| batch_normalization_5 (BatchNormalization) | (None, 5, 107, 107, 64) | 256 |
| conv3d_5 (Conv3D) | (None, 5, 105, 105, 64) | 36928 |
| batch_normalization_6 (BatchNormalization) | (None, 5, 105, 105, 64) | 256 |
| conv3d_6 (Conv3D) | (None, 5, 103, 103, 64) | 36928 |
| batch_normalization_7 (BatchNormalization) | (None, 5, 103, 103, 64) | 256 |
| conv3d_7 (Conv3D) | (None, 5, 101, 101, 64) | 36928 |
| batch_normalization_8 (BatchNormalization) | (None, 5, 101, 101, 64) | 256 |
| conv3d_8 (Conv3D) | (None, 3, 101, 101, 64) | 12352 |
| batch_normalization_9 (BatchNormalization) | (None, 3, 101, 101, 64) | 256 |
| conv3d_9 (Conv3D) | (None, 1, 101, 101, 64) | 12352 |
| batch_normalization_10 (BatchNormalization) | (None, 1, 101, 101, 64) | 256 |
| conv3d_10 (Conv3D) | (None, 1, 101, 101, 4) | 260 |
| activation_1 (Activation) | (None, 1, 101, 101, 4) | 0 |
| output0 (Reshape) | (None, 101, 101, 4) | 0 |

Total param : 251,220
Trainable params : 250,060
Non-trainable params : 1,160

FIG. 16

| Layer (type) | Output Shape | Param # |
| --- | --- | --- |
| input_1 (InputLayer) | (None, 5, 115, 115, 4) | 0 |
| batch_normalization_1 (BatchNormalization) | (None, 5, 115, 115, 4) | 16 |
| conv3d_1 (Conv3D) | (None, 5, 113, 113, 14) | 518 |
| batch_normalization_2 (BatchNormalization) | (None, 5, 113, 113, 14) | 56 |
| conv3d_2 (Conv3D) | (None, 5, 111, 111, 14) | 1778 |
| batch_normalization_3 (BatchNormalization) | (None, 5, 111, 111, 14) | 56 |
| conv3d_3 (Conv3D) | (None, 5, 109, 109, 14) | 1778 |
| batch_normalization_4 (BatchNormalization) | (None, 5, 109, 109, 14) | 56 |
| conv3d_4 (Conv3D) | (None, 5, 107, 107, 14) | 1778 |
| batch_normalization_5 (BatchNormalization) | (None, 5, 107, 107, 14) | 56 |
| conv3d_5 (Conv3D) | (None, 5, 105, 105, 14) | 1778 |
| batch_normalization_6 (BatchNormalization) | (None, 5, 105, 105, 14) | 56 |
| conv3d_6 (Conv3D) | (None, 5, 105, 105, 14) | 1778 |
| batch_normalization_7 (BatchNormalization) | (None, 5, 103, 103, 14) | 56 |
| conv3d_7 (Conv3D) | (None, 5, 101, 101, 14) | 1778 |
| batch_normalization_8 (BatchNormalization) | (None, 5, 101, 101, 14) | 56 |
| conv3d_8 (Conv3D) | (None, 3, 101, 101, 14) | 602 |
| batch_normalization_9 (BatchNormalization) | (None, 3, 101, 101, 14) | 56 |
| conv3d_9 (Conv3D) | (None, 1, 101, 101, 14) | 602 |
| batch_normalization_10 (BatchNormalization) | (None, 1, 101, 101, 14) | 56 |
| conv3d_10 (Conv3D) | (None, 1, 101, 101, 4) | 60 |
| activation_1 (Activation) | (None, 1, 101, 101, 4) | 0 |
| output0 (Reshape) | (None, 101, 101, 4) | 0 |

Total param : 251, 220
Trainable params : 250, 060
Non-trainable params : 1, 160

FIG. 17

KNOWLEDGE DISTILLATION AND GRADIENT PRUNING-BASED COMPRESSION OF ARTIFICIAL INTELLIGENCE-BASED BASE CALLER

PRIORITY APPLICATION

This application claims priority to and benefit of U.S. Provisional Patent Application No. 62/979,385, titled "KNOWLEDGE DISTILLATION-BASED COMPRESSION OF ARTIFICIAL INTELLIGENCE-BASED BASE CALLER," filed 20 Feb. 2020. The priority application is hereby incorporated by reference for all purposes as if fully set forth herein.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

INCORPORATIONS

The following are incorporated by reference as if fully set forth herein:
U.S. Provisional Patent Application No. 62/979,384, titled "ARTIFICIAL INTELLIGENCE-BASED BASE CALLING OF INDEX SEQUENCES," filed 20 Feb. 2020;
U.S. Provisional Patent Application No. 62/979,414, titled "ARTIFICIAL INTELLIGENCE-BASED MANY-TO-MANY BASE CALLING," filed 20 Feb. 2020;
U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020;
U.S. Provisional Patent Application No. 62/979,412, titled "MULTI-CYCLE CLUSTER BASED REAL TIME ANALYSIS SYSTEM," filed 20 Feb. 2020;
U.S. Provisional Patent Application No. 62/979,411, titled "DATA COMPRESSION FOR ARTIFICIAL INTELLIGENCE-BASED BASE CALLING," filed 20 Feb. 2020;
U.S. Provisional Patent Application No. 62/979,399, titled "SQUEEZING LAYER FOR ARTIFICIAL INTELLIGENCE-BASED BASE CALLING," filed 20 Feb. 2020;
U.S. Nonprovisional patent application Ser. No. 16/825,987, titled "TRAINING DATA GENERATION FOR ARTIFICIAL INTELLIGENCE-BASED SEQUENCING," filed 20 Mar. 2020;
U.S. Nonprovisional patent application Ser. No. 16/825,991 titled "ARTIFICIAL INTELLIGENCE-BASED GENERATION OF SEQUENCING METADATA," filed 20 Mar. 2020;
U.S. Nonprovisional patent application Ser. No. 16/826,126, titled "ARTIFICIAL INTELLIGENCE-BASED BASE CALLING," filed 20 Mar. 2020;
U.S. Nonprovisional patent application Ser. No. 16/826,134, titled "ARTIFICIAL INTELLIGENCE-BASED QUALITY SCORING," filed 20 Mar. 2020; and
U.S. Nonprovisional patent application Ser. No. 16/826,168, titled "ARTIFICIAL INTELLIGENCE-BASED SEQUENCING," filed 21 Mar. 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

In order to deploy efficient deep neural networks on mobile devices, academia and industry have put forward a number of model compression methods. The compression methods can be broadly classified into four categories: parameter sharing, network pruning, low-rank factorization, and knowledge distillation. In knowledge distillation, the knowledge embedded in the cumbersome model, known as the teacher model, is distilled to guide the training of a smaller model called the student model. The student model has a different architecture and fewer parameters but can achieve comparable performance by mimicking the behavior of the cumbersome model. Other compression methods like quantization and low-rank factorization are complementary to knowledge distillation and can also be used to further reduce the size of student models.

An opportunity arises to accelerate artificial intelligence-based base calling using knowledge distillation.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 10A shows one implementation of training a first base caller over cluster intensity images and producing a first trained base caller. FIG. 10B shows one implementation of the first trained base caller mapping the cluster intensity images to base call predictions.

FIG. 14 shows another implementation of an artificial intelligence-based method of performing computationally efficient base calling.

FIG. 16 shows one implementation of a larger, teacher base caller with 251,220 total parameters.

FIG. 17 shows one implementation of a smaller, student base caller with 12,970 total parameters that is distilled from the larger, teacher base caller of FIG. 16 using the technology disclosed.

DETAILED DESCRIPTION

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

INTRODUCTION

The technology disclosed compresses a larger, teacher base caller into a smaller, distilled student base caller. The student base caller has fewer processing modules and parameters than the teacher base caller. The larger, teacher base caller can comprise an ensemble of larger, teacher base callers. The teacher base caller is trained using hard labels (e.g., one-hot encodings). The trained teacher base caller is used to generate soft labels as output probabilities during the inference phase. The soft labels are used to train the student base caller.

A hard label is a one-hot vector where all entries are set to zero aside from a single entry, the one corresponding to the correct class, which is set to one. In contrast, the soft labels form a probability distribution over the possible classes. The idea is that a cluster image contains information about more than one class (e.g., a cluster image of the base call "A" looks a lot like other cluster images of base call "A," but it also looks like some cluster images of the base call "C"). Using soft labels allows us to convey more information about the associated cluster image, which is particularly useful in detecting boundaries between clusters in a cluster image.

This application refers to the teacher base caller as the first base caller, the bigger engine, and the bigger model. This application refers to the student base caller as the second base caller, the smaller engine, and the smaller model. This application refers to the hard labels as discrete valued labels. This application refers to the soft labels as continuous valued weights. The student base caller can be used for executing the sequencing run in an online model where base calls are generated in real-time on a cycle-by-cycle basis such as that the student base caller processes incoming images for a current sequencing cycle, generates base calls for the current sequencing cycle, processes incoming images for a next sequencing cycle, generates base calls for the next sequencing cycle, and so on.

Base Callers

Figure 7:
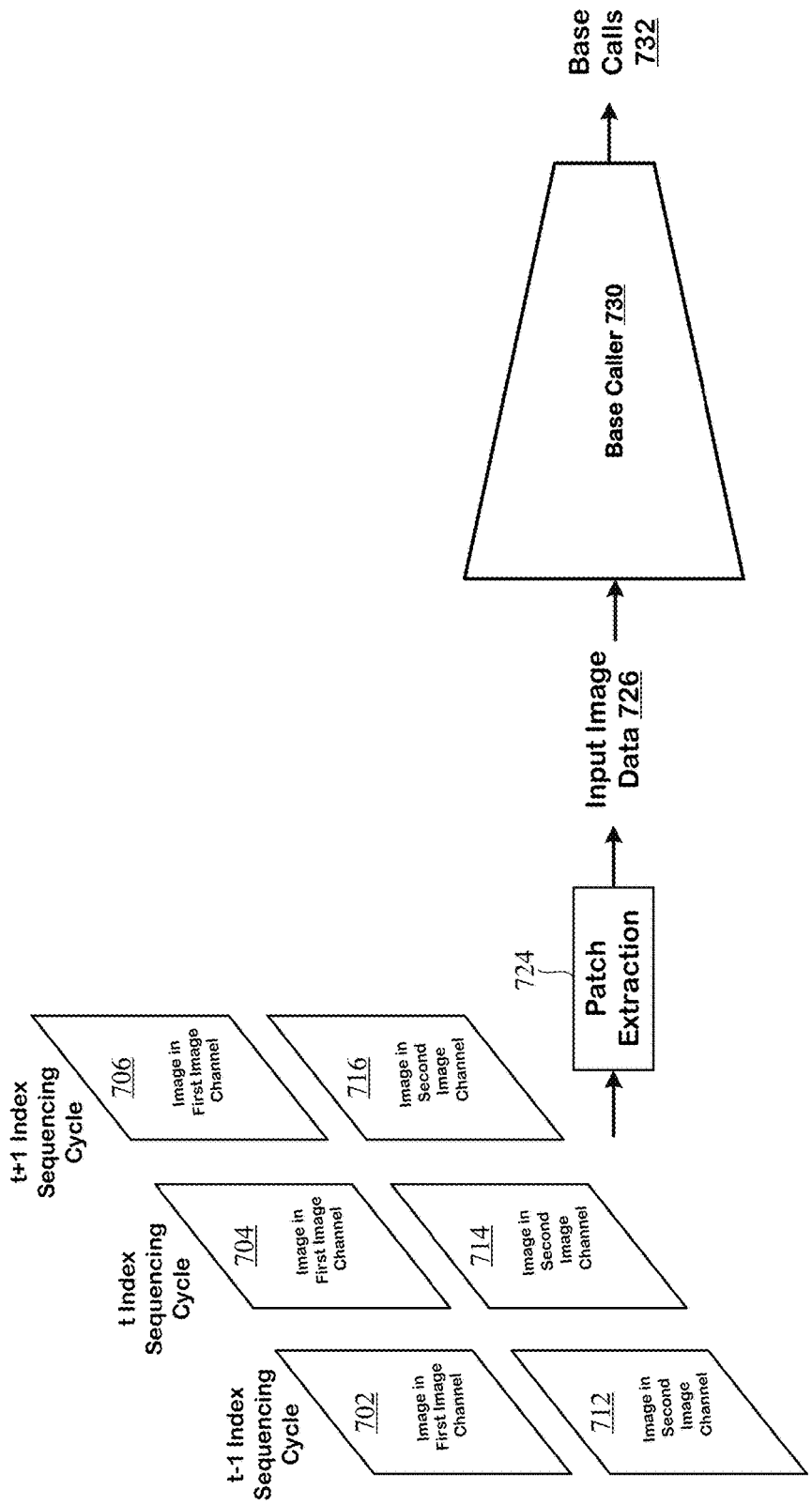
FIG. 7 illustrates one implementation of data processing by the teacher and student base callers.

The discussion begins with data processing by the teacher base caller 110 and the student base caller 124, which are trained to map sequencing images to base calls. In FIG. 7, for purposes of illustration of the data processing, base caller 730 is representative of both the teacher base caller 110 and the student base caller 124; however, the student base caller 124 has fewer processing modules and parameters than the teacher base caller 110. In one implementation, one of the processing modules is neural network layers. In one implementation, one of the parameters is interconnections between the neural network layers. In one implementation, one of the processing modules is neural network filters. In one implementation, one of the processing modules is neural network kernels. In one implementation, one of the parameters is multiplication and addition operations.

Base calling is the process of determining the nucleotide composition of a sequence. Base calling involves analyzing image data, i.e., sequencing images produced during the sequencing reaction carried out by a sequencing instrument such as Illumina's iSeq, HiSeqX, HiSeq 3000, HiSeq 4000, HiSeq 2500, NovaSeq 6000, NextSeq, NextSeqDx, MiSeq, and MiSeqDx. The following discussion outlines how the sequencing images are generated and what they depict, in accordance with one implementation.

Base calling decodes the raw signal of the sequencing instrument, i.e., intensity data extracted from the sequencing images, into nucleotide sequences. In one implementation, the Illumina platforms employ cyclic reversible termination (CRT) chemistry for base calling. The process relies on growing nascent strands complementary to template strands with fluorescently-labeled nucleotides, while tracking the emitted signal of each newly added nucleotide. The fluorescently-labeled nucleotides have a 3' removable block that anchors a fluorophore signal of the nucleotide type.

Sequencing occurs in repetitive cycles, each comprising three steps: (a) extension of a nascent strand by adding the fluorescently-labeled nucleotide; (b) excitation of the fluorophore using one or more lasers of an optical system of the sequencing instrument and imaging through different filters of the optical system, yielding the sequencing images; and (c) cleavage of the fluorophore and removal of 3' block in preparation for the next sequencing cycle. Incorporation and imaging cycles are repeated up to a designated number of sequencing cycles, defining the read length. Using this approach, each cycle interrogates a new position along the template strands.

The tremendous power of the Illumina platforms stems from their ability to simultaneously execute and sense millions or even billions of analytes (e.g., clusters) undergoing CRT reactions. A cluster comprises approximately one thousand identical copies of a template strand, though clusters vary in size and shape. The clusters are grown from the template strand, prior to the sequencing run, by bridge amplification of the input library. The purpose of the amplification and cluster growth is to increase the intensity of the emitted signal since the imaging device cannot reliably sense fluorophore signal of a single strand. However, the physical distance of the strands within a cluster is small, so the imaging device perceives the cluster of strands as a single spot.

Sequencing occurs in a flow cell—a small glass slide that holds the input strands. The flow cell is connected to the optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. The imaging device of the sequencing instrument (e.g., a solid-state imager such as a charge-coupled device (CCD) or a complementary metal-oxide-semiconductor (CMOS) sensor) takes snapshots at multiple locations along the lanes in a series of non-overlapping regions called tiles. For example, there are hundred tiles per lane in Illumina's Genome Analyzer II and sixty-eight tiles per lane in Illumina's HiSeq 2000. A tile holds hundreds of thousands to millions of clusters.

The output of the sequencing is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background.

The following discussion is organized as follows. First, the input to the base caller 730 is described, in accordance with one implementation. Then, examples of the structure and form of the base caller 730 are provided. Finally, the output of the base caller 730 is described, in accordance with one implementation.

Additional details about the base caller 730 can be found in U.S. Provisional Patent Application No. 62/821,766, titled "ARTIFICIAL INTELLIGENCE-BASED SEQUENCING,", filed on Mar. 21, 2019, which is incorporated herein by reference.

In one implementation, image patches are extracted from the sequencing images. The extracted image patches are provided to the base caller 730 as "input image data" 726 for base calling. The image patches have dimensions w×h, where w (width) and h (height) are any numbers ranging from 1 and 10,000 (e.g., 3×3, 5×5, 7×7, 10×10, 15×15, 25×25). In some implementations, w and h are the same. In other implementations, w and h are different.

Sequencing produces m image(s) per sequencing cycle for corresponding m image channels. In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter.

An image patch is extracted from each of the m image(s) to prepare the input image data 726 for a particular sequencing cycle. In different implementations such as 4-, 2-, and 1-channel chemistries, m is 4 or 2. In other implementations, m is 1, 3, or greater than 4. The input image data 726 is in the optical, pixel domain in some implementations, and in the upsampled, subpixel domain in other implementations.

Consider, for example, that sequencing uses two different image channels: a red channel and a green channel. Then, at each sequencing cycle, sequencing produces a red image and a green image. This way, for a series of k sequencing cycle, a sequence with k pairs of red and green images is produced as output.

The input image data 726 comprises a sequence of per-cycle image patches generated for a series of k sequencing cycles of a sequencing run. The per-cycle image patches contain intensity data for associated analytes and their surrounding background in one or more image channels (e.g., a red channel and a green channel). In one implementation, when a single target analyte (e.g., cluster) is to be base called, the per-cycle image patches are centered at a center pixel that contains intensity data for a target associated analyte and non-center pixels in the per-cycle image patches contain intensity data for associated analytes adjacent to the target associated analyte.

The input image data 726 comprises data for multiple sequencing cycles (e.g., a current sequencing cycle, one or more preceding sequencing cycles, and one or more successive sequencing cycles). In one implementation, the input image data 726 comprises data for three sequencing cycles, such that data for a current (time t) sequencing cycle to be base called is accompanied with (i) data for a left flanking/ context/previous/preceding/prior (time t−1) sequencing cycle and (ii) data for a right flanking/context/next/successive/subsequent (time t+1) sequencing cycle. In other implementations, the input image data 726 comprises data for a single sequencing cycle. In yet other implementations, the input image data 726 comprises data for 58, 75, 92, 130, 168, 175, 209, 225, 230, 275, 318, 325, 330, 525, or 625 sequencing cycles.

In one implementation, the base caller 730 is a multilayer perceptron (MLP). In another implementation, the base caller 730 is a feedforward neural network. In yet another implementation, the base caller 730 is a fully-connected neural network. In a further implementation, the base caller 730 is a fully convolutional neural network. In yet further implementation, the base caller 730 is a semantic segmentation neural network. In yet another further implementation, the base caller 730 is a generative adversarial network (GAN).

In one implementation, the base caller 730 is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the base caller 730 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

In one implementation, the base caller 730 outputs a base call for a single target analyte for a particular sequencing cycle. In another implementation, it outputs a base call for each target analyte in a plurality of target analytes for the particular sequencing cycle. In yet another implementation, it outputs a base call for each target analyte in a plurality of target analytes for each sequencing cycle in a plurality of sequencing cycles, thereby producing a base call sequence for each target analyte.

In one implementation, the sequencing images 704, 714 from the current (time t) sequencing cycle are accompanied with the sequencing images 702, 712 from the preceding (time t−1) sequencing cycle and the sequencing images 706, 716 from the succeeding (time t+1) sequencing cycle. The base caller 730 processes the sequencing images 702, 712, 704, 714, 706, and 716 through its convolution layers and produces an alternative representation, according to one implementation. The alternative representation is then used by an output layer (e.g., a softmax layer) for generating a base call for either just the current (time t) sequencing cycle or each of the sequencing cycles, i.e., the current (time t) sequencing cycle, the preceding (time t−1) sequencing cycle, and the succeeding (time t+1) sequencing cycle. The resulting base calls 732 form the sequencing reads.

In one implementation, a patch extraction process 724 extracts patches from the sequencing images 702, 712, 704, 714, 706, and 716 and generates the input image data 726. Then, the extracted images patches in the input image data 726 are provided to the base caller 730 as input.

The teacher base caller 110 and the student base caller 124 are trained using backpropagation-based gradient update techniques. Some types of gradient descent techniques that can be used for training the teacher base caller 110 and the student base caller 124 are stochastic gradient descent, batch gradient descent, and mini-batch gradient descent. Some examples of gradient descent optimization algorithms that can be used for training the teacher base caller 110 and the student base caller 124 are Momentum, Nesterov accelerated gradient, Adagrad, Adadelta, RMSprop, Adam, AdaMax, Nadam, and AMSGrad.

Knowledge Distillation

Figure 1:
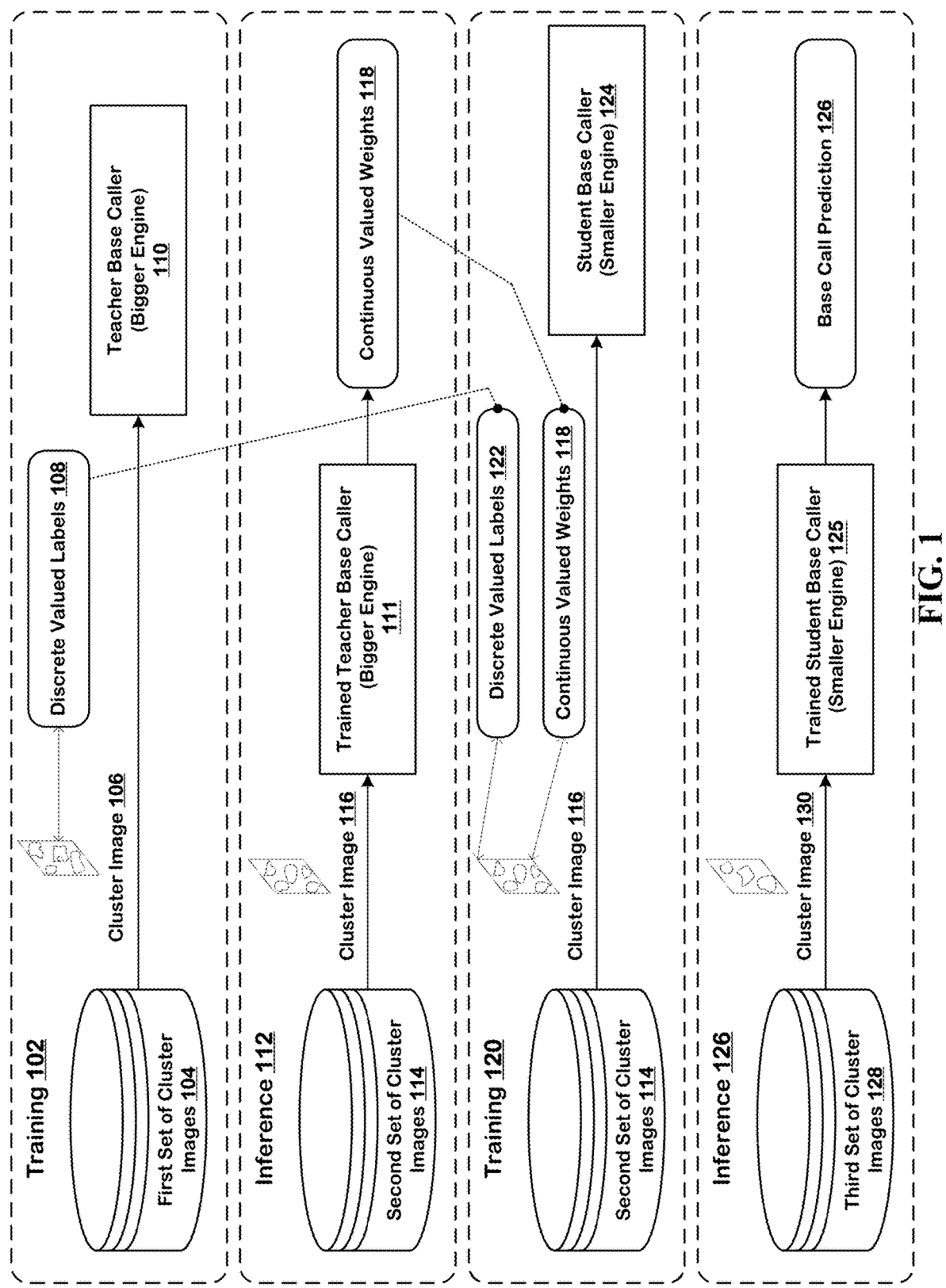
FIG. 1 illustrates various aspects of using the disclosed knowledge distillation for artificial intelligence-based base calling.

FIG. 1 illustrates various aspects of using the disclosed knowledge distillation for artificial intelligence-based base calling. The disclosed knowledge distillation comprises:

Training the teacher base caller on training data using "hard labels"

Generating "soft labels" by applying the trained teacher base caller on inference data Training the student base caller on training data using a "combination" of the hard and soft labels, i.e., "hybrid" ground truth data The student base caller 124 has fewer processing modules and parameters than the teacher base caller 110. In one implementation, one of the processing modules is neural network layers. In one implementation, one of the parameters is interconnections between the neural network layers. In one implementation, one of the processing modules is neural network filters. In one implementation, one of the processing modules is neural network kernels. In one implementation, one of the parameters is multiplication and addition operations.

Training the Teacher Base Caller

During training 102, the teacher base caller 110 is trained on training data comprising a first set of cluster images 104. The first set of cluster images 104 are annotated with ground truth data that uses discrete valued labels 108.

In one implementation, a cluster image 106 is annotated with the discrete valued labels 108 that are one-hot encoded with a one-value for a correct base and zero-values for incorrect bases. The following is an example of one-hot encoding for the four nucleotide bases:

A 1
C 0
T 0
G 0

Figure 2A:
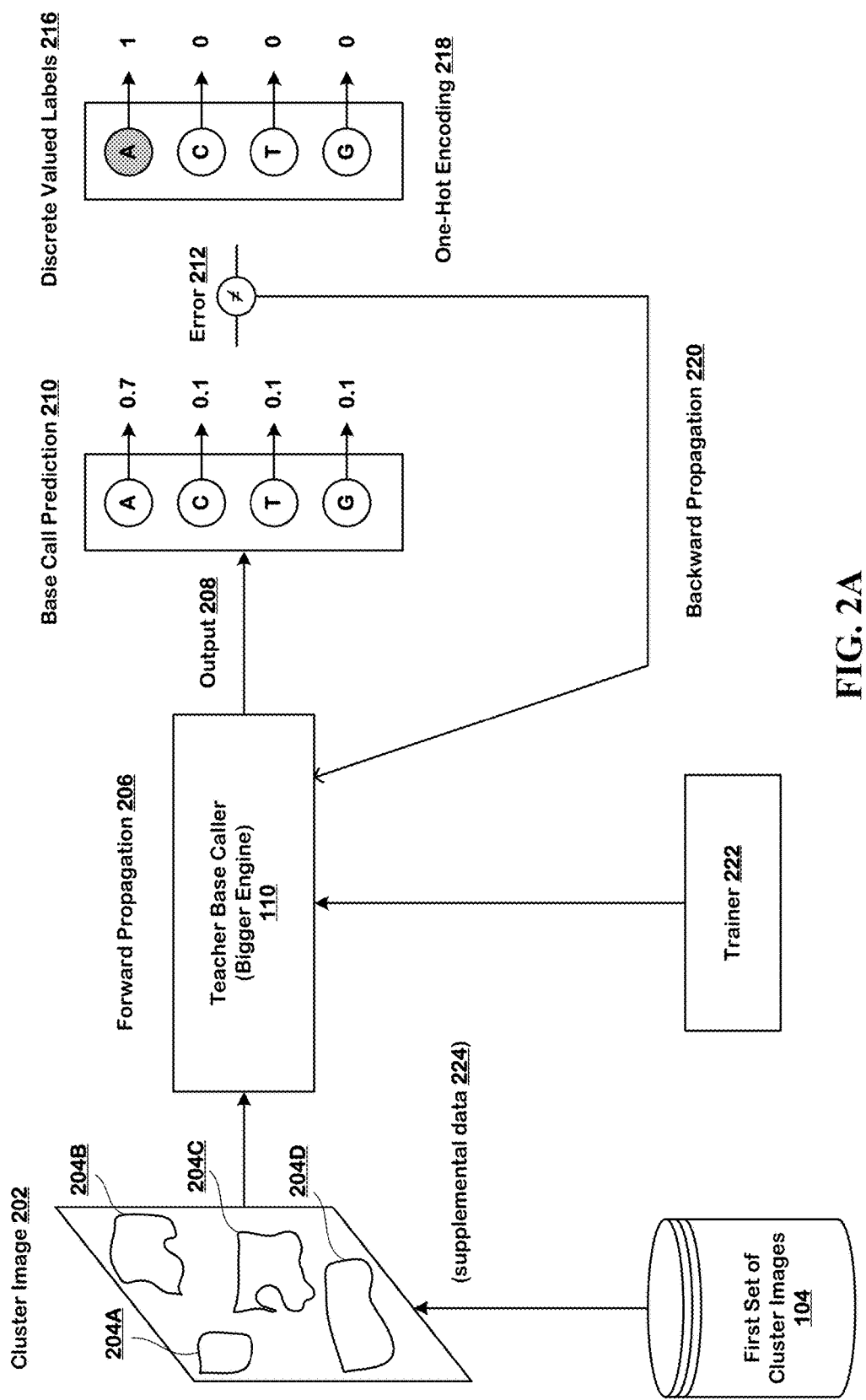
FIG. 2A depicts one implementation of training a teacher base caller by using a first set of cluster images that are annotated with first ground truth data which uses discrete valued labels (one-hot encoding) to identify a correct base call.

FIG. 2A depicts one implementation of training 200A the teacher base caller 110 by using the first set of cluster images 104 that are annotated with first ground truth data 214 which uses discrete valued labels 216 (one-hot encoding 218) to identify a correct base call. During forward propagation 206, the input to the teacher base caller 110 is a cluster image 202 that depicts intensities of clusters 204A, 204B, 204C, and 204D and their surrounding background.

In one implementation, the cluster image 202 is accompanied with supplemental data 224 such as a distance channel and a scaling channel. Additional details about the supplemental data 224 can be found in U.S. Provisional Patent Application No. 62/821,766, titled "ARTIFICIAL INTELLIGENCE-BASED SEQUENCING,", which is incorporated herein by reference.

In response to processing the cluster image 202, the teacher base caller 110 produces an output 208. Based on the output 208, a base call prediction 210 is made that identifies confidence scores assigned by the teacher base caller 110 to each of the bases A, C, T, and G.

Then, an error 212 is computed between the base call prediction 210 and the discrete valued labels 216, e.g., one-hot encoding 218, i.e., [1, 0, 0, 0]. Backward propagation 220 updates weights and parameters of the teacher base caller 110 based on the error 212.

This process is iterated until the teacher base caller 110 converges to a desired base call accuracy on a validation dataset. The training is operationalized (implemented) by a trainer 222 using backpropagation-based gradient update techniques (such as the ones discussed above).

In another implementation, the cluster image 106 is annotated with the discrete valued labels 108 that have a near-one-value for the correct base and near-zero-values for the incorrect bases, referred to herein as "softened one-hot encoding." The following is an example of softened one-hot encoding for the four nucleotide bases:

A 0.95
C 0.02
T 0.017
G 0.013

Figure 2B:
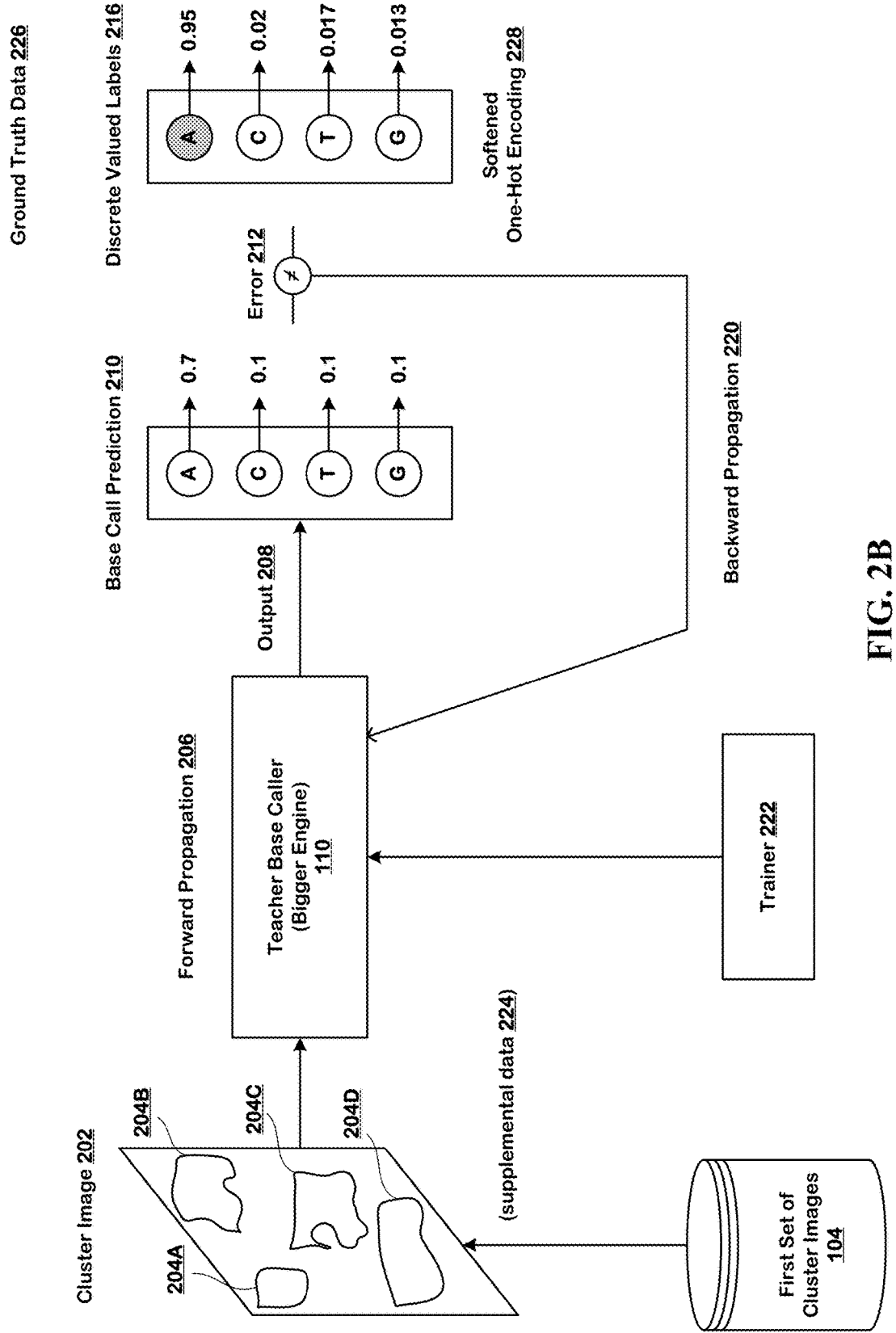
FIG. 2B depicts another implementation of training the teacher base caller by using the first set of cluster images that are annotated with the first ground truth data which uses the discrete valued labels (softened one-hot encoding) to identify the correct base call.

FIG. 2B depicts another implementation of training 200B the teacher base caller 110 by using the first set of cluster images 104 that are annotated with the first ground truth data 226 which uses the discrete valued labels 216 (softened one-hot encoding 228) to identify the correct base call. Here, the error 212 is computed between the base call prediction 210 and the softened one-hot encoding 228, i.e., [0.95, 0.02, 0.017, 0.013].

Generating Soft Labels

During inference 112, the trained teacher base caller 111 is applied on inference data comprising a second set of cluster images 114. The trained teacher base caller 111 processes the second set of cluster images 114 and generates base call predictions as output. The base call predictions are represented by continuous valued weights 118 (soft labels) that identify a predicted base call. The continuous valued weights 118 are part of a probability distribution for a correct base being Adenine (A), Cytosine (C), Thymine (T), and Guanine (G). In one implementation, the continuous valued weights 118 are softmax scores, i.e., posterior probabilities.

In one implementation, a cluster image 116 is fed as input to the trained teacher base caller 111. In response, the trained teacher base caller 111 generates exponentially normalized likelihood of a base incorporated in a cluster depicted by the cluster image 116 at a current sequencing cycle being A, C, T, and G.

The following is an example of the continuous valued weights 118:

A 0.175
C 0.024
T 0.475
G 0.326

Figure 3:
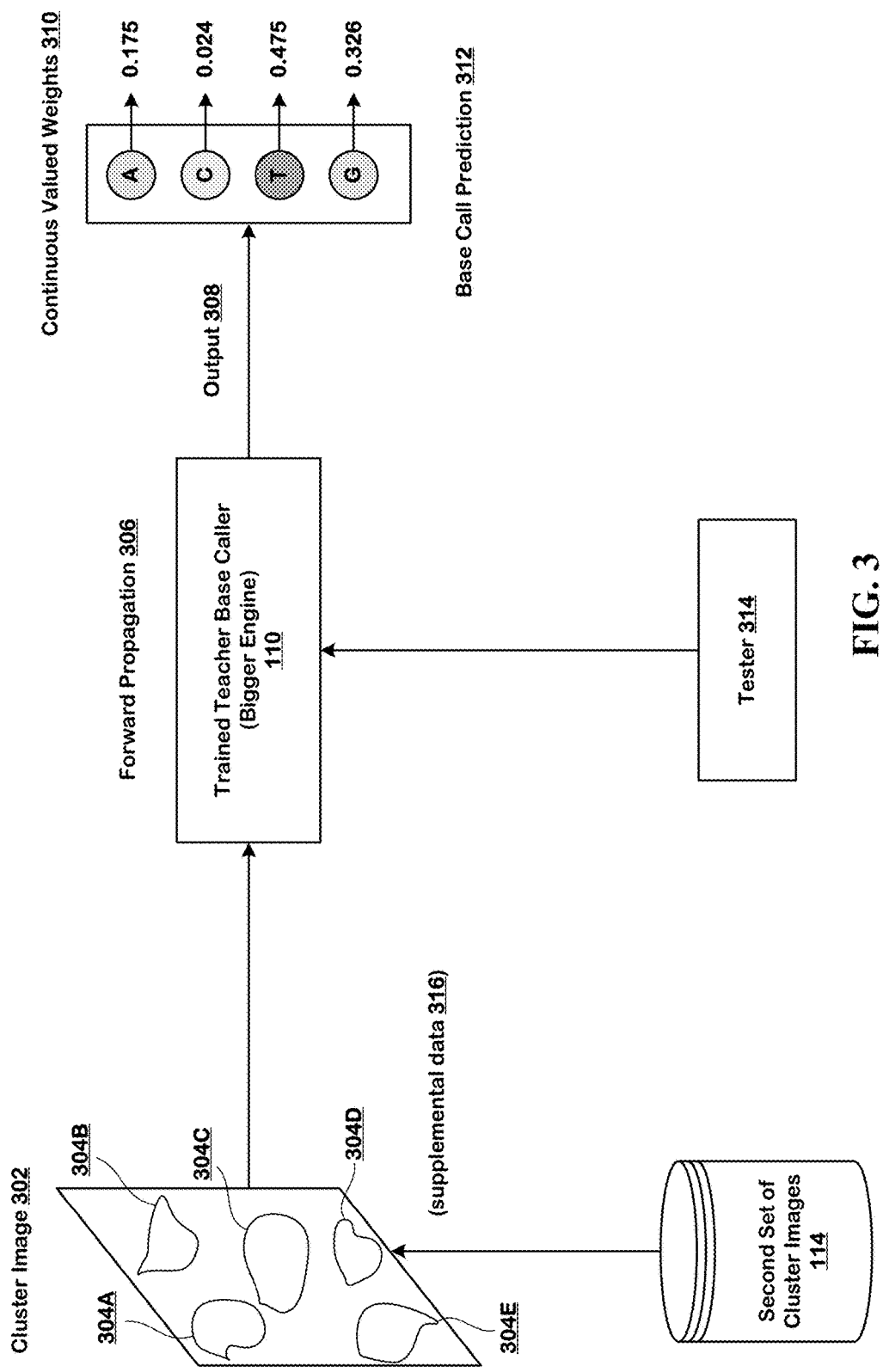
FIG. 3 shows one implementation of applying the trained teacher base caller on a second set of cluster images and generating base call predictions that are represented by continuous valued weights.

FIG. 3 shows one implementation of applying 300 the trained teacher base caller 111 on the second set of cluster images 114 and generating a base call prediction 312 that is represented by the continuous valued weights 310. During forward propagation 306, the input to the trained teacher base caller 111 is a cluster image 302 that depicts intensities of clusters 304A, 304B, 304C, 304D, and 304E and their surrounding background. In one implementation, the cluster image 302 is accompanied with supplemental data 316 such as the distance channel and the scaling channel.

In response to processing the cluster image 302, the trained teacher base caller 111 produces an output 308. Based on the output 308, the base call prediction 312 is generated that identifies confidence scores assigned by the trained teacher base caller 111 to each of the bases A (0.175), C (0.024), T (0.475), and G (0.326). These confidence scores are represented as continuous values, i.e., the continuous valued weights 310.

This process is iterated over numerous images in the second set of cluster images 114, such that a set of continuous valued weights is generated for each evaluated cluster image. The evaluation is operationalized (implemented) by a tester 314.

Generating Hybrid Ground Truth Data

Figure 4A:
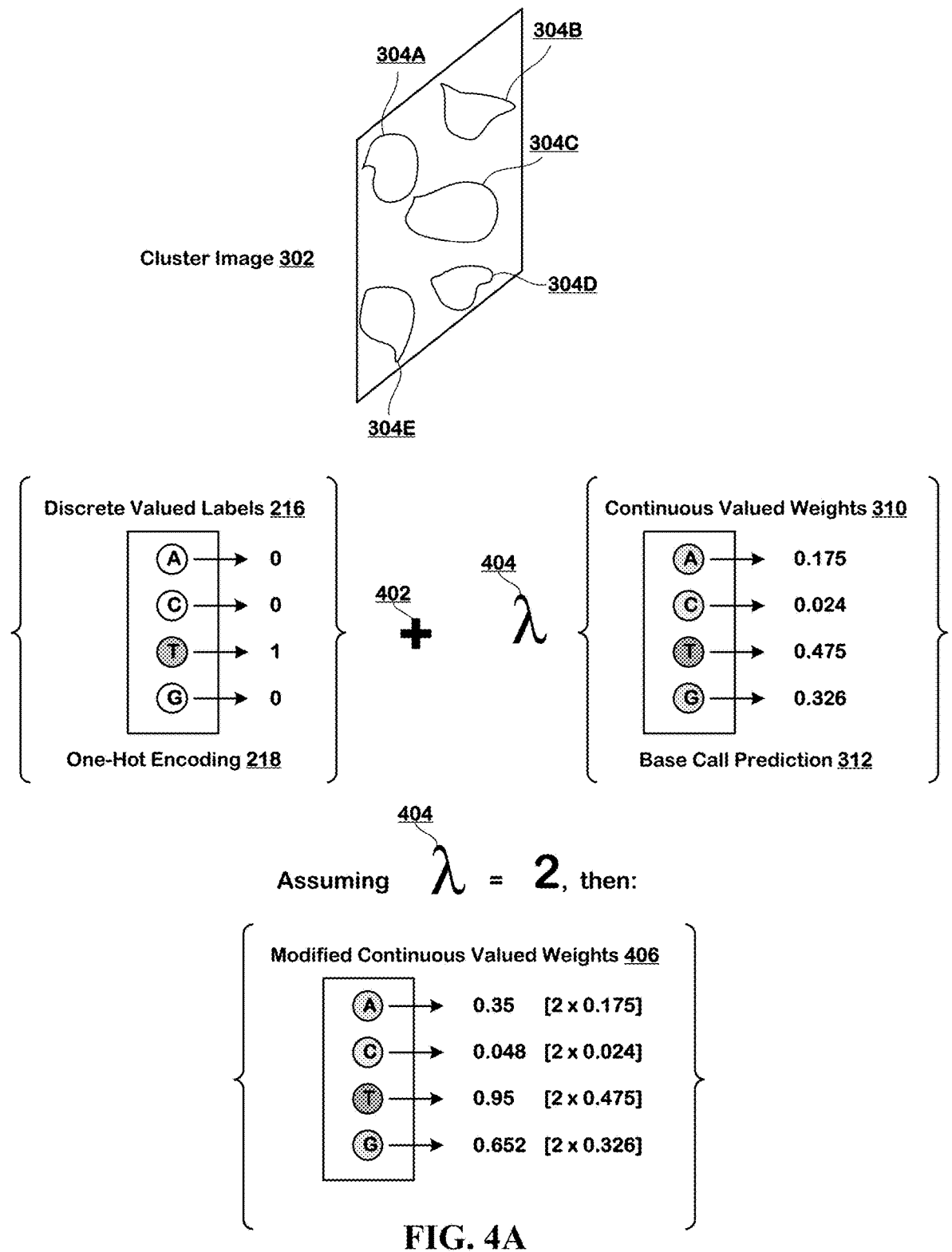
FIGS. 4A and 4B illustrate one implementation of so-called "hybrid ground truth data" generation using a combination of the discrete valued labels and the continuous valued weights.
Figure 4B:
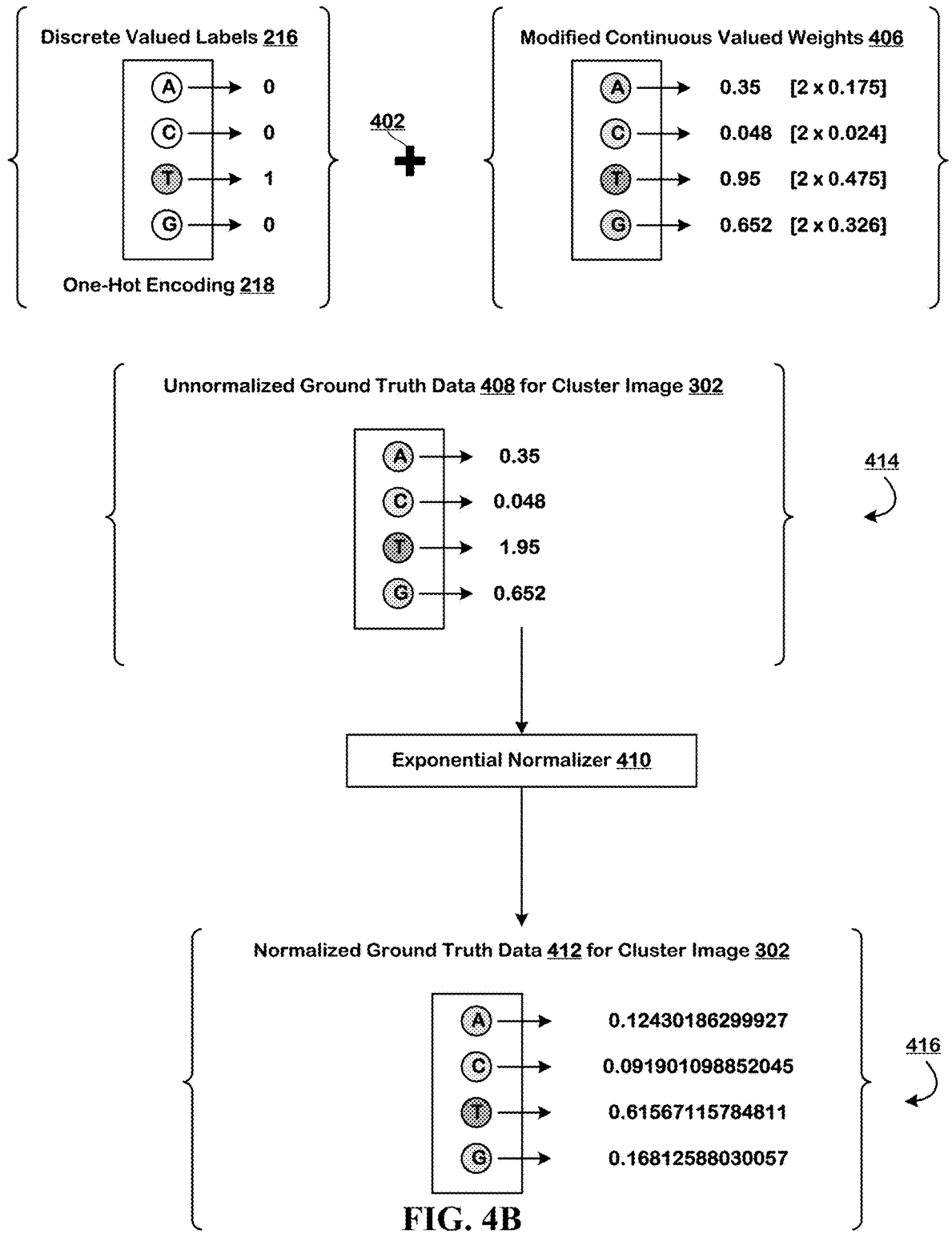

FIGS. 4A and 4B illustrate one implementation of so-called "hybrid ground truth data" generation 400A and 400B using a combination of the discrete valued labels 216 and the continuous valued weights 310.

In one implementation, the discrete valued labels 216 and the continuous valued weights 310 are accessed for a same cluster image 302 and combined to generate hybrid ground truth data for the cluster image 302. In some implementations, the discrete valued labels 216 are summed 402 with the continuous valued weights 310. In other implementations, the discrete valued labels 216 are multiplied with the continuous valued weights 310. In some other implementations, the discrete valued labels 216 are concatenated with the continuous valued weights 310.

In one implementation, the discrete valued labels 216 and the continuous valued weights 310 are combined on classwise basis. That is, discrete valued label for base call A is summed, multiplied, or concatenated with continuous valued weight for base call A, discrete valued label for base call C is summed, multiplied, or concatenated with continuous valued weight for base call C, discrete valued label for base call T is summed, multiplied, or concatenated with continuous valued weight for base call T, and discrete valued label for base call G is summed, multiplied, or concatenated with continuous valued weight for base call G.

In some implementations, prior to being combined with the discrete valued labels 216, the continuous valued weights 310 are modified using a modification parameter ($\lambda$) 404. In one implementation, the modification parameter ($\lambda$) 404 is iteratively learned based on performance of the student base caller 124 over a validation dataset. After the modification parameter ($\lambda$) 404 is applied on the continuous valued weights 310, what results is modified continuous valued weights 406.

In one implementation, the discrete valued labels 216 are combined with the modified continuous valued weights 406 to produce unnormalized ground truth data 408 for the cluster image 302. The unnormalized ground truth data 408 is then normalized to produce normalized ground truth data 412 for the cluster image 302. In some implementations, an exponential normalizer 410 (e.g., softmax) is used to produce the normalized ground truth data 412.

In one implementation, the unnormalized ground truth data 408 is considered the hybrid ground truth data 414 for the cluster image 302. In another implementation, the normalized ground truth data 412 is considered the hybrid ground truth data 416 for the cluster image 302.

Training the Student Base Caller

During training 120, the student base caller 124 is trained on training data comprising the second set of cluster images 114. The second set of cluster images 114 are annotated with ground truth data 414/416 that identifies a correct base call based on (i) the discrete valued labels 122 and (ii) the continuous valued weights 118.

Figure 5:
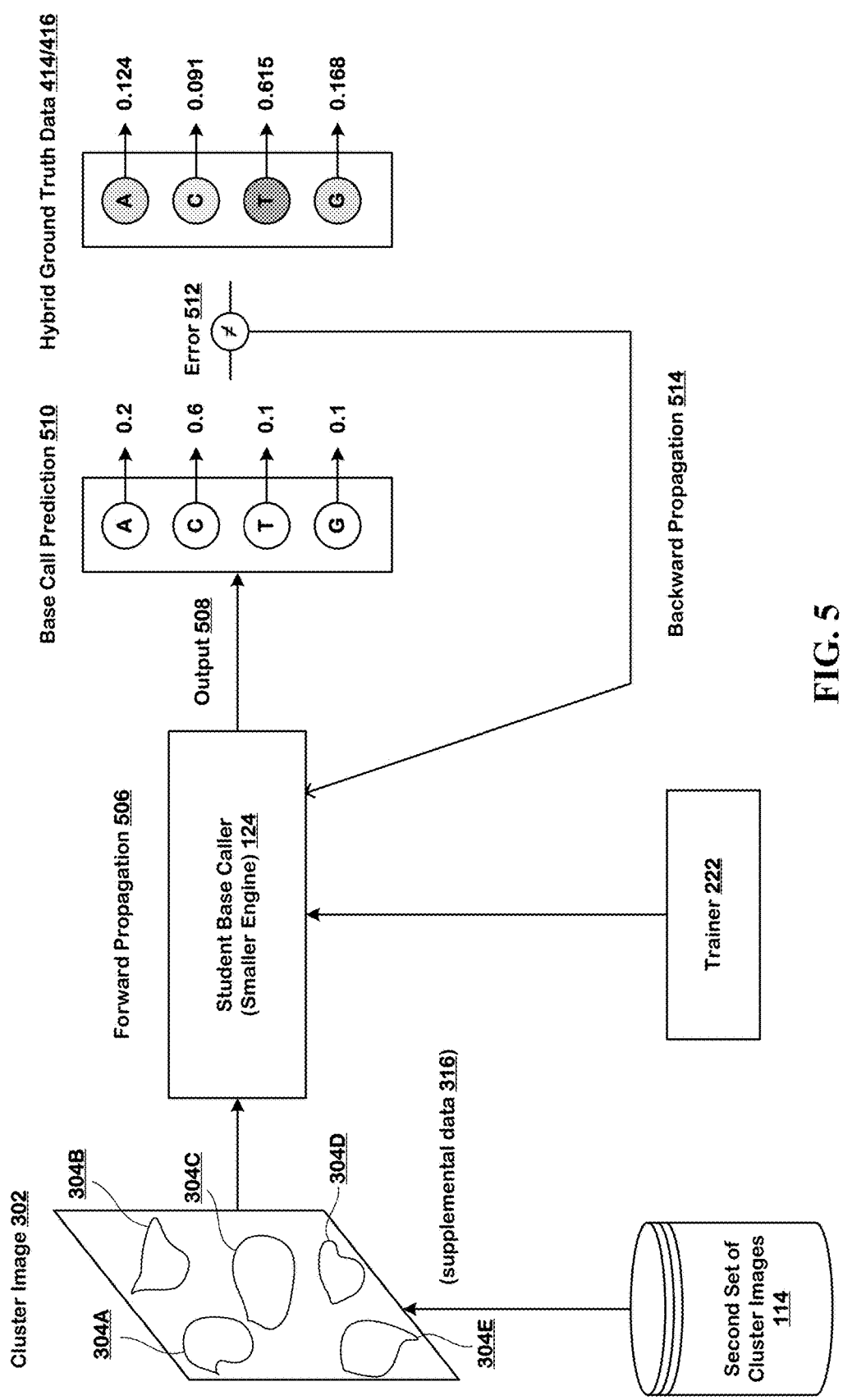
FIG. 5 is one implementation of training the student base caller using the second set of cluster images that are annotated with the hybrid ground truth data which identifies a correct base call based on the discrete valued labels and the continuous valued weights.

FIG. 5 is one implementation of training the student base caller 124 using the second set of cluster images 114 that are annotated with the hybrid ground truth data 414/416 which identifies a correct base call based on the discrete valued labels 216 and the continuous valued weights 310. During forward propagation 506, the input to the student base caller 124 is the cluster image 302 that depicts intensities of clusters 304A, 304B, 304C, 304D, and 304E and their surrounding background. In one implementation, the cluster image 302 is accompanied with supplemental data 316 such as the distance channel and the scaling channel.

In response to processing the cluster image 302, the student base caller 124 produces an output 508. Based on the output 508, a base call prediction 510 is made that identifies confidence scores assigned by the student base caller 124 to each of the bases A, C, T, and G.

Then, an error 512 is computed between the base call prediction 510 and the hybrid ground truth data 414/416. Backward propagation 514 updates weights and parameters of the student base caller 124 based on the error 512.

This process is iterated until the student base caller 124 converges to a desired base call accuracy on a validation dataset. The training is operationalized (implemented) by the trainer 222 using backpropagation-based gradient update techniques (such as the ones discussed above).

Applying the Trained Student Base Caller

During inference 126, the trained student base caller 124 is applied on inference data comprising a third set of cluster images 128. The trained student base caller 124 processes the third set of cluster images 128 and generates base call predictions 126 as output.

During inference 126, the trained student base caller 125 is applied on inference data comprising a third set of cluster images 128. The trained student base caller 125 processes the third set of cluster images 128 and generates base call predictions 126 as output.

In one implementation, a cluster image 130 is fed as input to the trained student base caller 125. In response, the trained student base caller 125 generates exponentially normalized likelihood of a base incorporated in a cluster depicted by the cluster image 130 at a current sequencing cycle being A, C, T, and G.

Figure 6:
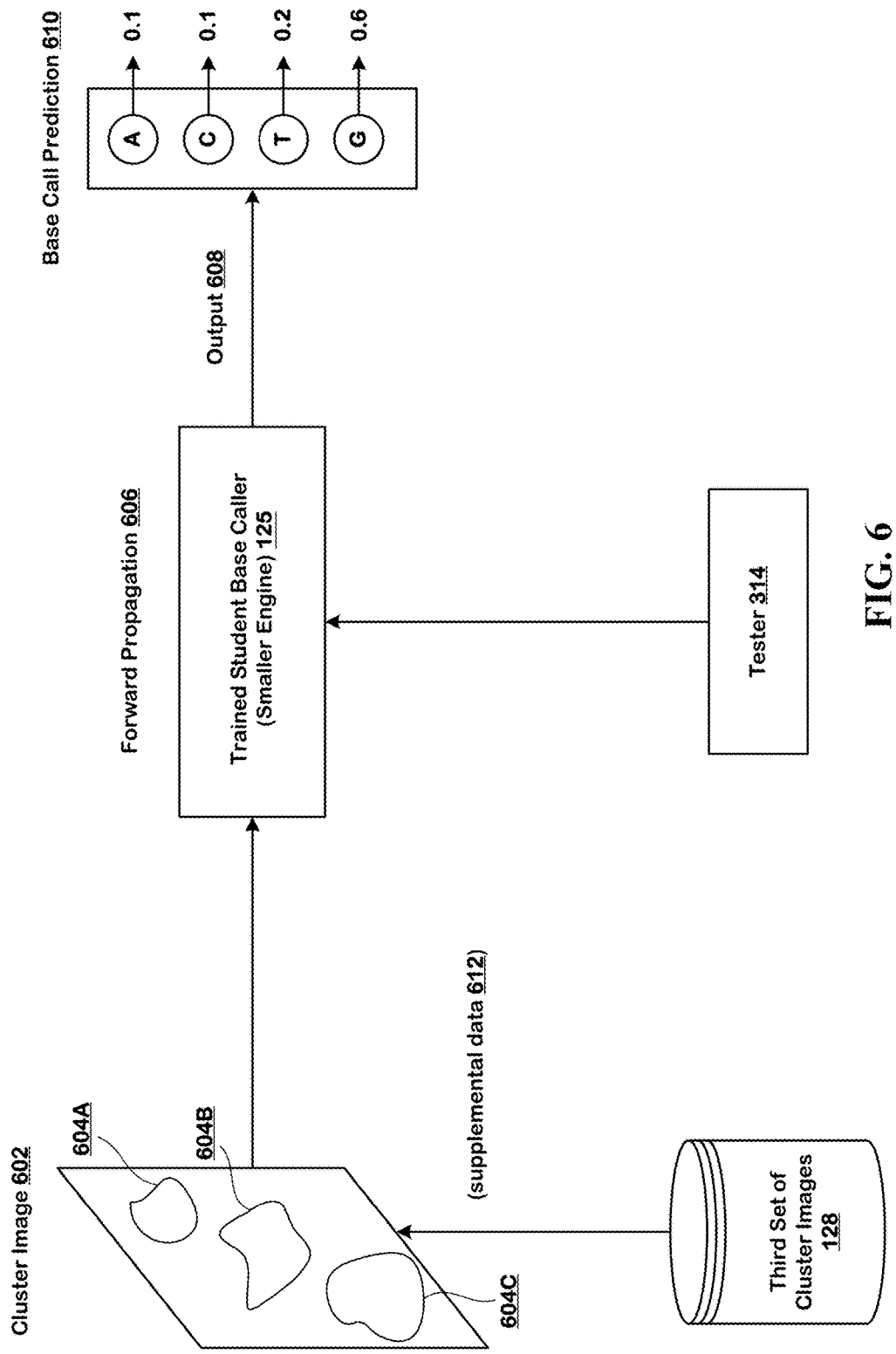
FIG. 6 shows one implementation of applying the trained student base caller on a third set of cluster images and generating base call predictions.

FIG. 6 shows one implementation of applying 600 the trained student base caller 125 on the third set of cluster images 128 and generating a base call prediction 610. During forward propagation 606, the input to the trained student base caller 125 is the cluster image 602 that depicts intensities of clusters 604A, 604B, and 604C and their surrounding background. In one implementation, the cluster image 602 is accompanied with supplemental data 612 such as the distance channel and the scaling channel.

In response to processing the cluster image 602, the trained student base caller 125 produces an output 608. Based on the output 608, the base call prediction 610 is generated that identifies confidence scores assigned by the trained student base caller 125 to each of the bases A (0.1), C (0.1), T (0.2), and G (0.6).

This process is iterated over numerous images in the third set of cluster images 128, such that the base call prediction is generated for each evaluated cluster image. The evaluation is operationalized (implemented) by the tester 314.

Technical Effect/Advantage

The teacher and student approach to transporting an intensely trained model from a resource-rich platform to a compact platform confers substantial technical benefits. The technology disclosed effectively shrinks the model and, with it, the execution time and resources required to analyze a particular input.

The extent of shrinkage is substantial, in most every proportion. FIGS. 16-17 show a reduction in filter depth from 64 filters to 14 filters. The shrunken model (the smaller, student base caller) has 21.9 percent as many filters as the large model (the larger, teacher base caller) for the resource-rich platform. The reduction in parameters is more dramatic, approximately quadratic with the reduction in filter depth. FIGS. 16-17 show a reduction in trainable parameter count form 250,060 to just 12,710. The shrunken model has 5.1 percent as many trainable parameters as the large model. For execution resources, the core calculations can be performed at the same time with compute resources reduced by 20-fold: computations scale about linearly with parameter count, so 5.1 percent as many parameters translates into 5.1 percent as many calculations required to process the same inputs. Memory usage also is reduced.

Reducing resource requirements is enabling for application of at least some commercially available computation accelerators, such as Xilinx FPGAs. In general, FPGAs have limited on-board memory and programmable footprint. The model in FIG. 16 will not run on a commercial FPGA offering such as Xilinx Alveo U200, Xilinx Alveo U250, Xilinx Alveo U280, Intel/Altera Stratix GX2800, Intel/Altera Stratix GX2800, and Intel Stratix GX10M, but the model in FIG. 17 will.

Figure 18:
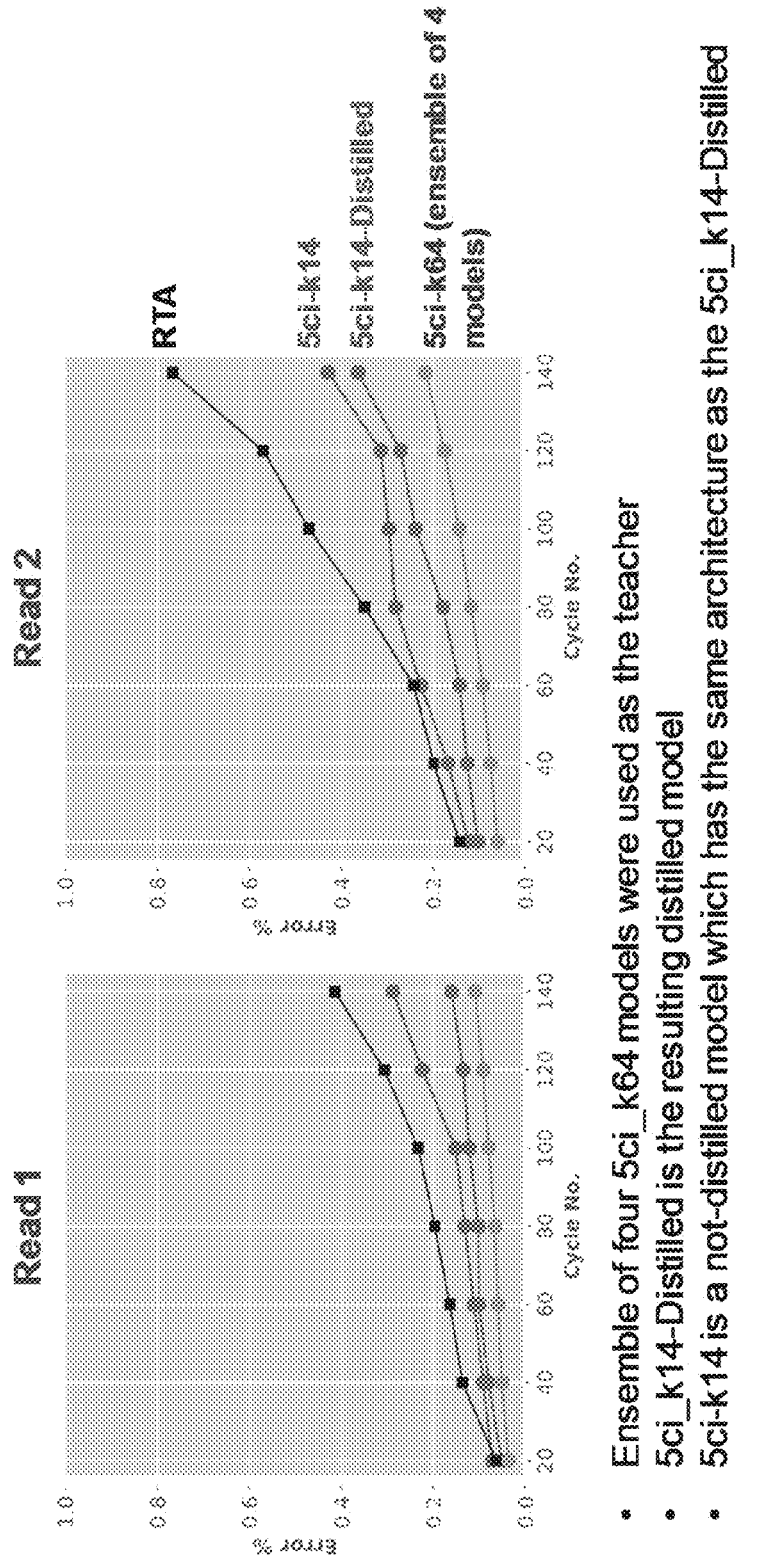
FIG. 18 shows the base calling performance of a smaller, student base caller against the base calling performance of a larger, teacher base caller.

Reduced resource requirements and elapsed run time are accomplished without compromising accuracy of results. FIG. 18 graphs results accomplished running the shrunken model against the large model. For all models, the error rate increases measurably as errors accumulate over multiple cycles. At 120 cycles, the error rate for the large model has crept up to 0.2 percent (0.002 error rate).

A new class of compact machine results, at a lower cost than one that with resources sufficient to run the large model. Results become available in real time, instead of being delayed by server-based computations. The technical improvements are manifest.

FIG. 16 shows one implementation of a larger, teacher base caller with 251,220 total parameters. The larger, teacher base caller has convolution layers that contain 64 filters per convolution layer.

FIG. 17 shows one implementation of a smaller, student base caller with 12,970 total parameters that is distilled from the larger, teacher base caller of FIG. 16 using the technology disclosed. The smaller, student base caller has convolution layers that contain 14 filters per convolution layer.

As shown in FIG. 17, the smaller, student base caller has about 5.1% of the total parameters as the larger, teacher base caller. In other implementations when the larger, teacher base caller comprises an ensemble of larger, teacher base callers, the smaller, student base caller has about 1% to 3% of the total parameters as the ensemble of larger, teacher base callers in the larger, teacher base caller. This significant reduction in the total number of model parameters makes the smaller, student base caller much more suitable for execution on on-chip processors like FPGAs, GPUs, ASICs, CGRAS.

FIG. 18 shows the base calling performance of a smaller, student base caller against the base calling performance of a larger, teacher base caller. The y-axis represents the base calling error rate (Error %) and the x-axis represents the sequencing cycles of a sequencing run. The purple line represents the larger, teacher base caller comprising an ensemble of four larger, teacher base callers that have 64 convolution filters per convolution layer. The cyan line represents the smaller, student base caller comprising that has 14 convolution filters per convolution layer. The smaller, student base caller (cyan line) is distilled from the larger, teacher base caller (purple line) using the technology disclosed.

As shown, the smaller, student base caller (cyan line) has a base calling error rate that is close to the base calling error rate (purple line) of the larger, teacher base caller comprising the ensemble of four larger, teacher base callers. Therefore, the technical advantage and technical effect of the technology disclosed is that the smaller, student base caller has much smaller compute footprint than the larger, teacher base caller, but similar/comparable base calling accuracy. This enables efficient execution of the smaller, student base caller during inference on on-chip processors like FPGAs, GPUs, ASICs, and CGRAs. This also improves the speed of base calling and reduces latency. This also leads to conservation of compute resources.

More importantly, the student model, as a distilled version of the teacher model, outperforms another model with the same architecture whose coefficients are independently learned and not derived from a teacher model.

Sequencing System

Figure 8A:
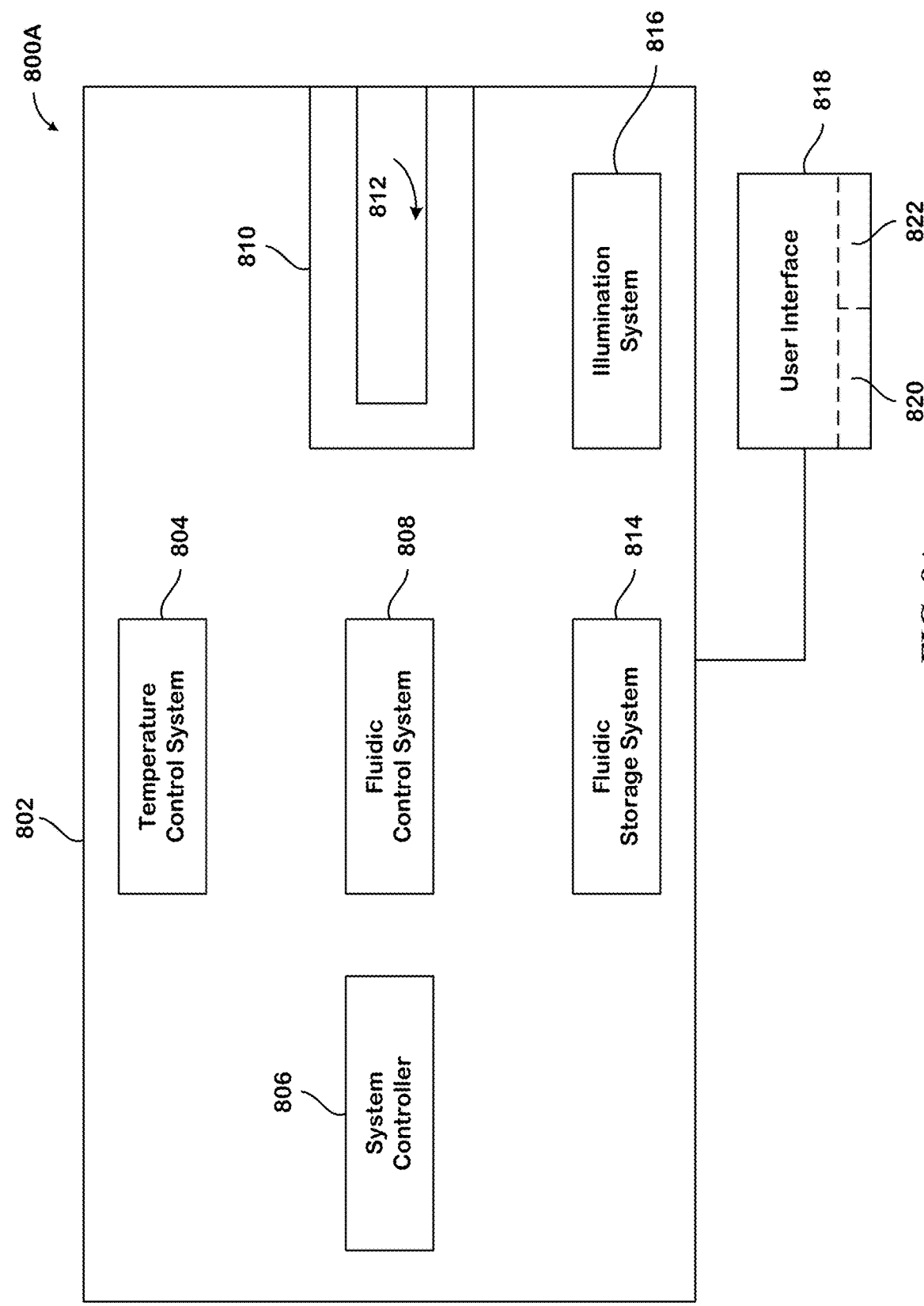
FIGS. 8A and 8B depict one implementation of a sequencer that uses the student base caller for base calling.
Figure 8B:
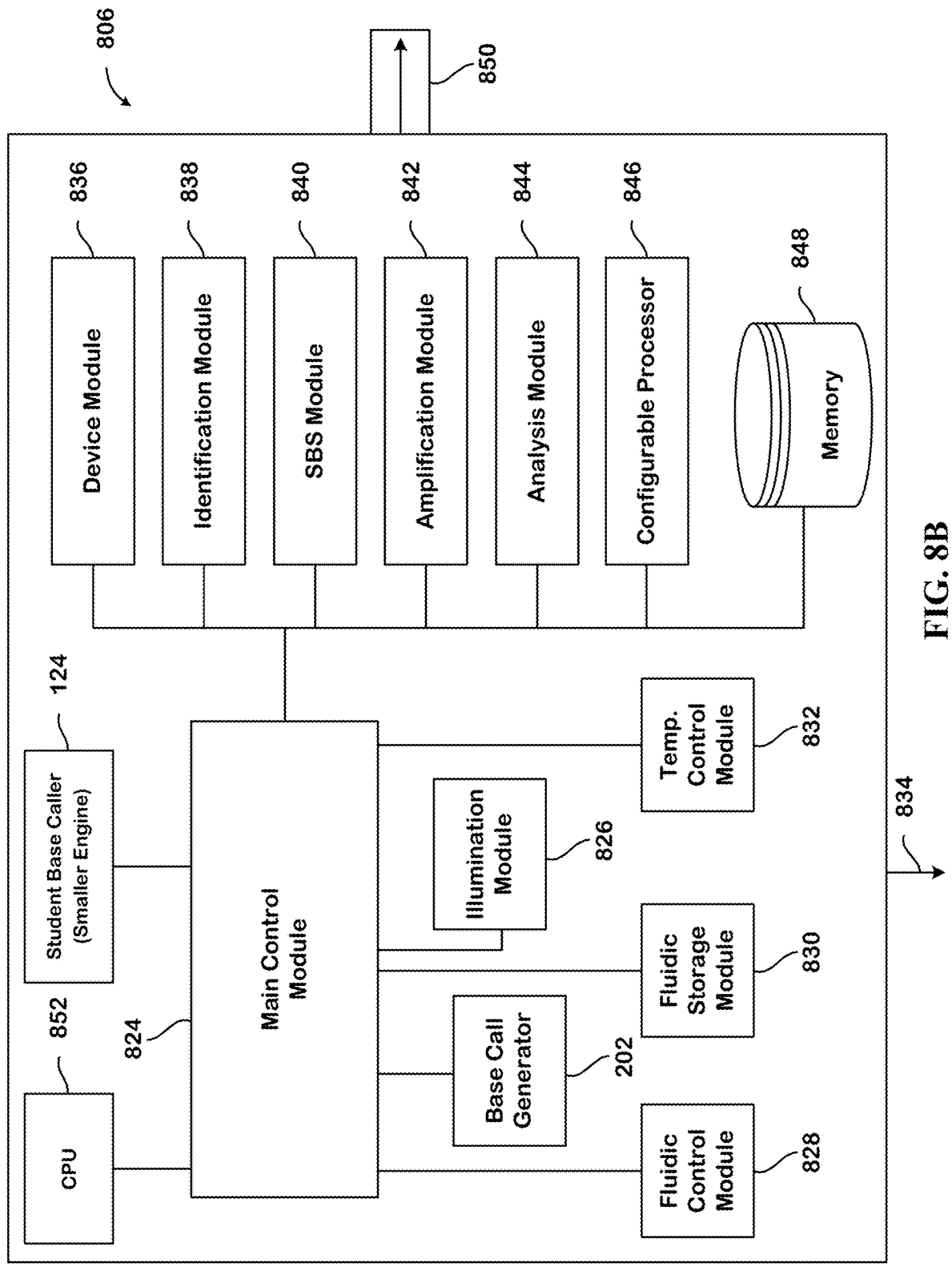

FIGS. 8A and 8B depict one implementation of a sequencing system 800A. The sequencing system 800A comprises a configurable processor 846. The configurable processor 846 implements the base calling techniques disclosed herein. The sequencing system is also referred to as a "sequencer."

The sequencing system 800A can operate to obtain any information or data that relates to at least one of a biological or chemical substance. In some implementations, the sequencing system 800A is a workstation that may be similar to a bench-top device or desktop computer. For example, a majority (or all) of the systems and components for conducting the desired reactions can be within a common housing 802.

In particular implementations, the sequencing system 800A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 800A may also be configured to generate reaction sites in a biosensor. For example, the sequencing system 800A may be configured to receive a sample and generate surface attached clusters of clonally amplified nucleic acids derived from the sample. Each cluster may constitute or be part of a reaction site in the biosensor.

The exemplary sequencing system 800A may include a system receptacle or interface 810 that is configured to interact with a biosensor 812 to perform desired reactions within the biosensor 812. In the following description with respect to FIG. 8A, the biosensor 812 is loaded into the system receptacle 810. However, it is understood that a cartridge that includes the biosensor 812 may be inserted into the system receptacle 810 and in some states the cartridge can be removed temporarily or permanently. As described above, the cartridge may include, among other things, fluidic control and fluidic storage components.

In particular implementations, the sequencing system 800A is configured to perform a large number of parallel reactions within the biosensor 812. The biosensor 812 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 812 may include a solid-state imaging device (e.g., CCD or CMOS imager) and a flow cell mounted thereto. The flow cell may include one or more flow channels that receive a solution from the sequencing system 800A and direct the solution toward the reaction sites. Optionally, the biosensor 812 can be configured to engage a thermal element for transferring thermal energy into or out of the flow channel.

The sequencing system 800A may include various components, assemblies, and systems (or sub-systems) that interact with each other to perform a predetermined method or assay protocol for biological or chemical analysis. For example, the sequencing system 800A includes a system controller 806 that may communicate with the various components, assemblies, and sub-systems of the sequencing system 800A and also the biosensor 812. For example, in addition to the system receptacle 810, the sequencing system 800A may also include a fluidic control system 808 to control the flow of fluid throughout a fluid network of the sequencing system 800A and the biosensor 812; a fluid storage system 814 that is configured to hold all fluids (e.g., gas or liquids) that may be used by the bioassay system; a temperature control system 804 that may regulate the temperature of the fluid in the fluid network, the fluid storage system 814, and/or the biosensor 812; and an illumination system 816 that is configured to illuminate the biosensor 812. As described above, if a cartridge having the biosensor 812 is loaded into the system receptacle 810, the cartridge may also include fluidic control and fluidic storage components.

Also shown, the sequencing system 800A may include a user interface 818 that interacts with the user. For example, the user interface 818 may include a display 820 to display or request information from a user and a user input device 822 to receive user inputs. In some implementations, the display 820 and the user input device 822 are the same device. For example, the user interface 818 may include a touch-sensitive display configured to detect the presence of an individual's touch and also identify a location of the touch on the display. However, other user input devices 822 may be used, such as a mouse, touchpad, keyboard, keypad, handheld scanner, voice-recognition system, motion-recognition system, and the like. As will be discussed in greater detail below, the sequencing system 800A may communicate with various components, including the biosensor 812 (e.g., in the form of a cartridge), to perform the desired reactions. The sequencing system 800A may also be configured to analyze data obtained from the biosensor to provide a user with desired information.

The system controller 806 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only and are thus not intended to limit in any way the definition and/or meaning of the term system controller. In the exemplary implementation, the system controller 806 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 800A.

The set of instructions may include various commands that instruct the sequencing system 800A or biosensor 812 to perform specific operations such as the methods and processes of the various implementations described herein. The set of instructions may be in the form of a software program, which may form part of a tangible, non-transitory computer readable medium or media. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 800A, processed in response to user inputs, or processed in response to a request made by another processing machine (e.g., a remote request through a communication link). In the illustrated implementation, the system controller 806 includes an analysis module 844. In other implementations, system controller 806 does not include the analysis module 844 and instead has access to the analysis module 844 (e.g., the analysis module 844 may be separately hosted on cloud).

The system controller 806 may be connected to the biosensor 812 and the other components of the sequencing system 800A via communication links. The system controller 806 may also be communicatively connected to off-site systems or servers. The communication links may be hard-wired, corded, or wireless. The system controller 806 may receive user inputs or commands, from the user interface 818 and the user input device 822.

The fluidic control system 808 includes a fluid network and is configured to direct and regulate the flow of one or more fluids through the fluid network. The fluid network may be in fluid communication with the biosensor 812 and the fluid storage system 814. For example, select fluids may be drawn from the fluid storage system 814 and directed to the biosensor 812 in a controlled manner, or the fluids may be drawn from the biosensor 812 and directed toward, for example, a waste reservoir in the fluid storage system 814. Although not shown, the fluidic control system 808 may include flow sensors that detect a flow rate or pressure of the fluids within the fluid network. The sensors may communicate with the system controller 806.

The temperature control system 804 is configured to regulate the temperature of fluids at different regions of the fluid network, the fluid storage system 814, and/or the biosensor 812. For example, the temperature control system 804 may include a thermocycler that interfaces with the biosensor 812 and controls the temperature of the fluid that flows along the reaction sites in the biosensor 812. The temperature control system 804 may also regulate the temperature of solid elements or components of the sequencing system 800A or the biosensor 812. Although not shown, the temperature control system 804 may include sensors to detect the temperature of the fluid or other components. The sensors may communicate with the system controller 806.

The fluid storage system 814 is in fluid communication with the biosensor 812 and may store various reaction components or reactants that are used to conduct the desired reactions therein. The fluid storage system 814 may also store fluids for washing or cleaning the fluid network and biosensor 812 and for diluting the reactants. For example, the fluid storage system 814 may include various reservoirs to store samples, reagents, enzymes, other biomolecules, buffer solutions, aqueous, and non-polar solutions, and the like. Furthermore, the fluid storage system 814 may also include waste reservoirs for receiving waste products from the biosensor 812. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 816 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 816 may be configured to direct an excitation light to reaction sites. As one example, fluorophores may be excited by green wavelengths of light, as such the wavelength of the excitation light may be approximately 532 nm. In one implementation, the illumination system 816 is configured to produce illumination that is parallel to a surface normal of a surface of the biosensor 812. In another implementation, the illumination system 816 is configured to produce illumination that is off-angle relative to the surface normal of the surface of the biosensor 812. In yet another implementation, the illumination system 816 is configured to produce illumination that has plural angles, including some parallel illumination and some off-angle illumination.

The system receptacle or interface 810 is configured to engage the biosensor 812 in at least one of a mechanical, electrical, and fluidic manner. The system receptacle 810 may hold the biosensor 812 in a desired orientation to facilitate the flow of fluid through the biosensor 812. The system receptacle 810 may also include electrical contacts that are configured to engage the biosensor 812 so that the sequencing system 800A may communicate with the biosensor 812 and/or provide power to the biosensor 812. Furthermore, the system receptacle 810 may include fluidic ports (e.g., nozzles) that are configured to engage the biosensor 812. In some implementations, the biosensor 812 is removably coupled to the system receptacle 810 in a mechanical manner, in an electrical manner, and also in a fluidic manner.

In addition, the sequencing system 800A may communicate remotely with other systems or networks or with other bioassay systems 800A. Detection data obtained by the bioassay system(s) 800A may be stored in a remote database.

FIG. 8B is a block diagram of a system controller 806 that can be used in the system of FIG. 8A. In one implementation, the system controller 806 includes one or more processors or modules that can communicate with one another. Each of the processors or modules may include an algorithm (e.g., instructions stored on a tangible and/or non-transitory computer readable storage medium) or sub-algorithms to perform particular processes. The system controller 806 is illustrated conceptually as a collection of modules, but may be implemented utilizing any combination of dedicated hardware boards, DSPs, processors, etc. Alternatively, the system controller 806 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 850 may transmit information (e.g., commands) to or receive information (e.g., data) from the biosensor 812 (FIG. 8A) and/or the sub-systems 808, 814, 804 (FIG. 8A). In implementations, the communication port 850 may output a plurality of sequences of pixel signals. A communication link 834 may receive user input from the user interface 818 (FIG. 8A) and transmit data or information to the user interface 818. Data from the biosensor 812 or sub-systems 808, 814, 804 may be processed by the system controller 806 in real-time during a bioassay session. Additionally or alternatively, data may be stored temporarily in a system memory during a bioassay session and processed in slower than real-time or off-line operation.

As shown in FIG. 8B, the system controller 806 may include a plurality of modules 828-844 that communicate with a main control module 824, along with a central processing unit (CPU) 852. The main control module 824 may communicate with the user interface 818 (FIG. 8A). Although the modules 828-844 are shown as communicating directly with the main control module 824, the modules 828-844 may also communicate directly with each other, the user interface 818, and the biosensor 812. Also, the modules 828-844 may communicate with the main control module 824 through the other modules.

The plurality of modules 828-844 include system modules 828-832, 826 that communicate with the sub-systems 808, 814, 804, and 816, respectively. The fluidic control module 828 may communicate with the fluidic control system 808 to control the valves and flow sensors of the fluid network for controlling the flow of one or more fluids through the fluid network. The fluid storage module 830 may notify the user when fluids are low or when the waste reservoir is at or near capacity. The fluid storage module 830 may also communicate with the temperature control module 832 so that the fluids may be stored at a desired temperature.

The illumination module 826 may communicate with the illumination system 816 to illuminate the reaction sites at designated times during a protocol, such as after the desired reactions (e.g., binding events) have occurred. In some implementations, the illumination module 826 may communicate with the illumination system 816 to illuminate the reaction sites at designated angles.

The plurality of modules 828-844 may also include a device module 836 that communicates with the biosensor 812 and an identification module 838 that determines identification information relating to the biosensor 812. The device module 836 may, for example, communicate with the system receptacle 810 to confirm that the biosensor has established an electrical and fluidic connection with the sequencing system 800A. The identification module 838 may receive signals that identify the biosensor 812. The identification module 838 may use the identity of the biosensor 812 to provide other information to the user. For example, the identification module 838 may determine and then display a lot number, a date of manufacture, or a protocol that is recommended to be run with the biosensor 812.

The plurality of modules 828-844 also includes an analysis module 844 (also called signal processing module or signal processor) that receives and analyzes the signal data (e.g., image data) from the biosensor 812. Analysis module 844 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 818 to display desired information to the user. In some implementations, the signal data may be processed by the solid-state imager (e.g., CMOS image sensor) before the analysis module 844 receives the signal data.

The analysis module 844 is configured to obtain image data from the light detectors at each of a plurality of sequencing cycles. The image data is derived from the emission signals detected by the light detectors and process the image data for each of the plurality of sequencing cycles through the student base caller 124 and produce a base call for at least some of the analytes at each of the plurality of sequencing cycle. The light detectors can be part of one or more over-head cameras (e.g., Illumina's GAIIx's CCD camera taking images of the clusters on the biosensor 812 from the top), or can be part of the biosensor 812 itself (e.g., Illumina's iSeq's CMOS image sensors underlying the clusters on the biosensor 812 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 848.

Protocol modules 840 and 842 communicate with the main control module 824 to control the operation of the sub-systems 808, 814, and 804 when conducting predetermined assay protocols. The protocol modules 840 and 842 may include sets of instructions for instructing the sequencing system 800A to perform specific operations pursuant to predetermined protocols. As shown, the protocol module may be a sequencing-by-synthesis (SBS) module 840 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 816 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; 7,405,281, and US 2008/014708082, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 842 that is configured to issue commands to the fluidic control system 808 and the temperature control system 804 for amplifying a product within the biosensor 812. For example, the biosensor 812 may be engaged to the sequencing system 800A. The amplification module 842 may issue instructions to the fluidic control system 808 to deliver necessary amplification components to reaction chambers within the biosensor 812. In other implementations, the reaction sites may already contain some components for amplification, such as the template DNA and/or primers. After delivering the amplification components to the reaction chambers, the amplification module 842 may instruct the temperature control system 804 to cycle through different temperature stages according to known amplification protocols. In some implementations, the amplification and/or nucleotide incorporation is performed isothermally.

The SBS module 840 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 840 may instruct the fluidic control system 808 to direct a flow of reagent and enzyme solutions through the biosensor 812. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/02814714709 A1, PCT Publication No. WO 05/065814, US Patent Application Publication No. 2005/014700900 A1, PCT Publication No. WO 06/08B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592,435 and WO 07/14835368, each of which is incorporated herein by reference in its entirety.

In some implementations, the amplification and SBS modules may operate in a single assay protocol where, for example, template nucleic acid is amplified and subsequently sequenced within the same cartridge.

The sequencing system 800A may also allow the user to reconfigure an assay protocol. For example, the sequencing system 800A may offer options to the user through the user interface 818 for modifying the determined protocol. For example, if it is determined that the biosensor 812 is to be used for amplification, the sequencing system 800A may request a temperature for the annealing cycle. Furthermore, the sequencing system 800A may issue warnings to a user if a user has provided user inputs that are generally not acceptable for the selected assay protocol.

In implementations, the biosensor 812 includes millions of sensors (or pixels), each of which generates a plurality of sequences of pixel signals over successive base calling cycles. The analysis module 844 detects the plurality of sequences of pixel signals and attributes them to corresponding sensors (or pixels) in accordance to the row-wise and/or column-wise location of the sensors on an array of sensors.

Figure 8C:
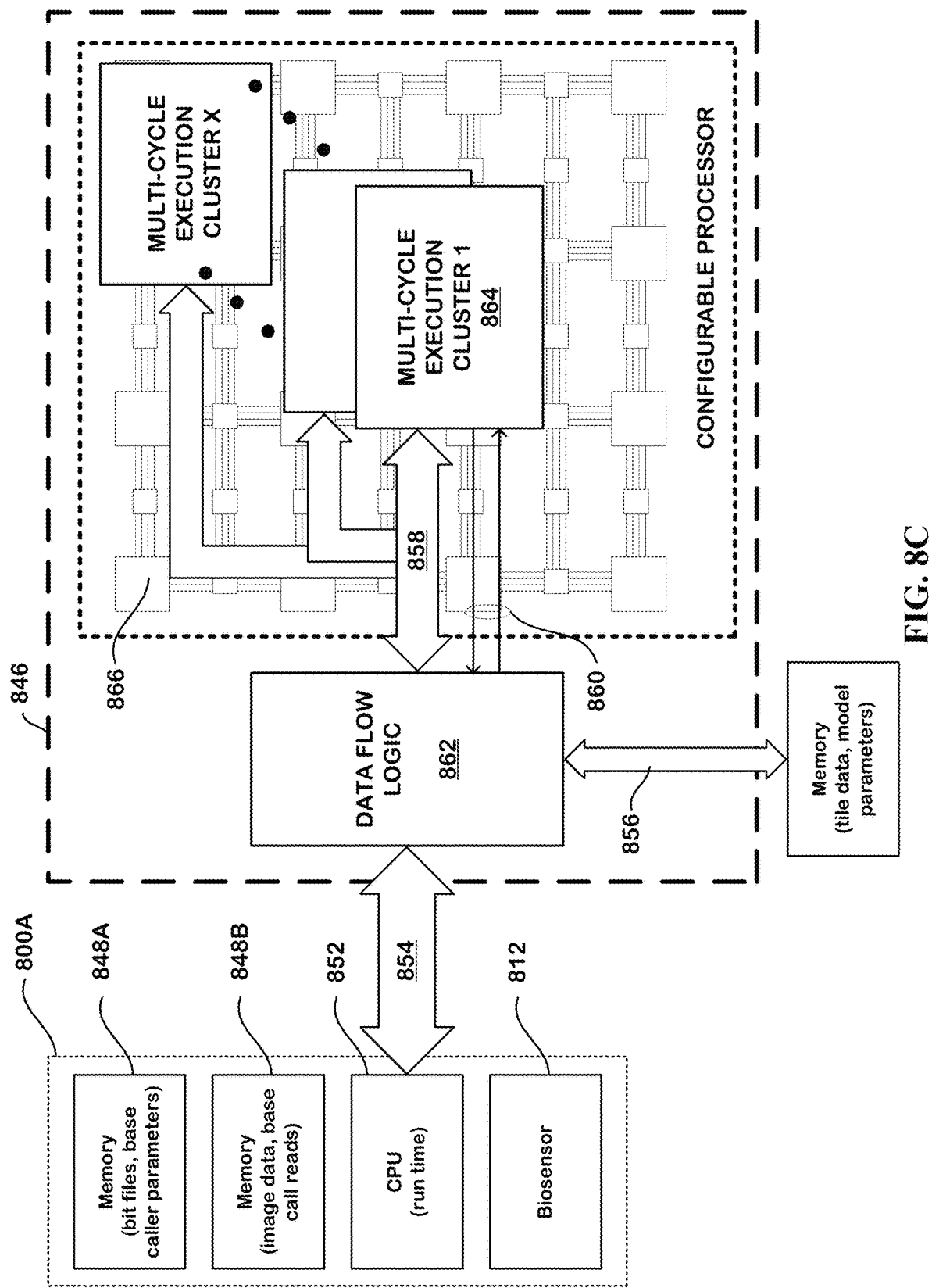
FIG. 8C is a simplified block diagram of a system for analysis of sensor data from the sequencing system, such as base call sensor outputs.

FIG. 8C is a simplified block diagram of a system for analysis of sensor data from the sequencing system 800A, such as base call sensor outputs. In the example of FIG. 8C, the system includes the configurable processor 846. The configurable processor 846 can execute a base caller (e.g., the student base caller 124) in coordination with a runtime program executed by the central processing unit (CPU) 852 (i.e., a host processor). The sequencing system 800A comprises the biosensor 812 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 852, which executes a runtime program to coordinate the base call operations, memory 848B to store sequences of arrays of tile data, base call reads produced by the base calling operation, and other information used in the base call operations. Also, in this illustration the system includes memory 848A to store a configuration file (or files), such as FPGA bit files, and model parameters for the neural networks used to configure and reconfigure the configurable processor 846, and execute the neural networks. The sequencing system 800A can include a program for configuring a configurable processor and in some embodiments a reconfigurable processor to execute the neural networks.

The sequencing system 800A is coupled by a bus 854 to the configurable processor 846. The bus 854 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 848A is coupled to the configurable processor 846 by bus 854. The memory 848A can be on-board memory, disposed on a circuit board with the configurable processor 846. The memory 848A is used for high speed access by the configurable processor 846 of working data used in the base call operation. The bus 856 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the student base caller 124 using the configurable processor 846. The configuration file for the configurable processor 846 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 846, in all embodiments described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 846 is configured in this example by a configuration file loaded using a program executed by the CPU 852, or by other sources, which configures the array of configurable elements 866 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 862 which is coupled to the buses 854 and 856 and executes functions for distributing data and control parameters among the elements used in the base call operation.

Also, the configurable processor 846 is configured with base call execution logic 862 to execute the student base caller 124. The logic 862 comprises multi-cycle execution clusters (e.g., 864) which, in this example, includes execution cluster 1 through execution cluster X. The number of multi-cycle execution clusters can be selected according to a trade-off involving the desired throughput of the operation, and the available resources on the configurable processor 846.

The multi-cycle execution clusters are coupled to the data flow logic 862 by data flow paths 858 implemented using configurable interconnect and memory resources on the configurable processor 846. Also, the multi-cycle execution clusters are coupled to the data flow logic 862 by control paths 860 implemented using configurable interconnect and memory resources for example on the configurable processor 846, which provide control signals indicating available execution clusters, readiness to provide input units for execution of a run of the student base caller 124 to the available execution clusters, readiness to provide trained parameters for the student base caller 124, readiness to provide output patches of base call classification data, and other control data used for execution of the student base caller 124.

The configurable processor 846 is configured to execute runs of the student base caller 124 using trained parameters to produce classification data for the sensing cycles of the base calling operation. A run of the student base caller 124 is executed to produce classification data for a subject sensing cycle of the base calling operation. A run of the student base caller 124 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 862 is configured to move tile data and at least some trained parameters of the model parameters from the memory 848A to the configurable processor 846 for runs of the student base caller 124, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the student base caller 124 as described below, tile data can also include data produced during execution of the student base caller 124, referred to as intermediate data, which can be reused rather than recomputed during a run of the student base caller 124. For example, during execution of the student base caller 124, the data flow logic 862 can write intermediate data to the memory 848A in place of the sensor data for a given patch of an array of tile data. Embodiments like this are described in more detail below.

As illustrated, a system is described for analysis of base call sensor output, comprising memory (e.g., 848A) accessible by the runtime program storing tile data including sensor data for a tile from sensing cycles of a base calling operation. Also, the system includes a neural network processor, such as configurable processor 846 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 862 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 862 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 8D:
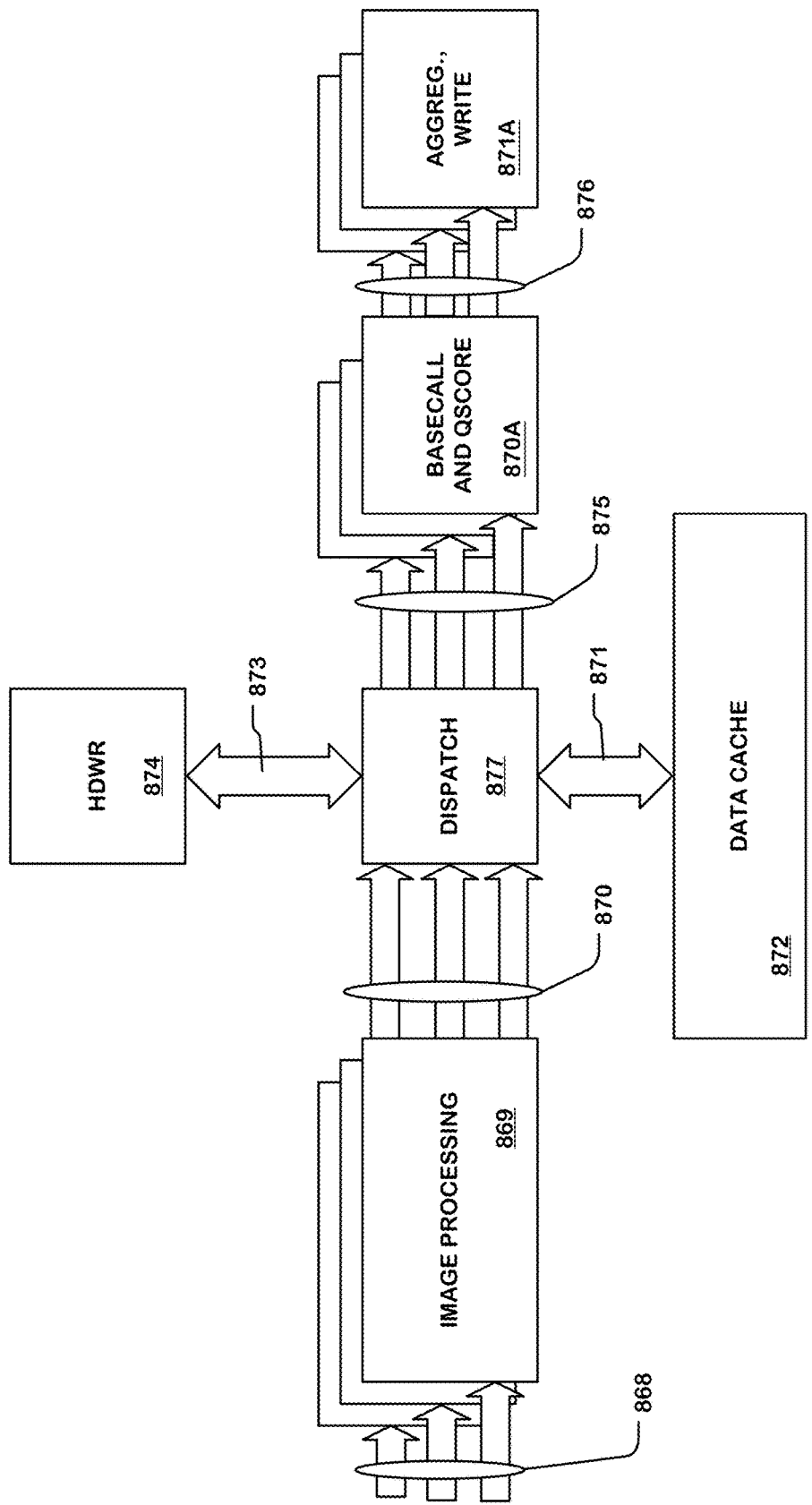
FIG. 8D is a simplified diagram showing aspects of the base calling operation, including functions of a runtime program executed by a host processor.

FIG. 8D is a simplified diagram showing aspects of the base calling operation, including functions of a runtime program executed by a host processor. In this diagram, the output of image sensors from a flow cell are provided on lines 868 to image processing threads 869, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 869 are provided on lines 870 to a dispatch logic 877 in the CPU which routes the arrays of tile data to a data cache 872 (e.g., SSD storage) on a high-speed bus 871, or on high-speed bus 873 to the neural network processor hardware 874, such as the configurable processor 846 of FIG. 8C, according to the state of the base calling operation. The processed and transformed images can be stored on the data cache 872 for sensing cycles that were previously used. The hardware 874 returns classification data output by the neural network to the dispatch logic 877, which passes the information to the data cache 872, or on lines 875 to threads 870A that perform base call and quality score computations using the classification data, and can arrange the data in standard formats for base call reads. The outputs of the threads 870A that perform base calling and quality score computations are provided on lines 876 to threads 871A that aggregate the base call reads, perform other operations such as data compression, and write the resulting base call outputs to specified destinations for utilization by the customers.

In some embodiments, the host can include threads (not shown) that perform final processing of the output of the hardware 874 in support of the neural network. For example, the hardware 874 can provide outputs of classification data from a final layer of the multi-cluster neural network. The host processor can execute an output activation function, such as a softmax function, over the classification data to configure the data for use by the base call and quality score threads 870A. Also, the host processor can execute input operations (not shown), such as batch normalization of the tile data prior to input to the hardware 874.

In some embodiments, the host can include threads (not shown) that perform final processing of the output of the hardware 874 in support of the neural network. For example, the hardware 874 can provide outputs of classification data from a final layer of the multi-cluster neural network. The host processor can execute an output activation function, such as a softmax function, over the classification data to configure the data for use by the base call and quality score threads 870. Also, the host processor can execute input operations (not shown), such as batch normalization of the tile data prior to input to the hardware 874.

Figure 8E:
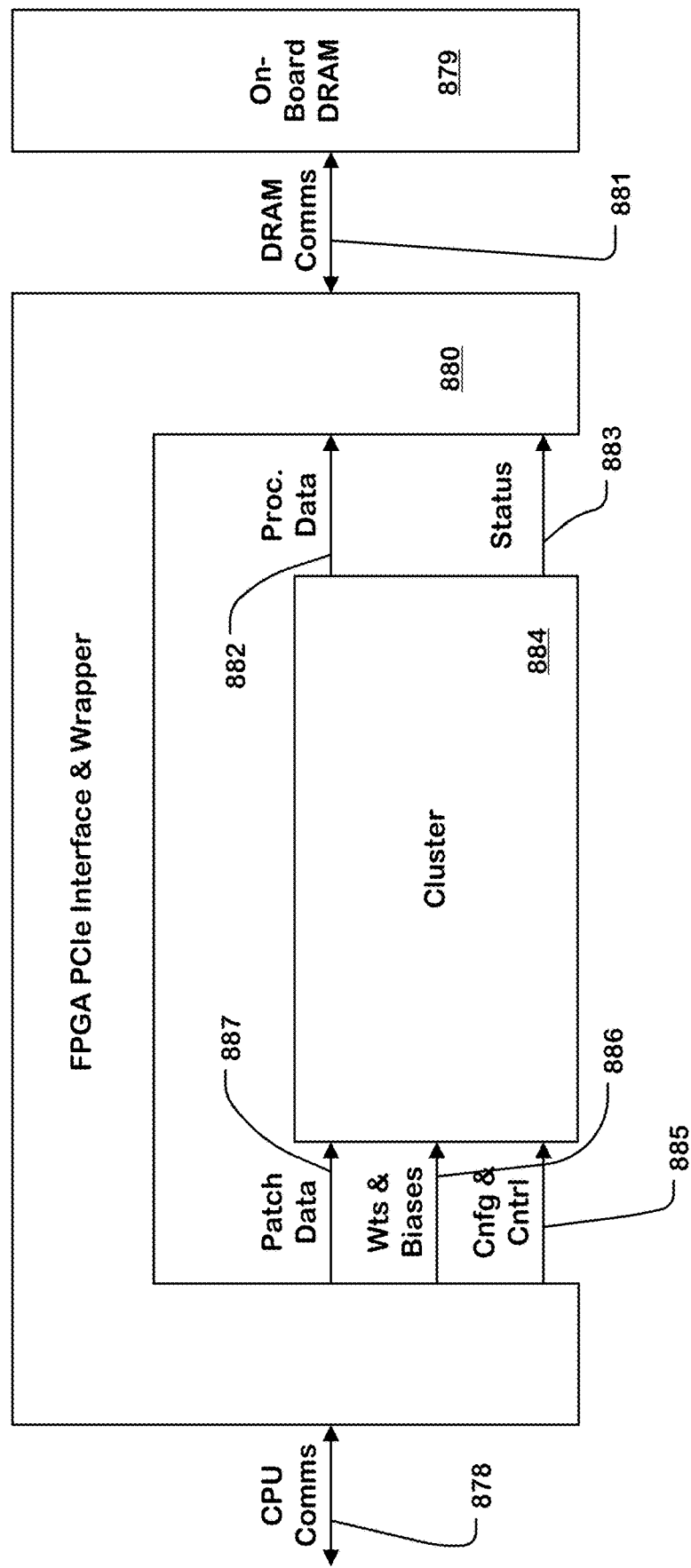
FIG. 8E is a simplified diagram of a configuration of a configurable processor 846 such as that of FIG. 8C.

FIG. 8E is a simplified diagram of a configuration of a configurable processor 846 such as that of FIG. 8C. In FIG. 8E, the configurable processor 846 comprises an FPGA with a plurality of high speed PCIe interfaces. The FPGA is configured with a wrapper 880 which comprises the data flow logic 862 described with reference to FIG. 8C. The wrapper 880 manages the interface and coordination with a runtime program in the CPU across the CPU communication link 878 and manages communication with the on-board DRAM 879 (e.g., memory 848A) via DRAM communication link 881. The data flow logic 862 in the wrapper 880 provides patch data retrieved by traversing the arrays of tile data on the on-board DRAM 879 for the number N cycles to a cluster 884, and retrieves process data 882 from the cluster 884 for delivery back to the on-board DRAM 879. The wrapper 880 also manages transfer of data between the on-board DRAM 879 and host memory, for both the input arrays of tile data, and for the output patches of classification data. The wrapper transfers patch data on line 887 to the allocated cluster 884. The wrapper provides trained parameters, such as weights and biases on line 886 to the cluster 884 retrieved from the on-board DRAM 302. The wrapper provides configuration and control data on line 885 to the cluster 884 provided from, or generated in response to, the runtime program on the host via the CPU communication link 878. The cluster can also provide status signals on line 883 to the wrapper 880, which are used in cooperation with control signals from the host to manage traversal of the arrays of tile data to provide spatially aligned patch data, and to execute the multi-cycle neural network over the patch data using the resources of the cluster 884.

As mentioned above, there can be multiple clusters on a single configurable processor managed by the wrapper 880 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 880. The wrapper 880 can optionally do some pre-processing and transformation of the sensing data and write the information to the on-board DRAM 879. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 879. When the processing of the entire tile has been completed, and the output patches of data transferred to the DRAM, the wrapper sends the processed output array for the tile back to the host/CPU in a specified format. In some embodiments, the on-board DRAM 879 is managed by memory management logic in the wrapper 880. The runtime program can control the sequencing operations to complete analysis of all the arrays of tile data for all the cycles in the run in a continuous flow to provide real time analysis.

"Logic" (e.g., data flow logic), as used herein, can be implemented in the form of a computer product including a non-transitory computer readable storage medium with computer usable program code for performing the method steps described herein. The "logic" can be implemented in the form of an apparatus including a memory and at least one processor that is coupled to the memory and operative to perform exemplary method steps. The "logic" can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media). In one implementation, the logic implements a data processing function. The logic can be a general purpose, single core or multicore, processor with a computer program specifying the function, a digital signal processor with a computer program, configurable logic such as an FPGA with a configuration file, a special purpose circuit such as a state machine, or any combination of these. Also, a computer program product can embody the computer program and configuration file portions of the logic.

Computer System

Figure 9:
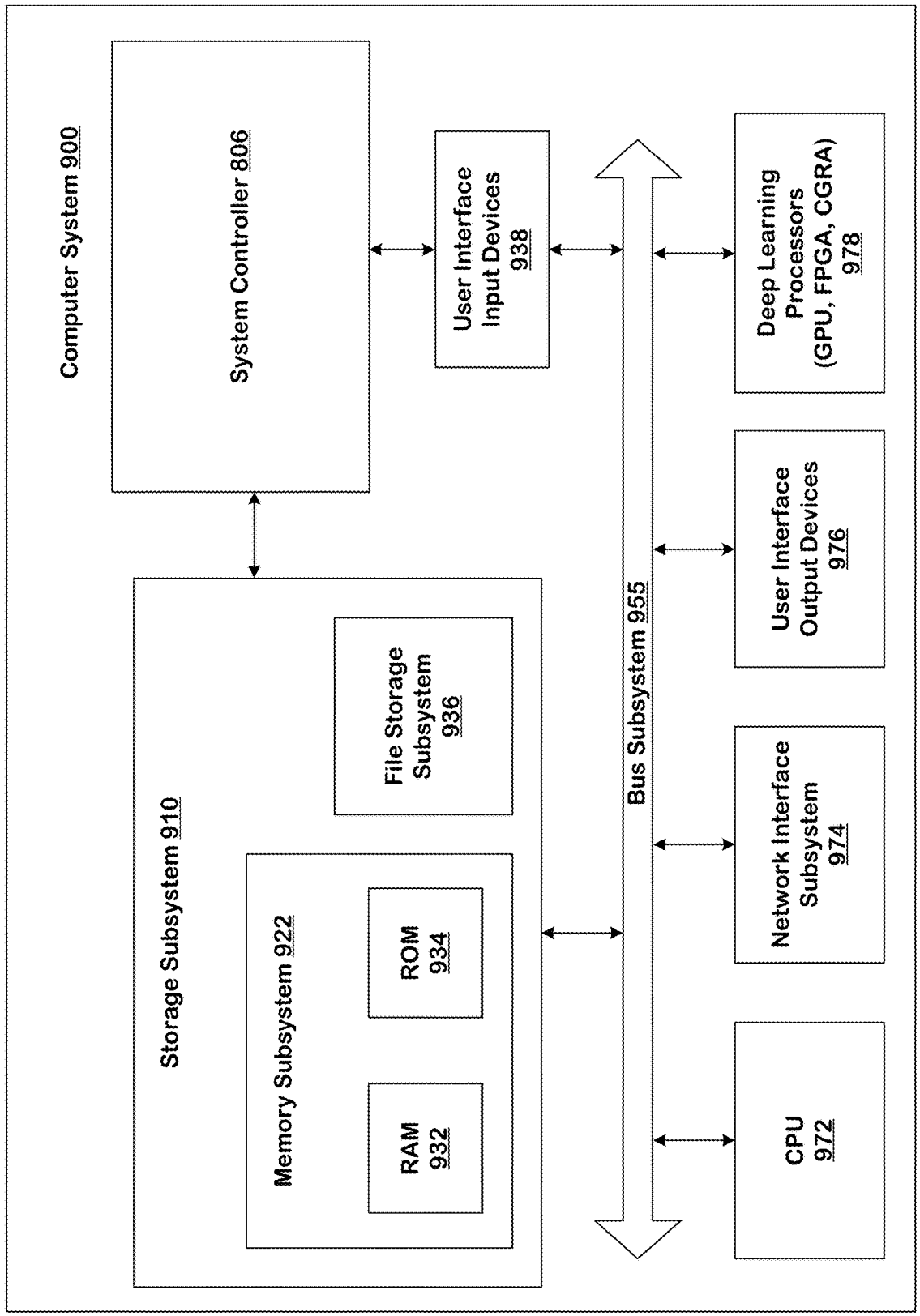
FIG. 9 is a simplified block diagram of a computer system that can be used to implement the technology disclosed.

FIG. 9 is a computer system 900 that can be used by the sequencing system 800A to implement the base calling techniques disclosed herein. Computer system 900 includes at least one central processing unit (CPU) 972 that communicates with a number of peripheral devices via bus subsystem 955. These peripheral devices can include a storage subsystem 910 including, for example, memory devices and a file storage subsystem 936, user interface input devices 938, user interface output devices 976, and a network interface subsystem 974. The input and output devices allow user interaction with computer system 900. Network interface subsystem 974 provides an interface to outside networks, including an interface to corresponding interface devices in other computer systems.

In one implementation, the system controller 806 is communicably linked to the storage subsystem 910 and the user interface input devices 938.

User interface input devices 938 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 900.

User interface output devices 976 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 900 to the user or to another machine or computer system.

Storage subsystem 125 stores programming and data constructs that provide the functionality of some or all of the modules and methods described herein. These software modules are generally executed by deep learning processors 978.

Deep learning processors 978 can be graphics processing units (GPUs), field-programmable gate arrays (FPGAs), application-specific integrated circuits (ASICs), and/or coarse-grained reconfigurable architectures (CGRAs). Deep learning processors 978 can be hosted by a deep learning cloud platform such as Google Cloud Platform™, Xilinx™, and Cirrascale™. Examples of deep learning processors 978 include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 922 used in the storage subsystem 125 can include a number of memories including a main random access memory (RAM) 932 for storage of instructions and data during program execution and a read only memory (ROM) 934 in which fixed instructions are stored. A file storage subsystem 936 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 936 in the storage subsystem 125, or in other machines accessible by the processor.

Bus subsystem 955 provides a mechanism for letting the various components and subsystems of computer system 900 communicate with each other as intended. Although bus subsystem 955 is shown schematically as a single bus, alternative implementations of the bus subsystem can use multiple busses.

Computer system 900 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 900 depicted in FIG. 9 is intended only as a specific example for purposes of illustrating the preferred implementations of the present invention. Many other configurations of computer system 900 are possible having more or less components than the computer system depicted in FIG. 9.

Pruning

We also disclose an artificial intelligence-based technology of performing computationally efficient base calling. FIG. 10A shows one implementation of training 1004 a first base caller 1006 over cluster intensity images 1002 and producing a first trained base caller 1006. FIG. 10B shows one implementation of the first trained base caller 1006 mapping the cluster intensity images 1002 (e.g., the cluster image 1008) to base call predictions 1010.

Figure 11A:
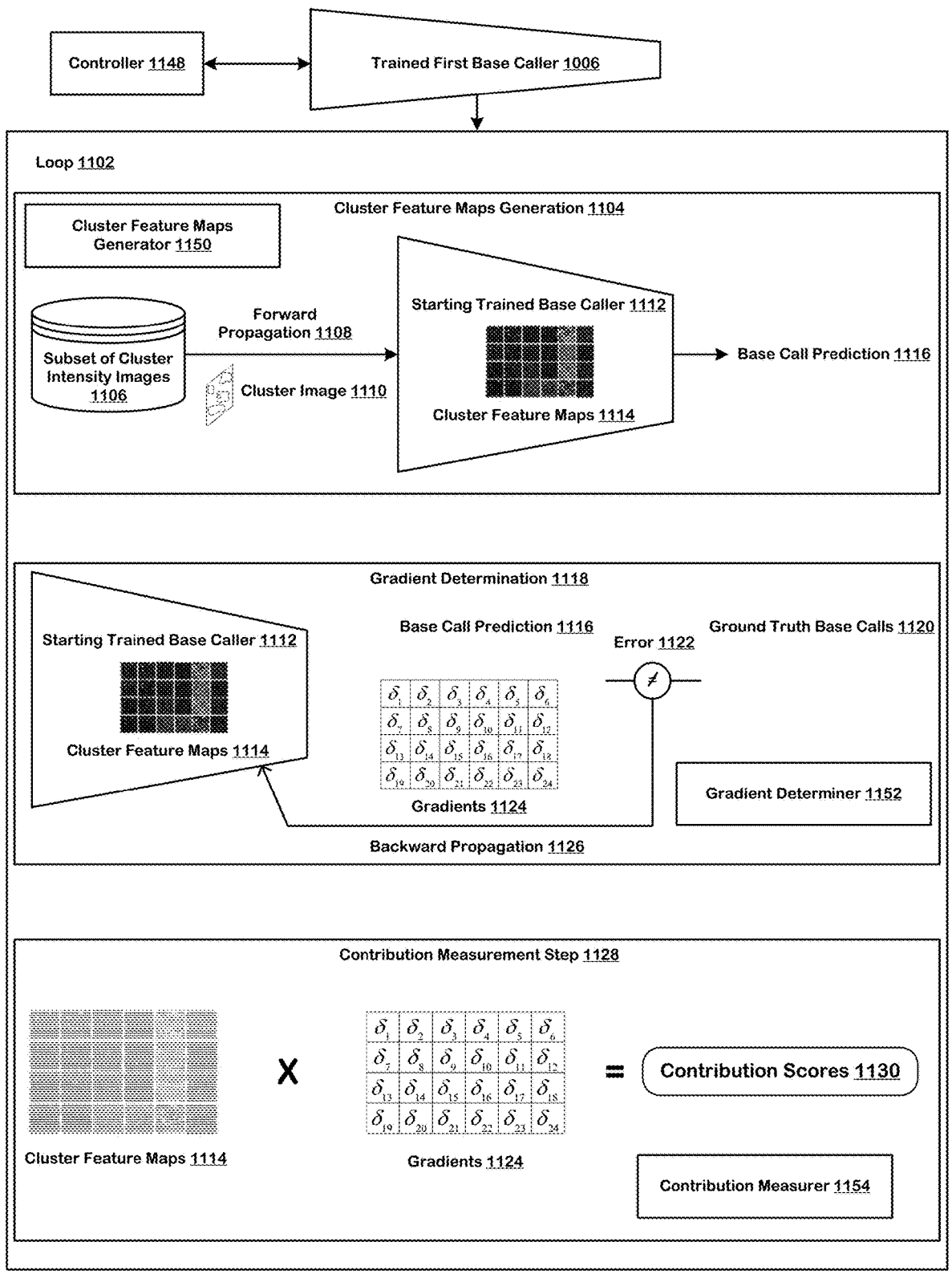
FIGS. 11A and 11B show various aspects of a loop implemented by the technology disclosed to perform computationally efficient base calling.
Figure 11B:
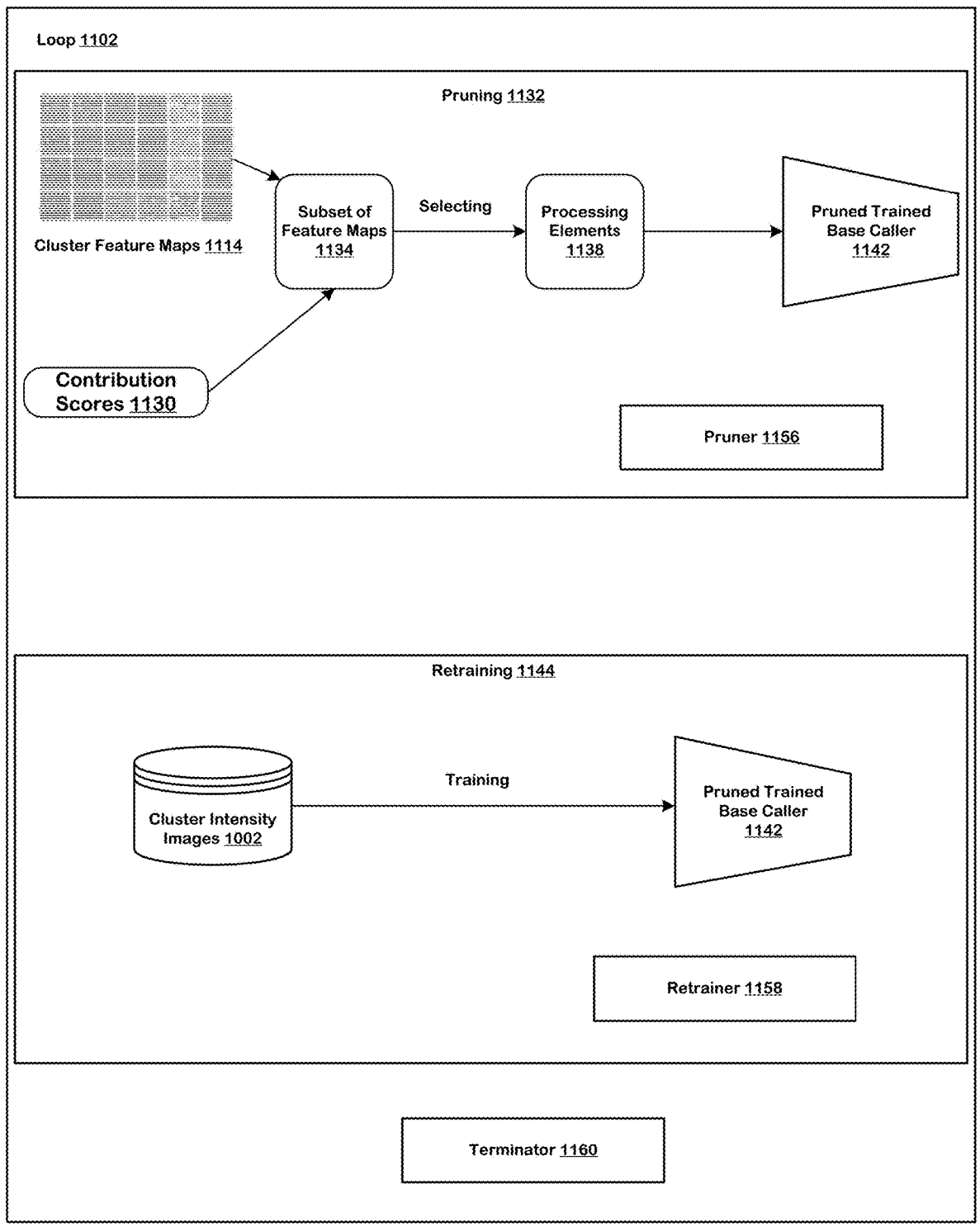

FIGS. 11A and 11B show various aspects of a loop implemented by the technology disclosed to perform computationally efficient base calling.

A controller 1148 begins with the first trained base caller 1006 and executes a loop 1102 in which each iteration uses a starting trained base caller 1112 as input and produces a pruned trained base caller 1142 as output. The pruned trained base caller 1142 has fewer processing elements than the starting trained base caller 1112. In one implementation, the first trained base caller 1006 is a neural network, and the processing elements are neurons of the neural network. In another implementation, the first trained base caller 1006 is a convolutional neural network, and the processing elements are convolutional filters of the convolutional neural network. In yet another implementation, the processing elements are convolutional kernels of the convolutional neural network. In yet further implementation, the processing elements are weights of the convolutional kernels of the convolutional neural network. In another implementation, the first trained base caller 1006 is a recurrent neural network, and the processing elements are weights of gates of the recurrent neural network.

In yet further implementation, the first trained base caller 1006 is a fully-connected neural network.

In yet further implementation, the processing elements are the cluster feature maps. The cluster feature maps can be convolved features or convolved representations when the first trained base caller 1006 is a convolutional neural network. The cluster feature maps can be hidden state features or hidden state representations when the first trained base caller 1006 is a recurrent neural network.

When a convolution filter convolves over a cluster image (or a cluster intensity image), the resulting output is called the cluster feature map. Similarly, when a convolution filter convolves over a cluster feature map produced in an another convolution layer (e.g., a preceding convolution layer), the resulting output is also called the cluster feature map. In one implementation, the cluster feature map is produced by element-wise multiplying the elements of the convolution filter (neurons) with corresponding elements (e.g., intensity values) of the cluster intensity image, or of a cluster feature map produced in an another convolution layer (e.g., a preceding convolution layer), and summing the results of the element-wise multiplication to produce the cluster feature map.

A cluster feature maps generator 1150, in each iteration, during forward propagation 1108, processes a subset 1106 of the clusters intensity images (e.g., cluster image 1110) through the processing elements of the starting trained base caller 1112, generates one or more cluster feature maps 1114 using each processing element, and produces the base call predictions 1116 based on the cluster feature maps 1114. This is considered the cluster feature maps generation step 1104.

A gradient determiner 1152, in each iteration, during backward propagation 1126, determines gradients 1124 for the cluster feature maps 1114 based on error 1122 between the base call predictions 1116 and ground truth base calls 1120. This is considered the gradient determination step 1118.

A contribution measurer 1154, in each iteration, applies the gradients 1124 to respective ones of the cluster feature maps 1114 and generates a contribution score 1130 for each of the cluster feature maps 1114 that identifies how much a cluster feature map contributed to the base call predictions 1116. This is considered the contribution measurement step 1128.

Figure 12:
FIG. 12 illustrates one implementation of generating contribution scores for the cluster feature maps.

FIG. 12 illustrates one implementation of generating contribution scores for the cluster feature maps. In one implementation, the contribution score 1214 for a cluster feature map 1202 is generated by multiplying each of the feature values 1204 in the cluster feature map 1202 with a respective one of the gradients 1206 and producing intermediate feature values 1208, applying an absolute function 1210 to the intermediate feature values 1208 and generating absolute intermediate feature values 1212, and summing the absolute intermediate feature values 1212 and producing the contribution score 1214 for the cluster feature map 1202.

In another implementation, the contribution score 1214 for the cluster feature map 1202 is generated without using the gradients 1206. This includes applying the absolute function 1210 to the feature values (weights) 1204 in the cluster feature map 1202 and generating absolute feature values, and summing the absolute feature values to produce the contribution score 1214 for the cluster feature map 1202.

A pruner 1156, in each iteration, selects a subset 1134 of the cluster feature maps based on their contribution scores 1130 and produces the pruned trained base caller 1142 by removing, from the starting trained base caller 1112, those processing elements 1138 that were used to generate the selected subset 1134 of the cluster feature maps during the forward propagation 1108. This is considered the pruning step 1132.

A retrainer 1158, in each iteration, further trains the pruned trained base caller 1142 over the cluster intensity images 1002 and makes the pruned trained base caller 1142 available for a successive iteration as the starting trained base caller 1112.

A terminator 1160 terminates the loop 1102 after n iterations and uses the pruned trained base caller 1142 produced by the nth iteration for further base calling.

In one implementation, each iteration, during the forward propagation, processes the subset of the clusters intensity images through the processing elements of the starting trained base caller in batches. In such an implementation, the gradients for the cluster feature map are determined on a batch-by-batch basis, the absolute intermediate feature values for the cluster feature map are generated on the batch-by-batch basis, and the contribution score for the cluster feature map is generated by summing the absolute intermediate feature values for each of the batches.

In one implementation, Lp normalization is used for the training of the first base caller 1106. The Lp normalization can be L-1 normalization, L-2 normalization, and L-infinity normalization. In one implementation, for a first iteration, the Lp normalization produces a subset of the cluster feature maps whose contribution score is zero. For the first iteration, the pruning step 1132 first removes, from the first trained base caller 1006, those processing elements that were used generate the cluster feature maps whose contribution score is zero due to the Lp normalization, and then removes, from the first trained base caller 1006, the processing elements that were used to generate the selected subset 1134 of the cluster feature maps during the forward propagation.

Other examples of normalization include L-0 normalization, absolute-value normalization, Euclidean normalization, Taxicab or Manhattan normalization, p-normalization, maximum normalization, infinity normalization, uniform normalization, supremum normalization, and zero normalization. Additional information about and examples of normalization techniques can be found at "Mathematics." Wikipedia, The Free Encyclopedia, Wikimedia Foundation, 3 Feb. 2024, (https://en.wikipedia.org/wiki/Norm-(mathematics) Jan. 15, 2029, 9:54 AM).

In some implementations, each convolution filter can be normalized by the count of pixels in the convolution filter. The normalization can be along the spatial and/or time dimension. That is, the count of the pixels/feature values/units/size/dimensionality of the resulting feature map for an input cluster intensity image of size 115×115 at the spatial layer 1 can be 113×113, whereas at the temporal layer 7 it can be 101×101. The resulting sum of dot product of absolute values can be normalized by the filter size. Also, the temporal layers of the base caller have a time component dimension that varies, which can be used for the normalization.

In one implementation, the subset 1106 of the cluster feature maps are selected based on a percentage of the cluster feature maps that have the lowest contribution scores. In some implementations, the percentage ranges from 2% to 5%.

In one implementation, the number of epochs used in the retraining step 1144 to further train the pruned trained base caller 1142 is less than the number of epochs used in the training 1004 of the first base caller 1006. For example, the number of epochs used in the retraining step 1144 to further train the pruned trained base caller 1142 is fifteen and the number of epochs used in the training 1004 of the first base caller 10006 is fifty.

In one implementation, the subset 1106 of the clusters intensity images used in the cluster feature maps generation step 1104 is 15% to 30% of the cluster intensity images 1002 used for the training 1004 of the first base caller 1006, and is randomly selected at each iteration. In other implementations, the subset 1106 of the clusters intensity images used in the cluster feature maps generation step 1104 can be less than 15% and more than 30% of the cluster intensity images 1002, or between 15% and 30%.

Figure 13:
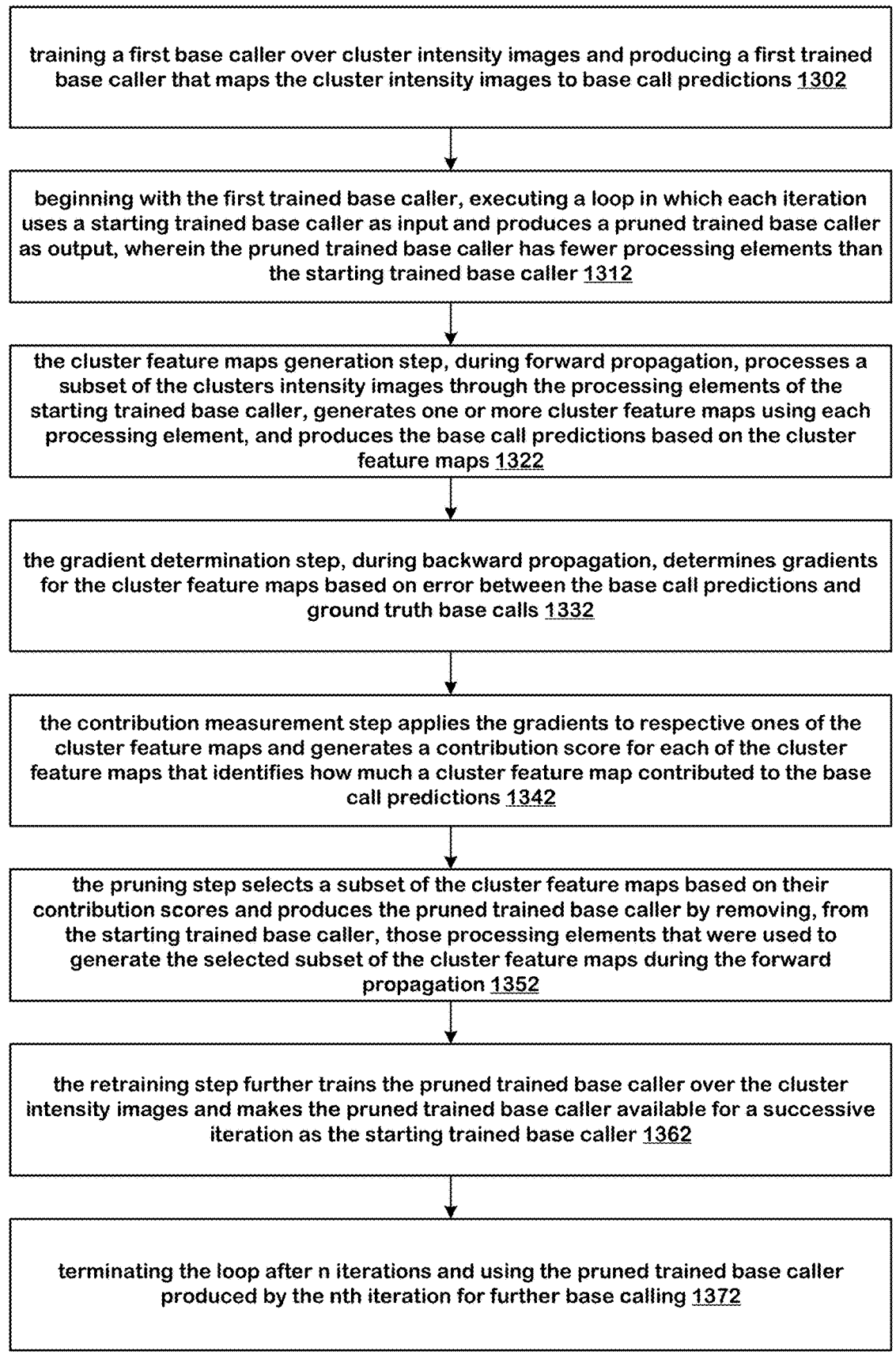
FIG. 13 shows one implementation of an artificial intelligence-based method of performing computationally efficient base calling.
Figure 15A:
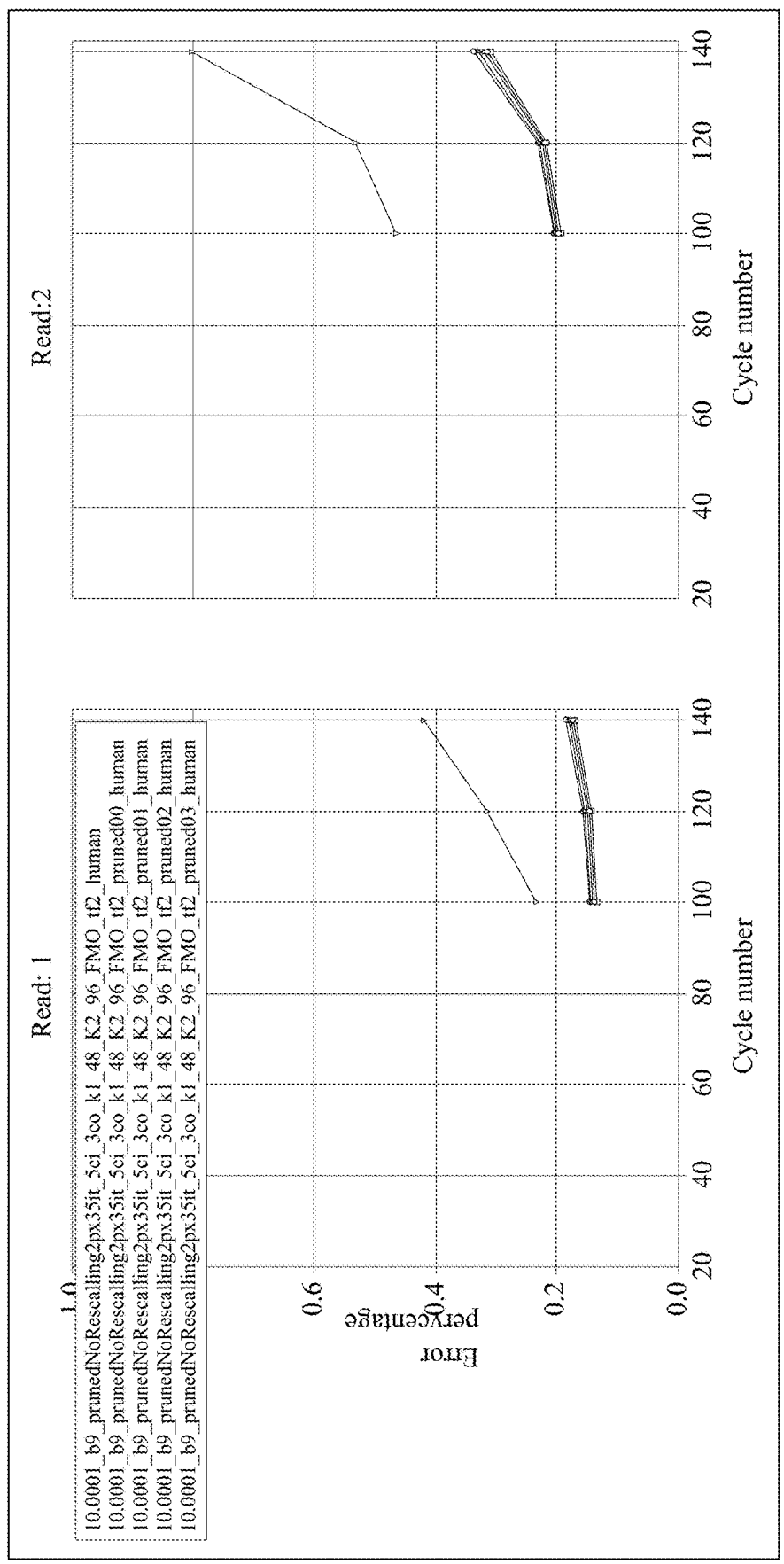
FIGS. 15A, 15B, 15C, 15D, 15E, and 15F are performance results that demonstrate that the technology disclosed implements computationally efficient base calling.
Figure 15B:
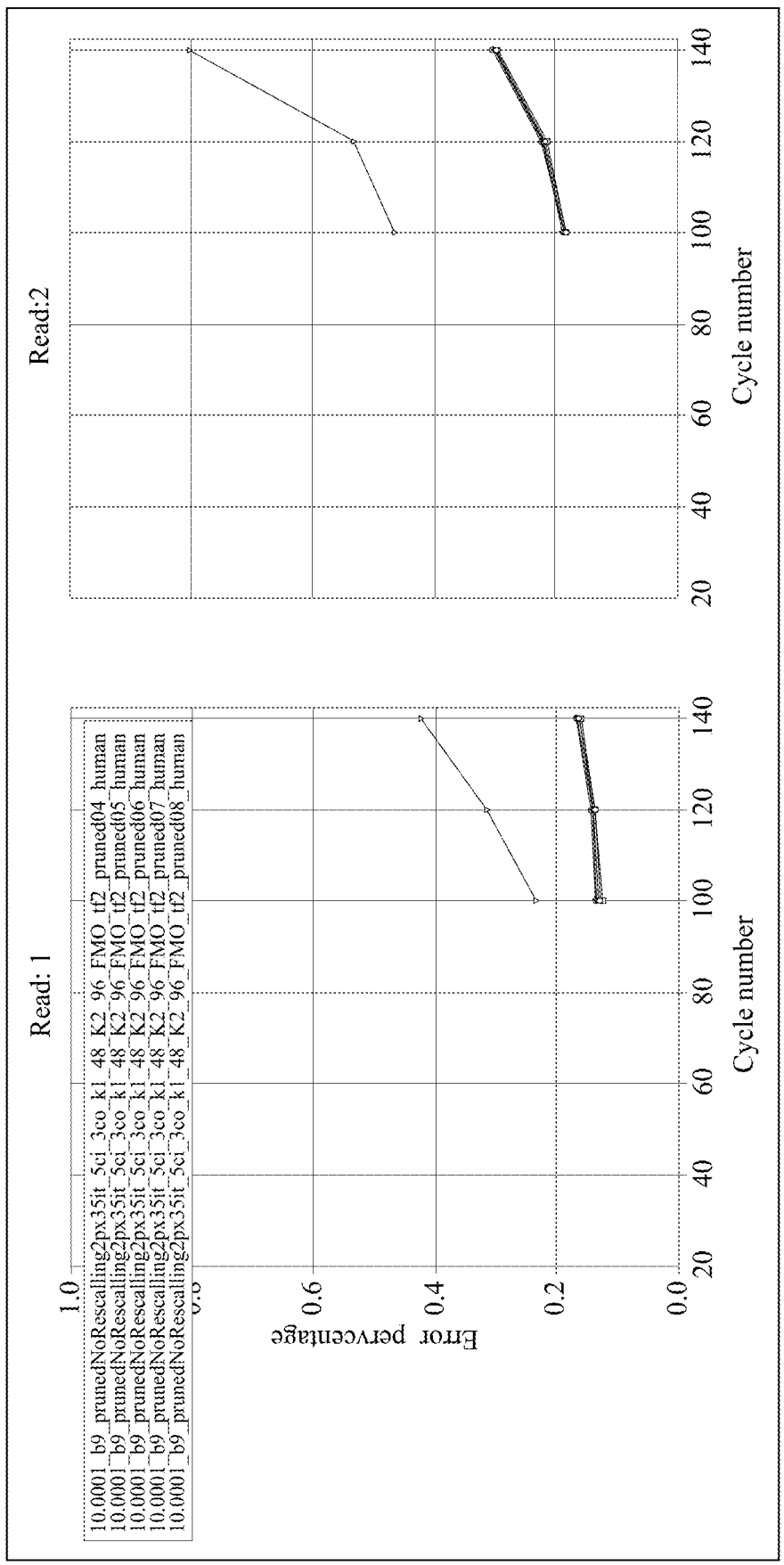
Figure 15C:
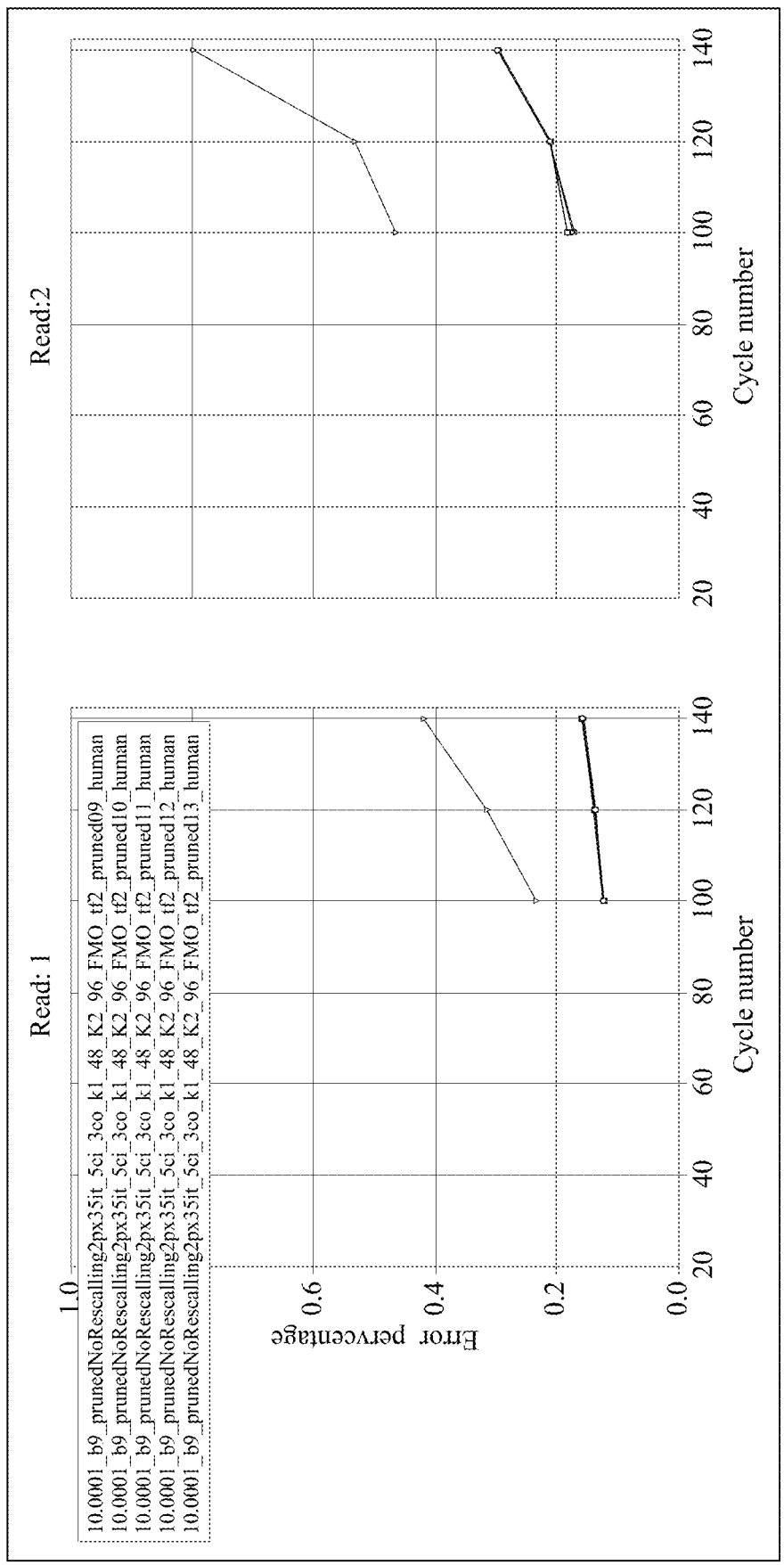
Figure 15D:
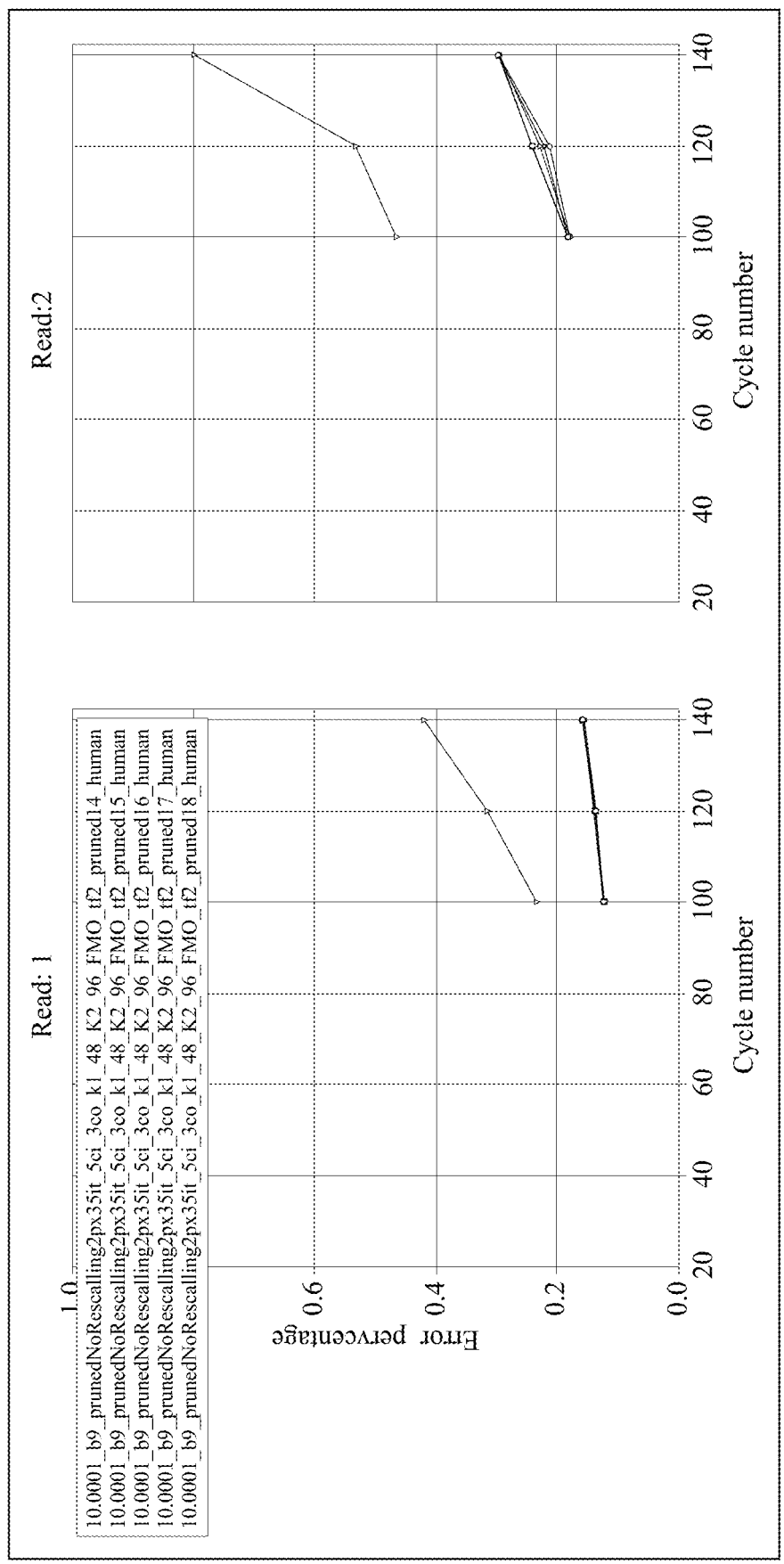
Figure 15E:
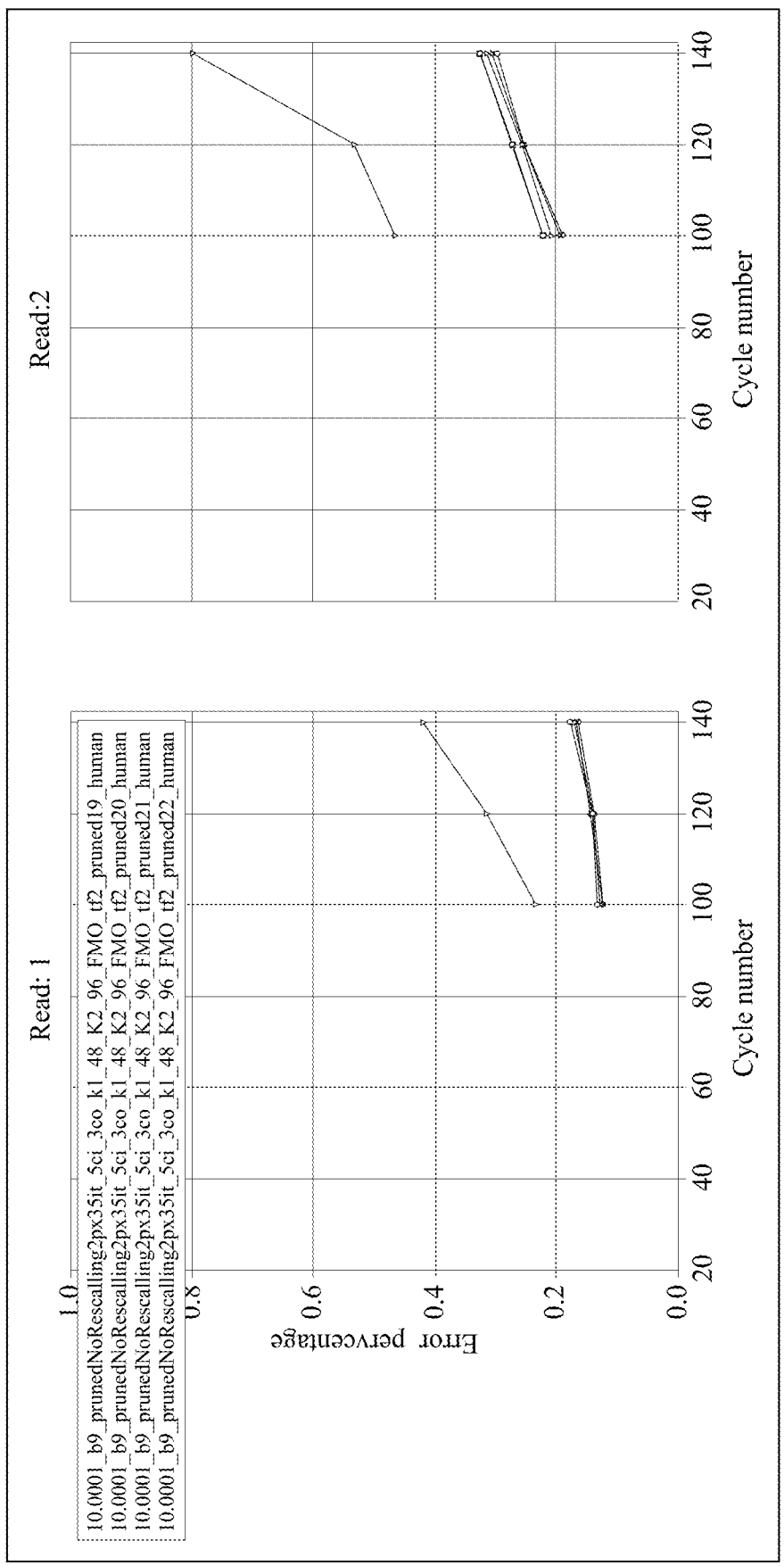
Figure 15F:
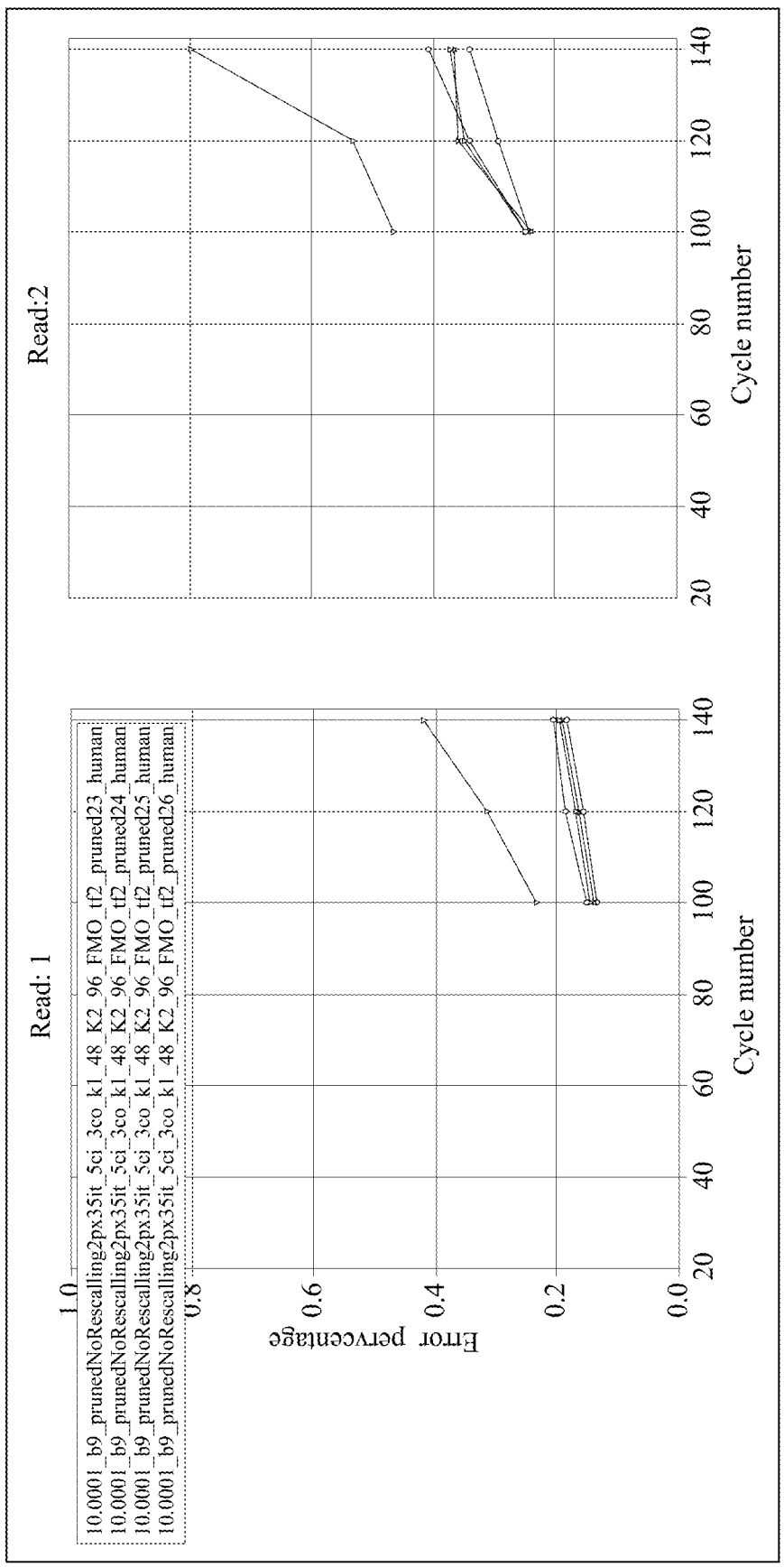

FIG. 13 shows one implementation of an artificial intelligence-based method of performing computationally efficient base calling.

At action 1302, the method incudes training a first base caller over cluster intensity images and producing a first trained base caller that maps the cluster intensity images to base call predictions.

At action 1312, the method includes beginning with the first trained base caller, executing a loop in which each iteration uses a starting trained base caller as input and produces a pruned trained base caller as output, wherein the pruned trained base caller has fewer processing elements than the starting trained base caller.

Each iteration comprises (i) a cluster feature maps generation step, (ii) a gradient determination step, (iii) a contribution measurement step, (iv) a pruning step, and (v) a retraining step.

At action 1322, the cluster feature maps generation step, during forward propagation, processes a subset of the clusters intensity images through the processing elements of the starting trained base caller, generates one or more cluster feature maps using each processing element, and produces the base call predictions based on the cluster feature maps.

At action 1332, the gradient determination step, during backward propagation, determines gradients for the cluster feature maps based on error between the base call predictions and ground truth base calls.

At action 1342, the contribution measurement step applies the gradients to respective ones of the cluster feature maps and generates a contribution score for each of the cluster feature maps that identifies how much a cluster feature map contributed to the base call predictions.

At action 1352, the pruning step selects a subset of the cluster feature maps based on their contribution scores and produces the pruned trained base caller by removing, from the starting trained base caller, those processing elements that were used to generate the selected subset of the cluster feature maps during the forward propagation.

At action 1362, the retraining step further trains the pruned trained base caller over the cluster intensity images and makes the pruned trained base caller available for a successive iteration as the starting trained base caller.

At action 1372, the method includes terminating the loop after n iterations and using the pruned trained base caller produced by the nth iteration for further base calling.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

FIG. 14 shows another implementation of an artificial intelligence-based method of performing computationally efficient base calling.

At action 1402, the method incudes training a first base caller over cluster intensity images and producing a first trained base caller that maps the cluster intensity images to base call predictions.

At action 1412, the method includes beginning with the first trained base caller, executing a loop in which each iteration uses a starting trained base caller as input and produces a pruned trained base caller as output, wherein the pruned trained base caller has fewer processing elements than the starting trained base caller.

Each iteration comprises (i) a cluster feature maps generation step, (ii) a contribution measurement step, (iii) a pruning step, and (iv) a retraining step.

At action 1422, the cluster feature maps generation step, during forward propagation, processes a subset of the clusters intensity images through the processing elements of the starting trained base caller, generates one or more cluster feature maps using each processing element, and produces the base call predictions based on the cluster feature maps.

At action 1432, the contribution measurement step generates a contribution score for each of the cluster feature maps that identifies how much a cluster feature map contributed to the base call predictions.

At action 1442, the pruning step selects a subset of the cluster feature maps based on their contribution scores and produces the pruned trained base caller by removing, from the starting trained base caller, those processing elements that were used to generate the selected subset of the cluster feature maps during the forward propagation.

At action 1452, the retraining step further trains the pruned trained base caller over the cluster intensity images and makes the pruned trained base caller available for a successive iteration as the starting trained base caller.

At action 1462, the method includes terminating the loop after n iterations and using the pruned trained base caller produced by the nth iteration for further base calling.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

FIGS. 15A, 15B, 15C, 15D, 15E, and 15F are performance results that demonstrate that the technology disclosed implements computationally efficient base calling.

The following plots illustrate the iterative pruning process output of the technology disclosed. We start from our standard Multicluster algorithm which the first trained base caller 1006 has seven spatial layers each with 48 filters, and 2 timewise convolutional layers each with 96 filters. We add an L1 norm regularization criterion to obtain a sparse set of filters, this results in an initial trained model that contains many of its convolutional kernels set to all zeros (the blue model in the first plot with suffix "_tf2_human"). A higher L1 regularization parameter leads to more filters being set to all zeros on this initially trained model.

Starting from this model we start a round of pruning iterations, during which we compute a pruning criterion on a random 15% of the training set. After ranking the filters according to this criterion, we eliminate the filters (typically we eliminate 2% of all filters across the model at each iteration) that are deemed least important, and then retrain the model for fine tuning. Each model resulting from pruning and fine tuning at each iteration is labelled in the following plots according to the suffix "prunedxx_human" where xx is a number from 00 to 35.

Initially we see that at each new pruning iteration the model performs better and better until iteration 14 (model "pruned13_human"). This is likely due to retraining the model with our learning rate annealing approach (train with high learning rate and progressively lower our learning rate). The use of cyclical learning rate training schedules (high to low learning rate as we add more training epochs, followed by more training epochs of high to low learning rate, leads to better models according to literature on the subject).

Later on, after iteration 14 as the model is trimmed down even further, we notice progressive degradation of the model mismatch rate.

Training iteration 24 (model "pruned23_human") shows to be a good candidate, from our pipeline output logs the model has the following filters:
model fine-tuned from loss 0.029168058224022388 to 0.022608762811869382
pruning iteration 24/35
spatial correction convolutional stack
L1 keeping 14/14 filters
L2 keeping 14/14 filters
L3 keeping 11/12 filters
L4 keeping 16/16 filters
L5 keeping 15/15 filters
L6 keeping 18/18 filters
L7 keeping 6/6 filters
timewise correction convolutional stack
L8 keeping 12/13 filters
L9 keeping 17/18 filters Taking these filter counts and translating them into numbers of operations per patch we have 295813196 operations which is 8% less operations than our standard K=14 model.

Interestingly, we also notice the squeezing of the last filter in the spatial convolutional stack down to 6 filters which corroborates our findings (disclosed in U.S. Provisional Patent Application No. 62/979,411) that data can be compressed significantly between the spatial correction layers and the timewise convolution layers.

Each of the following plots shows different models pruned and fine-tuned iteratively. A pruning session has been executed for each cycle along the x-axis, hence the lines between points at different cycles are here only to link independent models that are at the same pruning iteration.

The legend is partially hidden on these plots and the colors are from top to bottom (in the legend) blue, orange, green, red, black. Black fitted line represents performance measured on the same clusters as the disclosed deep learning model by Illumina's Real-Time Analysis (RTA) software (used herein as the baseline model).

Figure 19:
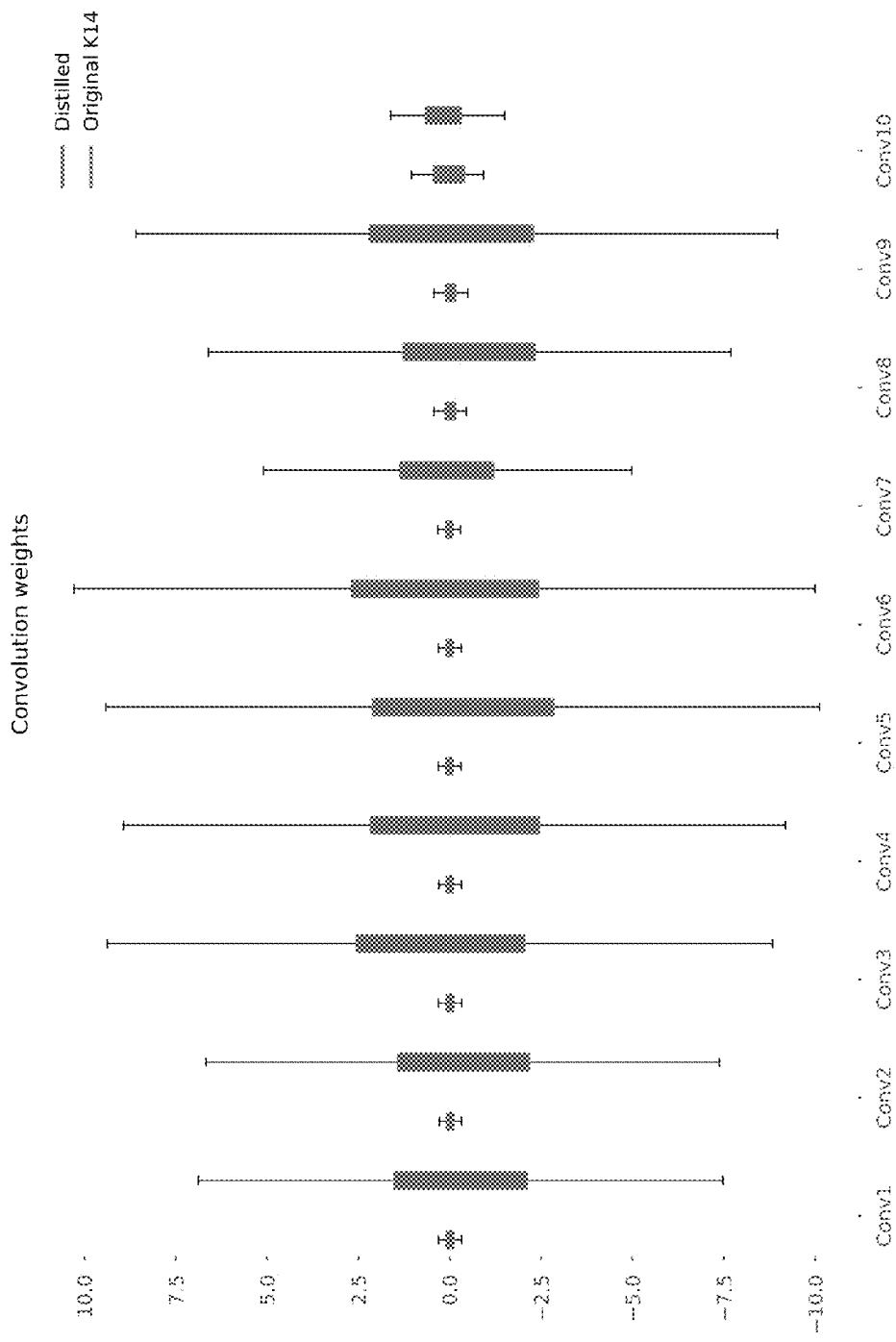
FIG. 19 depicts a box and whisker plot for one implementation of the technology disclosed that generates pruned convolution weights for a distilled base caller.

FIG. 19 depicts a box and whisker plot for one implementation of the technology disclosed that generates pruned convolution weights for a distilled base caller.

Figure 20:
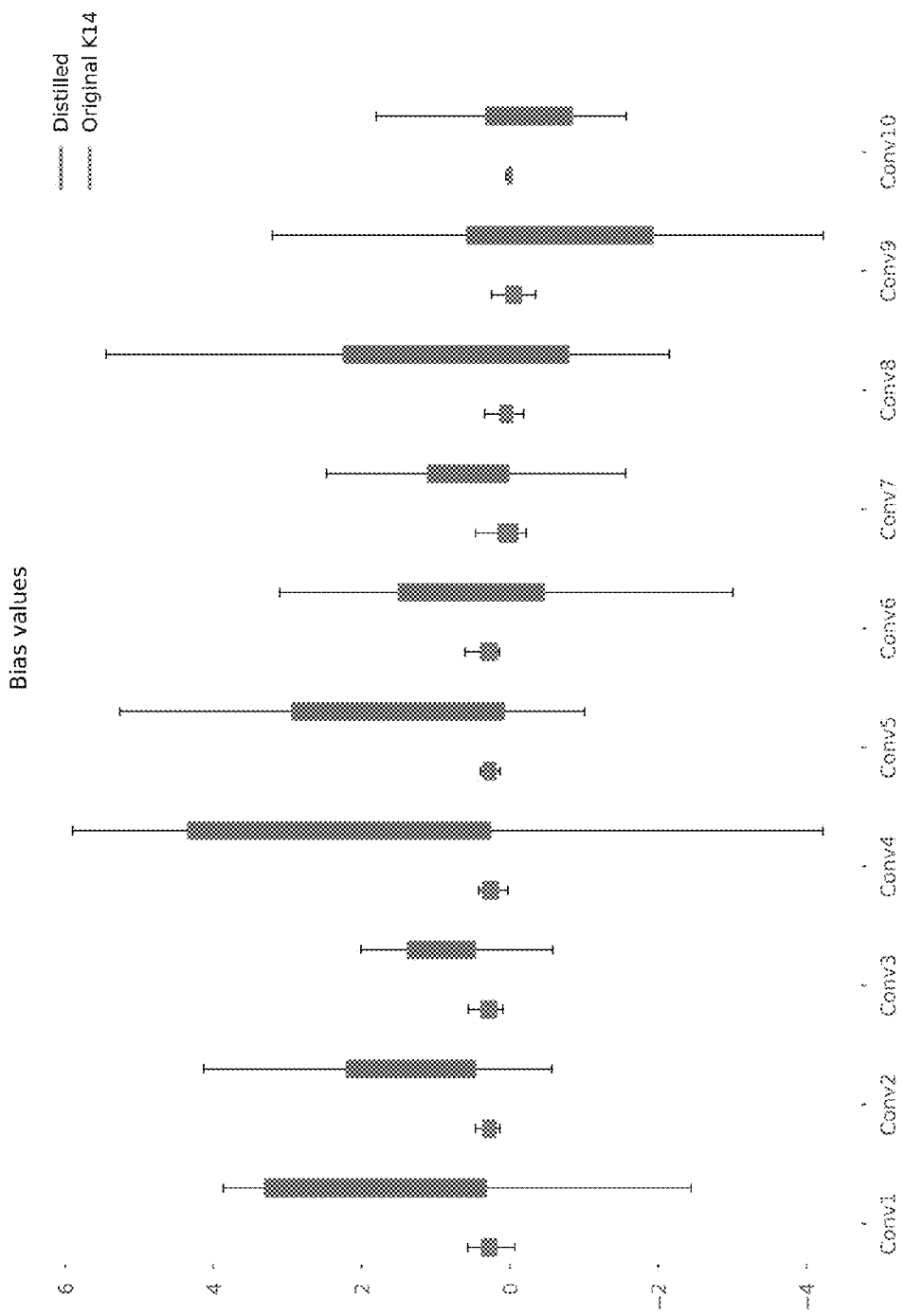
FIG. 20 depicts a box and whisker plot for one implementation of the technology disclosed that generates pruned convolution biases for a distilled base caller.

FIG. 20 depicts a box and whisker plot for one implementation of the technology disclosed that generates pruned convolution biases for a distilled base caller.

Figure 21:
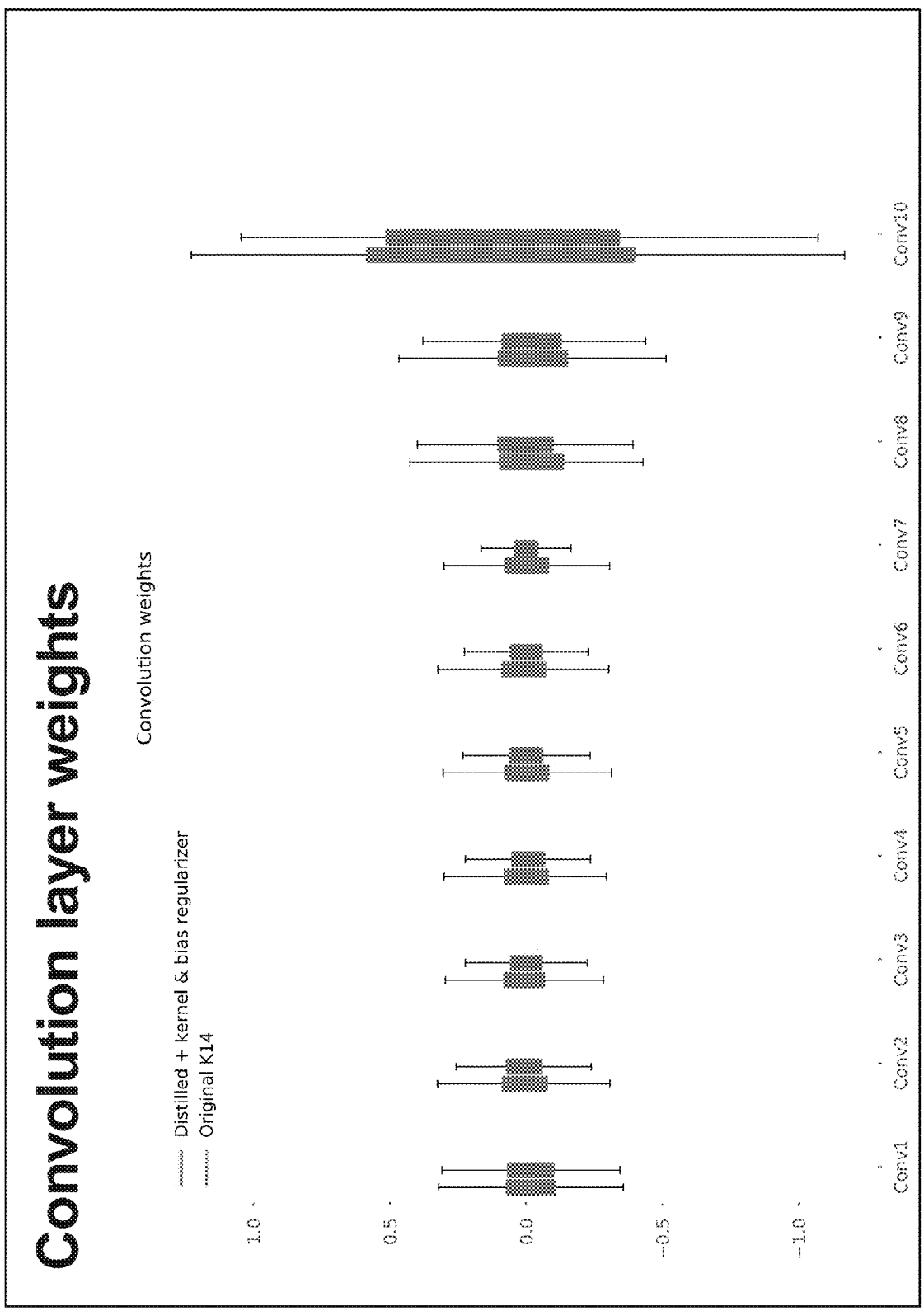
FIG. 21 depicts a box and whisker plot for one implementation of the technology disclosed that generates pruned convolution weights for a distilled base caller in which regularization is applied to both the convolution weights and the convolution biases.

FIG. 21 depicts a box and whisker plot for one implementation of the technology disclosed that generates pruned convolution weights for a distilled base caller in which regularization is applied to both the convolution weights and the convolution biases.

Figure 22:
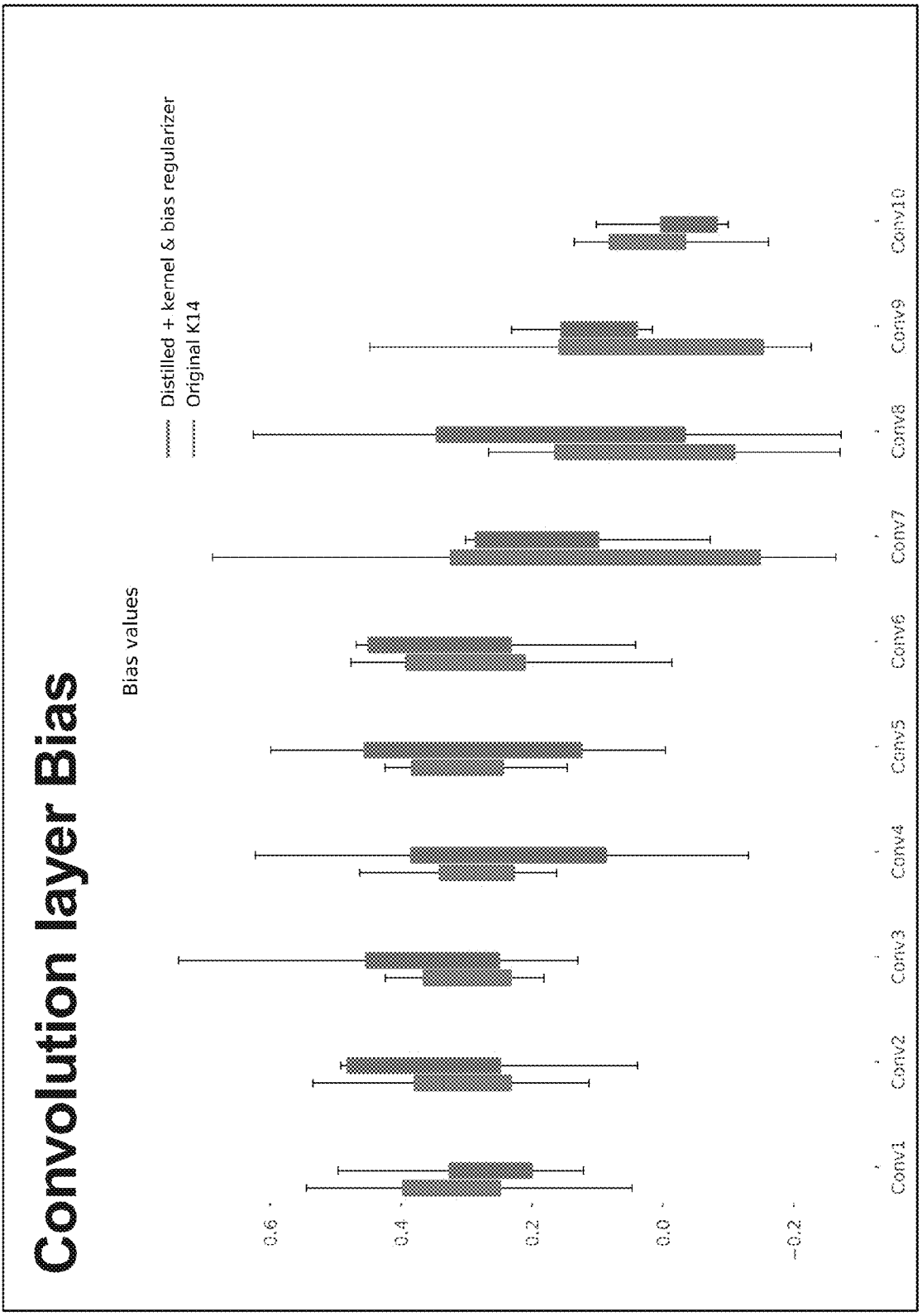
FIG. 22 depicts a box and whisker plot for one implementation of the technology disclosed that generates pruned convolution biases for a distilled base caller in which regularization is applied to both the convolution weights and the convolution biases.

FIG. 22 depicts a box and whisker plot for one implementation of the technology disclosed that generates pruned convolution biases for a distilled base caller in which regularization is applied to both the convolution weights and the convolution biases.

In some implementations, the technology disclosed uses an alternative learning scheduler, which starts from a higher learning rate and results in a better distilled model. FIGS. 19 to 22 illustrate different regularization parameters and convergence on 12 (0.00001) as both kernel and bias regularizers when distilling models. By doing so, the accuracy of the distilled model is not affected but the weights and biases are reduced to the range which can be accommodated on FPGA.

Terminology and Additional Implementations

Base calling includes incorporation or attachment of a fluorescently-labeled tag with an analyte. The analyte can be a nucleotide or an oligonucleotide, and the tag can be for a particular nucleotide type (A, C, T, or G). Excitation light is directed toward the analyte having the tag, and the tag emits a detectable fluorescent signal or intensity emission. The intensity emission is indicative of photons emitted by the excited tag that is chemically attached to the analyte.

Throughout this application, including the claims, when phrases such as or similar to "images, image data, or image regions depicting intensity emissions of analytes and their surrounding background" are used, they refer to the intensity emissions of the tags attached to the analytes. A person skilled in the art will appreciate that the intensity emissions of the attached tags are representative of or equivalent to the intensity emissions of the analytes to which the tags are attached, and are therefore used interchangeably. Similarly, properties of the analytes refer to properties of the tags attached to the analytes or of the intensity emissions from the attached tags. For example, a center of an analyte refers to the center of the intensity emissions emitted by a tag attached to the analyte. In another example, the surrounding background of an analyte refers to the surrounding background of the intensity emissions emitted by a tag attached to the analyte.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular implementation, the diameter of a nucleic acid cluster is about 0.5 µm, about 1 µm, about 1.5 µm, about 2 µm, about 2.5 µm, about 3 µm, about 4 µm, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 $mm^2$, no larger than about 500 $\mu m^2$, no larger than about 100 $\mu m^2$, no larger than about 10 $\mu m^2$, no larger than about 1 $\mu m^2$, no larger than about 500 $nm^2$, or no larger than about 100 $nm^2$, no larger than about 10 $nm^2$, no larger than about 5 $nm^2$, or no larger than about 1 $nm^2$. Alternatively or additionally, the analytes of an array will be no smaller than about 1 $mm^2$, no smaller than about 500 $\mu m^2$, no smaller than about 100 $\mu m^2$, no smaller than about 10 $\mu m^2$, no smaller than about 1 $\mu m^2$, no smaller than about 500 $nm^2$, no smaller than about 100 $nm^2$, no smaller than about 10 $nm^2$, no smaller than about 5 $nm^2$, or no smaller than about 1 $nm^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 μm, 50 μm, 10 μm, 5 μm, 1 μm, 0.5 μm, or less. Alternatively or additionally, an array can have analytes that are separated by an edge to edge distance of at least 0.5 μm, 1 μm, 5 μm, 10 μm, 50 μm, 100 μm, or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 μm, 50 μm, 10 μm, 5 μm, 1 μm, 0.5 μm, or less. Alternatively or additionally, the average analyte pitch in a regular pattern can be at least 0.5 μm, 1 μm, 5 μm, 10 μm, 50 μm, 100 μm, or more. These ranges can apply to the maximum or minimum pitch for a regular pattern as well. For example, the maximum analyte pitch for a regular pattern can be at most 100 µm, 50 µm, 10 µm, 5 µm, 1 µm, 0.5 µm, or less; and/or the minimum analyte pitch in a regular pattern can be at least 0.5 µm, 1 µm, 5 µm, 10 µm, 50 µm, 100 µm, or more.

The density of analytes in an array can also be understood in terms of the number of analytes present per unit area. For example, the average density of analytes for an array can be at least about $1 \times 10^3$ analytes/mm$^2$, $1 \times 10^4$ analytes/mm$^2$, $1 \times 10^5$ analytes/mm$^2$, $1 \times 10^6$ analytes/mm$^2$, $1 \times 10^7$ analytes/mm$^2$, $1 \times 10^8$ analytes/mm$^2$, or $1 \times 10^9$ analytes/mm$^2$, or higher. Alternatively or additionally the average density of analytes for an array can be at most about $1 \times 10^9$ analytes/mm$^2$, $1 \times 10^8$ analytes/mm$^2$, $1 \times 10^7$ analytes/mm$^2$, $1 \times 10^6$ analytes/mm$^2$, $1 \times 10^5$ analytes/mm$^2$, $1 \times 10^4$ analytes/mm$^2$, or $1 \times 10^3$ analytes/mm$^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 mm$^2$, 500 µm$^2$, 100 µm$^2$, 50 µm$^2$, 10 µm$^2$, 1 µm$^2$, 500 nm$^2$, 100 nm$^2$, 50 nm$^2$, 10 nm$^2$, or less. Alternatively or additionally, the geometric unit can occupy an area of greater than 10 nm$^2$, 50 nm$^2$, 100 nm$^2$, 500 nm$^2$, 1 µm$^2$, 10 µm$^2$, 50 µm$^2$, 100 µm$^2$, 500 µm$^2$, 1 mm$^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 µm, 50 µm, 10 µm, 5 µm, 1 µm or 0.5 µm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 60 70, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in Rakocevic, Goran et al. "Fast and accurate genomic analyses using genome graphs." Nature genetics vol. 51,2 (2019): 354-362. doi: 10.1038/s41588-018-0316-4https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ACTG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing and sequencing by ligation (SOLID sequencing). Depending on the sequencing methods, the length of each read may vary from about 30 bp to more than 10,000 bp. For example, the DNA sequencing method using SOLID sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered>100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3', i.e., with the sequence is written in the direction shown here, i.e., with 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "S", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 nm), visible (VIS) range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value. Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of a analyte of an object can specify the location of the analyte relative to location of a fiducial or other analyte of the object.

As used herein, the term "xy plane" is intended to mean a 2 dimensional area defined by straight line axes x and y. When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel. In other implementations, however, the offsets between color channels drift during a run and/or between runs, making offset-driven template generation difficult. In such implementations, the methods and systems provided herein can utilize offset-less template generation, which is described further below.

In some implementations of the above implementations, the system can comprise a flow cell. In some implementations, the flow cell comprises lanes, or other configurations, of tiles, wherein at least some of the tiles comprise one or more arrays of analytes. In some implementations, the analytes comprise a plurality of molecules such as nucleic acids. In certain aspects, the flow cell is configured to deliver a labeled nucleotide base to an array of nucleic acids, thereby extending a primer hybridized to a nucleic acid within a analyte so as to produce a signal corresponding to a analyte comprising the nucleic acid. In preferred implementations, the nucleic acids within a analyte are identical or substantially identical to each other.

In some of the systems for image analysis described herein, each image in the set of images includes color signals, wherein a different color corresponds to a different nucleotide base. In some implementations, each image of the set of images comprises signals having a single color selected from at least four different colors. In some implementations, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some implementations, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and running the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum. In contrast, other commercial sequencing technologies have recently ramped up their computing infrastructure for primary analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein. Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface. Line scanning detectors can be configured to scan a line along the y dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system, or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are examples only and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software and need not be divided up in precisely the same blocks as shown in the figures. Some can also be implemented on different processors or computers or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event, or value. If there is an intervening processing element, step or time period, the given signal, event, or value can still be "in dependence upon" the predecessor signal, event, or value. If the intervening processing element or step combines more than one signal, event or value, the signal output of the processing element or step is considered "in dependence upon" each of the signal, event, or value inputs. If the given signal, event, or value is the same as the predecessor signal, event, or value, this is merely a degenerate case in which the given signal, event or value is still considered to be "in dependence upon" or "dependent on" or "based on" the predecessor signal, event, or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

This application refers to "cluster images" and "cluster intensity images" interchangeably.

Particular Implementations

We describe various implementations of artificial intelligence-based base calling using knowledge distillation techniques. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

We disclose an artificial intelligence-based method of base calling. The method includes training a teacher (first, bigger) base caller by using a first set of cluster images as training data. The first set of cluster images are annotated with first ground truth data that uses discrete valued labels to identify a correct base call. In one implementation, the discrete valued labels are one-hot encoded with a one-value for a correct base and zero-values for incorrect bases. In one implementation, the discrete valued labels have a near-one-value for the correct base and near-zero-values for the incorrect bases.

The method includes evaluating a second set of cluster images as inference data by applying the trained teacher (first, bigger) base caller on the second set of cluster images and generating base call predictions. The base call predictions are represented by continuous valued weights that identify a predicted base call. In one implementation, the continuous valued weights are part of a probability distribution for a correct base being Adenine (A), Cytosine (C), Thymine (T), and Guanine (G).

The method includes training a student (second, smaller) base caller using the second set of cluster images as training data. The second set of cluster images are annotated with second ground truth data that identifies a correct base call based on (i) the discrete valued labels and (ii) the continuous valued weights.

The student (second, smaller) base caller has fewer processing modules and parameters than the teacher (first, bigger) base caller. In one implementation, one of the processing modules is neural network layers. In one implementation, one of the parameters is interconnections between the neural network layers. In one implementation, one of the processing modules is neural network filters. In one implementation, one of the processing modules is neural network kernels. In one implementation, one of the parameters is multiplication and addition operations.

The method includes evaluating a third set of cluster images as inference data by applying the trained student (second, smaller) base caller on the third set of cluster images and generating base call predictions.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the method includes training the student (second, smaller) base caller using the second set of cluster images as training data. The second set of cluster images are annotated with the second ground truth data that identifies the correct base call based on the continuous valued weights.

In one implementation, a cluster image depicts intensity emissions of clusters. The intensity emissions are captured during a sequencing cycle of a sequencing run. In one implementation, the cluster image further depicts intensity emissions of background surrounding the clusters.

In one implementation, the first, second, and third sets of cluster images share one or more common cluster images.

In one implementation, the method includes training an ensemble of the teacher (first, bigger) base caller by using the first set of cluster images as training data. The first set of cluster images are annotated with the first ground truth data that uses the discrete valued labels to identify the correct base call. The ensemble comprises two or more instances of the teacher (first, bigger) base caller.

The method includes evaluating the second set of cluster images as inference data by applying the trained teacher (first, bigger) base caller on the second set of cluster images and generating the base call predictions. The base call predictions are represented by the continuous valued weights that identify the predicted base call.

The method includes training the student (second, smaller) base caller using the second set of cluster images as training data. The second set of cluster images are annotated with the second ground truth data that identifies the correct base call based on (i) the discrete valued labels and (ii) the continuous valued weights. The student (second, smaller) base caller has fewer processing modules and parameters than the ensemble of the teacher (first, bigger) base caller.

The method includes evaluating the third set of cluster images as inference data by applying the trained student (second, smaller) base caller on the third set of cluster images and generating the base call predictions.

In one implementation, the method includes implementing the trained student (second, smaller) base caller on one or more parallel processors of a sequencing instrument for real-time base calling.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In another implementation, we disclose a system for artificial intelligence-based base calling. The system comprises a base caller (student, second, smaller base caller/engine) trained on cluster images that are annotated with ground truth data that identifies a correct base call based on (i) discrete valued labels of ground truth data used to train another base caller and (ii) continuous valued weights of base call predictions generated by the another base caller (teacher, first, bigger base caller/engine) for the cluster images during inference.

The base caller (student, second, smaller base caller/engine) has fewer processing modules and parameters than the another base caller (teacher, first, bigger base caller/engine). In one implementation, one of the processing modules is neural network layers. In one implementation, one of the parameters is interconnections between the neural network layers. In one implementation, one of the processing modules is neural network filters. In one implementation, one of the processing modules is neural network kernels. In one implementation, one of the parameters is multiplication and addition operations.

The base caller (student, second, smaller base caller/engine) is configured to evaluate additional cluster images and generate, for the additional cluster images, base call predictions.

The discrete valued labels are one-hot encoded with a one-value for a correct base and zero-values for incorrect bases. The continuous valued weights are part of a probability distribution for a correct base being Adenine (A), Cytosine (C), Thymine (T), and Guanine (G).

In yet another implementation, we disclose a system for artificial intelligence-based base calling. The system comprises a teacher (first, bigger) base caller trained on cluster images that are annotated with ground truth data that identifies a correct base call based on base call predictions generated by a student (second, smaller) base caller.

In yet further implementation, we disclose an artificial intelligence-based method of base calling. The method includes training a teacher (first, bigger) base caller by using a first set of cluster images as training data. The first set of cluster images are annotated with first ground truth data that uses discrete valued labels to identify a correct base call. In one implementation, the discrete valued labels are one-hot encoded with a one-value for a correct base and zero-values for incorrect bases. In one implementation, the discrete valued labels have a near-one-value for the correct base and near-zero-values for the incorrect bases.

The method includes evaluating a second set of cluster images as inference data by applying the trained teacher (first, bigger) base caller on the second set of cluster images and generating base call predictions. The base call predictions are represented by continuous valued weights that identify a predicted base call. In one implementation, the continuous valued weights are part of a probability distribution for a correct base being Adenine (A), Cytosine (C), Thymine (T), and Guanine (G).

The method includes training a student (second, smaller) base caller using the second set of cluster images as training data. The second set of cluster images are annotated with second ground truth data that identifies a correct base call based on (i) the discrete valued labels and (ii) the continuous valued weights.

In some implementations, the teacher base caller (first, bigger engine/model) is a neural network-based base caller. In one implementation, the teacher base caller (first, bigger engine/model) is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and an RNN.

In yet other implementations, the teacher base caller (first, bigger engine/model) can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

In some implementations, the student base caller (second, smaller engine/model) is a neural network-based base caller. In one implementation, the student base caller (second, smaller engine/model) is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the student base caller (second, smaller engine/model) can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

Clauses

We disclose the following clauses:

36. An artificial intelligence-based method of performing computationally efficient base calling, the method including:

training a first base caller over cluster intensity images and producing a first trained base caller that maps the cluster intensity images to base call predictions;

beginning with the first trained base caller, executing a loop in which each iteration uses a starting trained base caller as input and produces a pruned trained base caller as output, wherein the pruned trained base caller has fewer processing elements than the starting trained base caller;

wherein each iteration comprises (i) a base call prediction step, (ii) a contribution measurement step, (iii) a pruning step, and (iv) a retraining step;

wherein the base call prediction step, during forward propagation, processes a subset of the clusters intensity images through processing elements of the starting trained base caller and produces the base call predictions;

wherein the contribution measurement step generates a contribution score for each of the processing elements that identifies how much a processing element contributed to the base call predictions;

wherein the pruning step selects a subset of the processing elements based on their contribution scores and produces the pruned trained base caller by removing, from the starting trained base caller, the selected subset of the processing elements;

wherein the retraining step further trains the pruned trained base caller over the cluster intensity images and makes the pruned trained base caller available for a successive iteration as the starting trained base caller; and terminating the loop after n iterations and using the pruned trained base caller produced by the nth iteration for further base calling.

37. The artificial intelligence-based method of clause 36, wherein the contribution score for the processing element is generated by:

applying an absolute function to weights of the processing element and generating absolute weight values; and summing the absolute weight values and producing the contribution score for the processing element.

38. The artificial intelligence-based method of clause 36, implementing each of the clauses which ultimately depend from clauses 1 and 27.

39. An artificial intelligence-based method of performing computationally efficient base calling, the method including:

training a first base caller over cluster intensity images and producing a first trained base caller that maps the cluster intensity images to base call predictions;

beginning with the first trained base caller, executing a loop in which each iteration uses a starting trained base caller as input and produces a pruned trained base caller as output, wherein the pruned trained base caller has fewer processing elements than the starting trained base caller;

wherein each iteration comprises (i) a cluster feature maps generation step, (ii) a gradient determination step, (iii) an intermediate feature value generation step, (iv) a feature sum generation step, (v) a subset output generation step, (vi) a subset selection step, (vii) a pruning step, (viii) a cluster feature map identification step, and (ix) a retraining step;

wherein the cluster feature maps generation step, during forward propagation, processes a subset of the clusters intensity images through the processing elements of the starting trained base caller, generates one or more cluster feature maps using each processing element, and produces the base call predictions based on the cluster feature maps;

wherein the gradient determination step, during backward propagation, determines gradients for the cluster feature maps based on error between the base call predictions and ground truth base calls;

wherein the intermediate feature value generation step multiplies feature values in the cluster feature maps with respective ones of the gradients and produces a set of intermediate feature values for each of the cluster features maps;

wherein the feature sum generation step sums the intermediate feature values in the set of intermediate feature values and produces a feature sum for each of the cluster features maps, thereby producing a set of feature sums for the starting trained base caller;

wherein the subset output generation step processes subsets of feature sums in the set of feature sums and generates a subset output for each of the subsets;

wherein the subset selection step selects one or more of the subsets of feature sums based on evaluating their respective subset outputs against one or more of the feature sums in the set of feature sums;

wherein the cluster feature map identification step identifies those cluster feature maps whose feature sums are part of the selected subsets of feature sums;

wherein the pruning step produces the pruned trained base caller by removing, from the starting trained base caller, those processing elements that were used to generate the identified cluster feature maps during the forward propagation;

wherein the retraining step further trains the pruned trained base caller over the cluster intensity images and makes the pruned trained base caller available for a successive iteration as the starting trained base caller; and terminating the loop after n iterations and using the pruned trained base caller produced by the nth iteration for further base calling.

40. The artificial intelligence-based method of clause 39, wherein the subset output for a subset of feature sums is based on an additive sum of the feature sums in the subset.

41. The artificial intelligence-based method of clause 40, wherein the subset output for the subset of feature sums is based on an average of the feature sums in the subset.

42. The artificial intelligence-based method of clause 41, wherein the subset output for the subset of feature sums is based on an exponential sum of the feature sums in the subset.

43. The artificial intelligence-based method of clause 42, wherein the subset output for the subset of feature sums is based on a multiplicative interaction of the feature sums in the subset.

44. The artificial intelligence-based method of clause 43, wherein the subset selection step selects the subsets of feature sums based on evaluating their respective subset outputs against a lowest one of the feature sums in the set of feature sums and selecting those subsets of feature sums whose subset outputs are lower than the lowest one of the feature sums in the set of feature sums.

45. The artificial intelligence-based method of clause 44, wherein the subset selection step selects the subsets of feature sums based on evaluating their respective subset outputs against a plurality of lowest ones of the feature sums in the set of feature sums and selecting those subsets of feature sums whose subset outputs are lower than the lowest ones of the feature sums in the plurality of lowest ones of the feature sums.

46. The artificial intelligence-based method of clause 45, wherein the subset selection step selects those subsets of feature sums whose subset outputs are zero.

47. The artificial intelligence-based method of clause 46, wherein the subset selection step selects those subsets of feature sums whose subset outputs are closest to zero.

48. An artificial intelligence-based method of performing computationally efficient base calling, the method including:

training a first base caller over cluster intensity images and producing a first trained base caller that maps the cluster intensity images to base call predictions;

beginning with the first trained base caller, executing a loop in which an iteration uses a starting trained base caller as input and produces a pruned trained base caller as output, wherein the pruned trained base caller has fewer processing elements than the starting trained base caller; wherein the iteration comprises (i) a base call prediction step, (ii) a contribution measurement step, and (iii) a pruning step;

wherein the base call prediction step, during forward propagation, processes one or more of the clusters intensity images through processing elements of the starting trained base caller and produces the base call predictions;

wherein the contribution measurement step determines a contribution score for each of the processing elements that identifies how much a processing element contributed to the base call predictions; and wherein the pruning step selects a subset of the processing elements based on their contribution scores and produces the pruned trained base caller by removing, from the starting trained base caller, the selected subset of the processing elements.

49. The artificial intelligence-based method of clause 48, wherein the contribution score for each of the processing elements is determined based on their corresponding feature maps.

50. The artificial intelligence-based method of clause 48, wherein the loop comprises one or more iterations.

51. The artificial intelligence-based method of clause 48, wherein the processing element is a filter.

52. The artificial intelligence-based method of clause 51, wherein the processing element is a convolution filter.

53. The artificial intelligence-based method of clause 48, wherein the processing element is a kernel.

54. The artificial intelligence-based method of clause 53, wherein the processing element is a convolution kernel.

55. The artificial intelligence-based method of clause 48, wherein the processing element is a layer.

56. The artificial intelligence-based method of clause 55, wherein the processing element is a convolution layer.

Other implementations of the method described above can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

What is claimed is:

1. An artificial intelligence-based method of base calling nucleic acid samples using a sequencing instrument, the artificial intelligence-based method including:

training a first base caller by using a first set of cluster images as training data, wherein the first set of cluster images depict a first set of nucleic acid clusters and are annotated with first ground truth data that uses a first set of discrete valued labels to identify a correct base call;

evaluating a second set of cluster images depicting a second set of nucleic acid clusters as inference data by applying the trained first base caller to the second set of cluster images and generating base call predictions, wherein the second set of cluster images is distinct from the first set of cluster images; and wherein the base call predictions are represented by continuous valued weights that identify a predicted base call;

generating hybrid ground truth data for annotating the second set of cluster images based on a combination of a second set of discrete valued labels corresponding to the second set of cluster images and the continuous valued weights generated for the second set of cluster images by the trained first base caller;

training a second base caller using the second set of cluster images and the hybrid ground truth data generated for the second set of cluster images as training data, wherein the second base caller has fewer processing modules and parameters than the first base caller; and implementing the trained second base caller via the sequencing instrument to perform base calling for a third set of nucleic acid clusters derived from a sample by:

capturing, at imaging events of sequencing cycles by one or more light detectors of the sequencing instrument, a third set of cluster images depicting the third set of nucleic acid clusters comprising labeled nucleotide bases; and evaluating the third set of cluster images as inference data by using the processing modules and the parameters of the trained second base caller to generate base call predictions that a labeled nucleotide base comprising adenine (A), cytosine (C), thymine (T), or guanine (G) has been incorporated at a sequencing cycle into one or more of the third set of nucleic acid clusters.

2. The artificial intelligence-based method of claim 1, wherein at least one of the first set of discrete valued labels or the second set of discrete valued labels are one-hot encoded with a one-value for a correct base and zero-values for incorrect bases.

3. The artificial intelligence-based method of claim 2, wherein at least one of the first set of discrete valued labels or the second set of discrete valued labels have a near-one-value for the correct base and near-zero-values for the incorrect bases.

4. The artificial intelligence-based method of claim 1, wherein the continuous valued weights are part of a probability distribution for a correct base being Adenine (A), Cytosine (C), Thymine (T), and Guanine (G).

5. The artificial intelligence-based method of claim 1, wherein one of the processing modules comprises neural network layers.

6. The artificial intelligence-based method of claim 5, wherein one of the parameters comprises interconnections between the neural network layers.

7. The artificial intelligence-based method of claim 1, wherein one of the processing modules comprises neural network filters.

8. The artificial intelligence-based method of claim 1, wherein capturing the third set of cluster images by the one or more light detectors of the sequencing instrument comprises capturing the third set of cluster images depicting the third set of nucleic acid clusters, each nucleic acid cluster having a diameter measured in micrometers.

9. The artificial intelligence-based method of claim 1, wherein evaluating the third set of cluster images to generate the base call predictions that the labeled nucleotide base has been incorporated at the sequencing cycle comprises detecting, within one or more cluster images from the third set of cluster images, the labeled nucleotide base having a diameter measured in micrometers.

10. The artificial intelligence-based method of claim 1, further comprising generating the hybrid ground truth data corresponding to the second set of cluster images by:
- modifying the continuous valued weights generated for the second set of cluster images by the trained first base caller based on a modification parameter; and
- combining the modified continuous valued weights with the second set of discrete valued labels.

11. The artificial intelligence-based method of claim 1, wherein evaluating the third set of cluster images to generate the base call predictions comprises:
- distinguishing between optical signals captured in the third set of cluster images using one or more cluster masks; and
- generating, via the trained second base caller, the base call predictions based on the optical signals distinguished using the one or more cluster masks.

12. The artificial intelligence-based method of claim 1, wherein evaluating the third set of cluster images to generate the base call predictions comprises:
- extracting, from the third set of cluster images via the trained second base caller, intensity data for the third set of nucleic acid clusters and a surrounding background; and
- generating, via the trained second base caller, the base call predictions based on the intensity data.

13. The artificial intelligence-based method of claim 1, wherein the second base caller has less than twenty-five percent of a number of processing modules included in the first base caller and less than ten percent of a number of parameters included in the first base caller.

14. The artificial intelligence-based method of claim 1, further comprising:
- training an ensemble of the first base caller by using the first set of cluster images as training data,
- wherein the first set of cluster images are annotated with the first ground truth data that uses the first set of discrete valued labels to identify the correct base call, and
- wherein the ensemble comprises two or more instances of the first base caller;
- evaluating the second set of cluster images as inference data by applying the trained first base caller on the second set of cluster images and generating the base call predictions,
- wherein the base call predictions are represented by the continuous valued weights that identify the predicted base call;
- training the second base caller using the second set of cluster images as training data,
- wherein the second set of cluster images are annotated with the hybrid ground truth data that identifies the correct base call based on the combination of:
  - (i) the second set of discrete valued labels, and
  - (ii) the continuous valued weights;
  - wherein the second base caller has fewer processing modules and parameters than the ensemble of the first base caller; and
- evaluating the third set of cluster images as inference data by applying the trained second base caller on the third set of cluster images and generating the base call predictions.

15. The artificial intelligence-based method of claim 1, wherein the one or more light detectors of the sequencing instrument capture the third set of cluster images based on detecting emission signals from the third set of nucleic acid clusters at each sequencing cycle of a sequencing run for base calling the third set of nucleic acid clusters.

16. A system for artificial intelligence-based base calling nucleic acid samples, comprising:
- at least one processor;
- a sequencing instrument; and
- a base caller on the sequencing instrument and trained on cluster images that are annotated with hybrid ground truth data that identifies correct base calls for one or more nucleic acid clusters depicted by the cluster images based on a combination of:
  - (i) discrete valued labels of ground truth data used to train an additional base caller, and
  - (ii) continuous valued weights of base call predictions generated by the additional base caller for the cluster images during inference;
- wherein the base caller has fewer processing modules and parameters than the additional base caller, and
- wherein the cluster images depict nucleic acid clusters; and
- wherein the base caller is configured to be implemented via the sequencing instrument to perform (1) base calling for additional nucleic acid clusters derived from a sample by evaluating, using the processing modules and the parameters of the base caller, additional cluster images of the additional nucleic acid clusters captured at imaging events of sequencing cycles by one or more light detectors of the sequencing instrument and (2) generating, for the additional cluster images, base call predictions that a labeled nucleotide base comprising adenine (A), cytosine (C), thymine (T), or guanine (G) has been incorporated at a sequencing cycle into one or more of the additional nucleic acid clusters.

17. The system of claim 16, wherein the discrete valued labels are one-hot encoded with a one-value for a correct base and zero-values for incorrect bases.

18. The system of claim 16, wherein the continuous valued weights are part of a probability distribution for a correct base being Adenine (A), Cytosine (C), Thymine (T), and Guanine (G).

19. The system of claim 16, wherein:
- one of the processing modules comprises neural network layers,
- one of the parameters comprises interconnections between the neural network layers, one of the processing modules comprises neural network filters, one of the processing modules comprises neural network kernels, and
- one of the parameters comprises multiplication and addition operations.

20. A system for artificial intelligence-based base calling nucleic acid samples using a sequencing instrument, comprising:
- at least one processor; and
- a non-transitory computer-readable medium comprising instructions that, when executed by the at least one processor cause the system to:
  - train a first base caller by using a first set of cluster images as training data,
  - wherein the first set of cluster images depict a first set of nucleic acid clusters and are annotated with first ground truth data that uses a first set of discrete valued labels to identify a correct base call;
  - evaluate a second set of cluster images depicting a second set of nucleic acid clusters as inference data by applying the trained first base caller on the second set of cluster images and generating base call predictions,
    wherein the second set of cluster images is distinct from the first set of cluster images; and
    wherein the base call predictions are represented by continuous valued weights that identify a predicted base call;
generate hybrid ground truth data for annotating the second set of cluster images based on a combination of a second set of discrete valued labels corresponding to the second set of cluster images and the continuous valued weights generated for the second set of cluster images by the trained first base caller;
train a second base caller using the second set of cluster images and the hybrid ground truth data generated for the second set of cluster images as training data,
wherein the second base caller has fewer processing modules and parameters than the first base caller; and
implement the trained second base caller via the sequencing instrument to perform base calling for a third set of nucleic acid clusters derived from a sample by:
    extending, during sequencing cycles of a sequencing run, a nucleotide sequence by adding a labeled nucleotide base to the nucleotide sequence;
    exciting, during the sequencing cycles, the labeled nucleotide base using one or more light sources of the sequencing instrument;
    capturing, at imaging events of the sequencing cycles by one or more light detectors of the sequencing instrument and in response to exciting the labeled nucleotide base during the sequencing cycles, a third set of cluster images depicting the third set of nucleic acid clusters comprising labeled nucleotide bases; and
    evaluating the third set of cluster images as inference data by using the processing modules and the parameters of the trained second base caller to generate base call predictions for the sequencing cycles that the labeled nucleotide base comprises adenine (A), cytosine (C), thymine (T), or guanine (G) has been incorporated at a sequencing cycle into one or more of the third set of nucleic acid clusters.

\* \* \* \* \*